United States Patent
Gundluru et al.

(10) Patent No.: US 9,827,229 B2
(45) Date of Patent: Nov. 28, 2017

(54) SMALL MOLECULE SECURININE AND NORSECURININE ANALOGS AND THEIR USE IN CANCERS, INFLAMMATORY DISEASES AND INFECTIONS

(71) Applicant: INVENIO THERAPEUTICS INC., Lexington, KY (US)

(72) Inventors: Mahesh K. Gundluru, Lexington, KY (US); Mukesh Agarwal, Solon, OH (US); Zhiqing Xia, Lexington, KY (US); Goutam Karan, Lexington, KY (US); David Wald, Shaker Heights, OH (US)

(73) Assignee: INVENIO THERAPEUTICS INC., Lexington, KY (US)

( * ) Notice: Subject to any disclaimer, the term of this patent is extended or adjusted under 35 U.S.C. 154(b) by 0 days.

(21) Appl. No.: 15/026,749

(22) PCT Filed: Oct. 3, 2014

(86) PCT No.: PCT/US2014/059112
§ 371 (c)(1),
(2) Date: Apr. 1, 2016

(87) PCT Pub. No.: WO2015/051284
PCT Pub. Date: Apr. 9, 2015

(65) Prior Publication Data
US 2016/0229861 A1    Aug. 11, 2016

Related U.S. Application Data

(60) Provisional application No. 61/886,448, filed on Oct. 3, 2013, provisional application No. 61/942,880, filed
(Continued)

(51) Int. Cl.
*A61K 31/33* (2006.01)
*A61K 31/437* (2006.01)
(Continued)

(52) U.S. Cl.
CPC .......... *A61K 31/437* (2013.01); *A61K 31/407* (2013.01); *A61K 31/439* (2013.01);
(Continued)

(58) Field of Classification Search
CPC .. A61K 31/437; A61K 31/407; A61K 31/439; A61K 31/496; A61K 31/5365;
(Continued)

(56) References Cited

U.S. PATENT DOCUMENTS

2011/0028407 A1    2/2011  Jutila et al.
2012/1029586      11/2012 Hrdlicka et al.

FOREIGN PATENT DOCUMENTS

WO    2008/143876 A2    11/2008

OTHER PUBLICATIONS

Li et al (Tetrahedron, 2012, 68, 3972-3979).*
(Continued)

*Primary Examiner* — Jason Sims
*Assistant Examiner* — Ibrahim D Bori
(74) *Attorney, Agent, or Firm* — King & Schickli, PLLC

(57) ABSTRACT

The present invention relates to novel securinine and norsecurine analogs and their applicapility in treating cellular proliferative disorders.

5 Claims, 1 Drawing Sheet

Related U.S. Application Data on Feb. 21, 2014, provisional application No. 62/051,595, filed on Sep. 17, 2014.

(51) Int. Cl.

| | | |
|---|---|---|
| *A61K 31/439* | (2006.01) | |
| *C07D 491/18* | (2006.01) | |
| *A61K 31/407* | (2006.01) | |
| *A61K 31/537* | (2006.01) | |
| *A61K 45/06* | (2006.01) | |
| *C07D 498/18* | (2006.01) | |
| *A61K 31/4439* | (2006.01) | |
| *A61K 31/496* | (2006.01) | |
| *A61K 31/695* | (2006.01) | |
| *C07D 519/00* | (2006.01) | |
| *C07F 7/18* | (2006.01) | |
| *C12N 9/99* | (2006.01) | |
| *A61K 31/5365* | (2006.01) | |
| *A61K 31/55* | (2006.01) | |

(52) U.S. Cl.
CPC ........ *A61K 31/4439* (2013.01); *A61K 31/496* (2013.01); *A61K 31/537* (2013.01); *A61K 31/5365* (2013.01); *A61K 31/55* (2013.01); *A61K 31/695* (2013.01); *A61K 45/06* (2013.01); *C07D 491/18* (2013.01); *C07D 498/18* (2013.01); *C07D 519/00* (2013.01); *C07F 7/1856* (2013.01); *C12N 9/99* (2013.01)

(58) Field of Classification Search
CPC .... A61K 31/537; A61K 31/55; A61K 31/695; A61K 45/06; C07D 491/18; C07D 498/18; C07D 519/00; C07F 7/1856; C12N 9/99
See application file for complete search history.

(56) References Cited

OTHER PUBLICATIONS

Written Opinion and International Search Report, dated Mar. 26, 2015.
Li et al. "Unexpected ring contraction and oxidation rearrangement reactions of securinine", Tetrahedron, 2012, vol. 68, pp. 3972-3979. p. 3976, Table 2, compound 10; p. 3975, scheme 4;p. 3978, col. 1, para 2-5.

* cited by examiner

X = C, C-C, C=C, C≡C
R=alkyl, alkenyl, alkynyl, heteroatom, etc.,       and or

SMALL MOLECULE SECURININE AND NORSECURININE ANALOGS AND THEIR USE IN CANCERS, INFLAMMATORY DISEASES AND INFECTIONS

RELATED APPLICATIONS

This application claims priority to U.S. Provisional Application No. 61/886,448, filed Oct. 3, 2013, to U.S. Provisional Patent Application 61/942,880, filed Feb. 21, 2014 and to U.S. Provisional Patent Application 62/051,595, filed Sep. 17, 2014, all of which are hereby incorporated by reference in their entirety.

FIELD OF THE INVENTION

The application relates to the synthesis of small molecule compounds derived from securinine and norsecurinine and demonstrates the effectiveness of the compounds in regulating various cellular signaling pathways and their utility for cancer, inflammatory diseases and infectious diseases.

BACKGROUND

Securinine ($C_{13}H_{15}NO_2$; mw 217.2637; also known as CHEMBL303062; Securinin; Securinan-11-one; 5610·40·2; Securinine, (−)-; UNII-G4VS580P5E; NSC107413, as well as stereoisomers virosecurinine and allosecurinine) is a small molecule with the recognized two-dimensional structure:

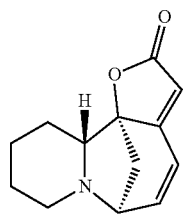 [SMILES: O=C1C=C2C=C[C@@H]3C[C@@]2(O1)[C@H]1CCCCN31]

Securinine is a plant-derived alkaloid that has previously demonstrated efficacy for neurological related diseases. An unexpected rearranged derivative, norsecurinine, has recently been reported (Li et al., Tetrahedron 2012, 68, 3972-3979):

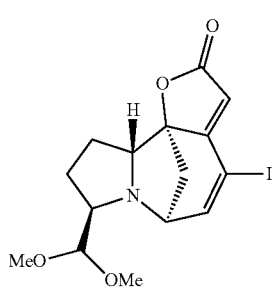

INVS-MG-52B

As well as a brominated derivative:

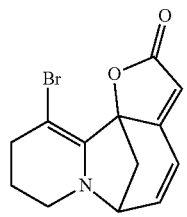 [SMILES: O=C1C=C2C=CC3CC2(O1)C1=C(Br)CCCN13]

Securinine is documented as an effective $GABA_A$ receptor antagonist with otherwise very low cellular toxicity (Beutler et al., Brain Res 330(1); 135-140, 1985; Lubick et al., J Leukoc Biol. 2007 November; 82(5):1062-9). Securinine has further been identified to induce apoptosis of promyelocytic leukemia cells and colon cancer cells at high doses and to induce monocytic differentiation of a wide range of myeloid leukemia cell lines as well as primary leukemic patient samples at low doses (Rana et al., 2010, The FASEB Journal, 24(6) 2126-2134; Dong et al., Zhongguo yao li xue bao=Acta pharmacologica Sinica 20.3 (1999): 267-270; Gupta et al., PLoS ONE 6(6): e21203. doi:10.1371./journal.pone.0021203, 2011). Securinine has also been found to lead to cell killing of other cancer cell types such as breast cancer. (Li et al., Pharmazie 69: 217-23 (2014). Additional studies have focused on adapted structures derived from synthesizing the securinine molecule and noted its potential for a wide variety of infectious diseases such as parasitic disease. For example, the differences in activity on toxoplasma growth between the various derivatives (Holmes et al. Experimental parasitology 127.2 (2011): 370-375) was investigated. It also has activity against fungi (Sahni et al., Mycobiology 33.2 (2005): 97-103.).

Securinine has also been found to have activity in modulating infectious diseases through its ability to enhance the host immune response. For example, it enhances the ability of macrophages to clear a bacterial infection. (Lubick et al., Journal of leukocyte biology 82.5 (2007): 1062-1069).

Others have identified a natural reductase that reduces the γ,δ double bond of securinine and presented various derivatives of the reduced securinine (with functional groups affixed at C15) that also alter myeloid cell activity (Guan et al., Biotechnology letters 27.16 (2005): 1189-1193; US Published Patent Application 20140018383). Given the apparent diverse cellular activity offered by securinine as a backbone, investigations were aimed at discovering more potent analogs and identifying new cellular targets of pathological diseases that analogs may interact with.

SUMMARY OF THE INVENTION

The present invention provides for securinine analogs comprising the structure of

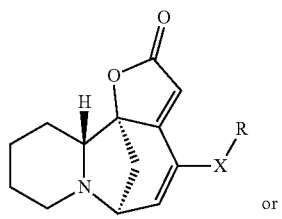

or

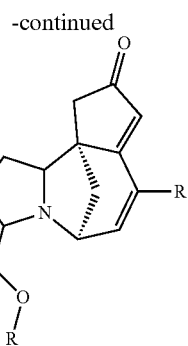

wherein X is a C, C—C, C=C or C≡C and R is a substituted or unsubstituted $C_1$-$C_{24}$ alkyl, $C_2$-$C_{24}$ alkenyl, $C_2$-$C_{24}$ alkynyl, $C_3$-$C_{20}$ aryl, hydrogen, halogen, heteroaryl, heterocycloalkenyl containing from 5-6 ring atoms (wherein from 1-3 of the ring atoms is independently selected from N, NH, N($C_1$-$C_5$ alkyl), NC(O)($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof.

The present invention further provides for pharmaceutical compositions comprising the securinine analogs described herein.

The present invention provides for methods of using the securinine analogs, comprising administering one or more of the analogs to a subject or a cell. As set out herein, the securinine analogs inhibit tumor growth and induce cell differentiation and cell death. The methods are accordingly applicable to conditions comprising tumor growth, such as cancers, and improper cell maturation, such as leukemias, colon cancer, and breast cancer.

DESCRIPTION

Figure 1:
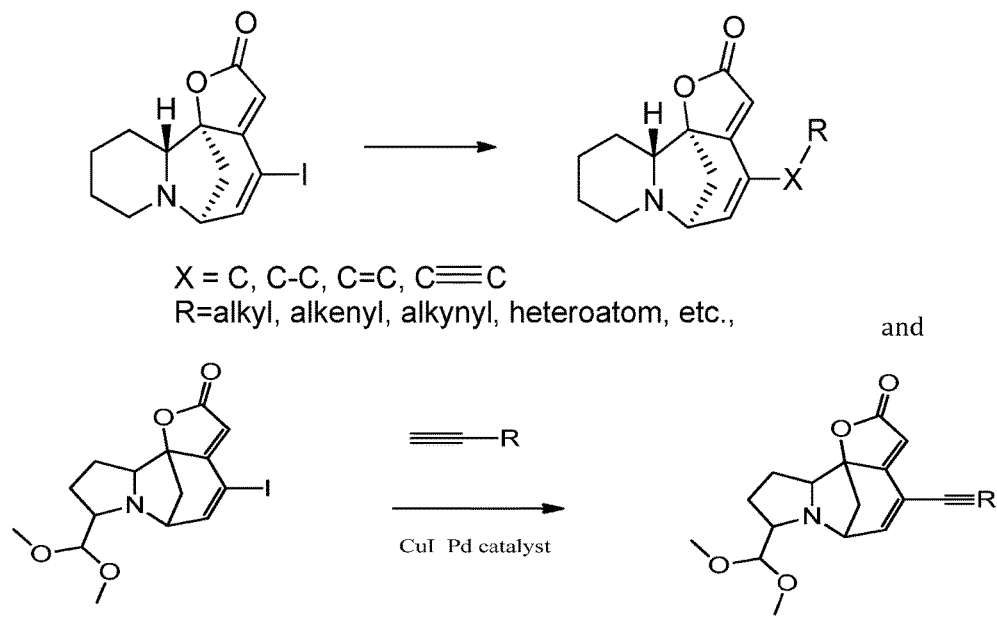
FIG. 1 shows an overview of the synthesis of securinine and norsecurinine analogs.
Figure 2:
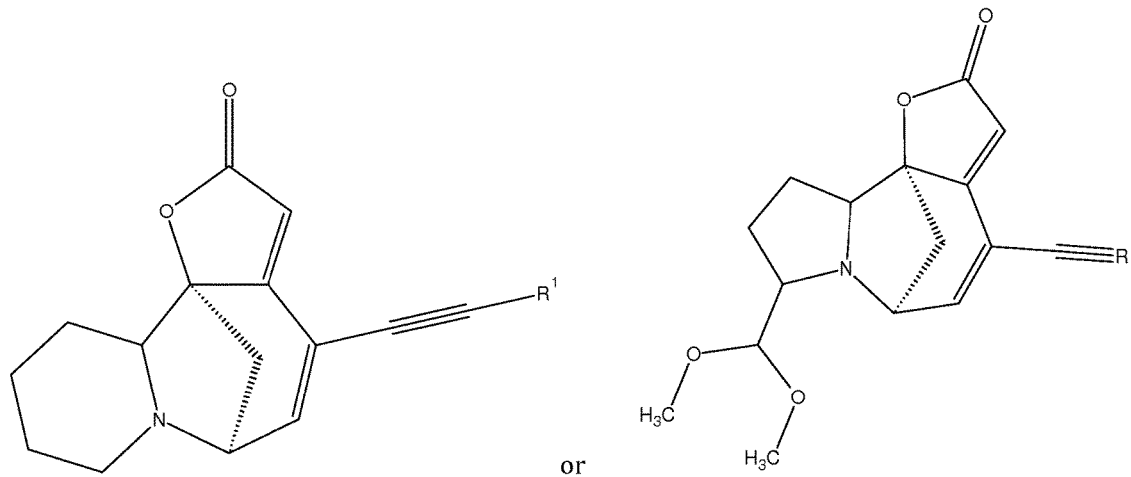
FIG. 2 shows an overview of the basic structure of securinine and norsecurinine analogs.

The present invention provides for securinine and norsecurinine derived small molecules, namely synthetic analogs of securinine and norsecurinine. The present invention in part provides for a non-reduced γ,δ double bond of securinine with functional groups attached at C14, based on the following numbering:

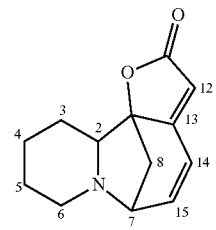 [SMILES: O=C1C=C2C=CC3CC2(O1)C1CCCCN31]

The present invention also provides for further analogs derived from the norsecurinine isomer with a non-reduced γ,δ double bond with functional groups attached at C14. The present invention also provides for compounds with a reduced γ,δ double bond of securinine and norsecurinine and functional groups attached at the C14 and/or C15.

The present invention provides for securinine and norsecurinine derived compounds of the following formula:

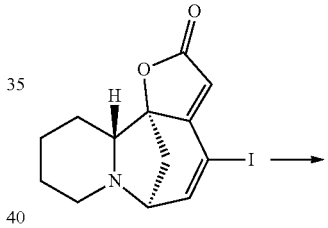

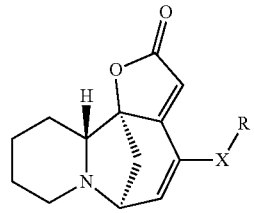

X=C, C—C, C=C, C≡C

R=alkyl, alkenyl, alkynyl, heteroatom, etc., and

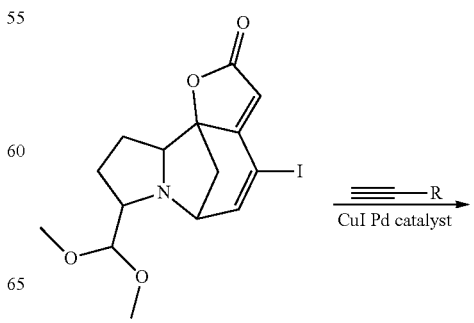

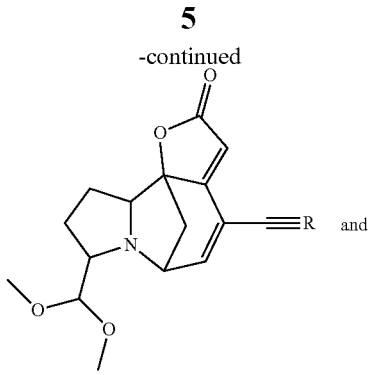

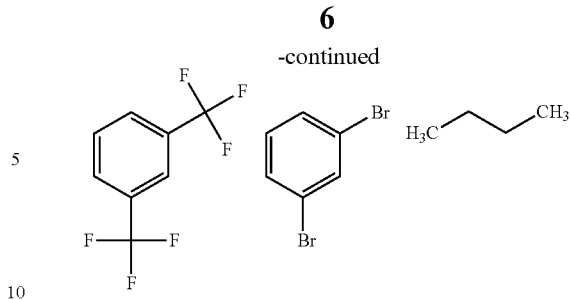

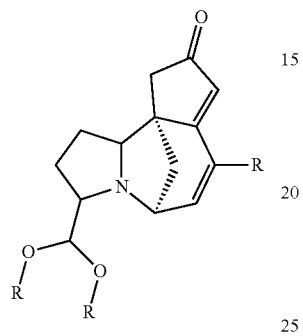

The present invention provides for small molecule alkynyl analogues of securinine and norsecurinine of the following formula:

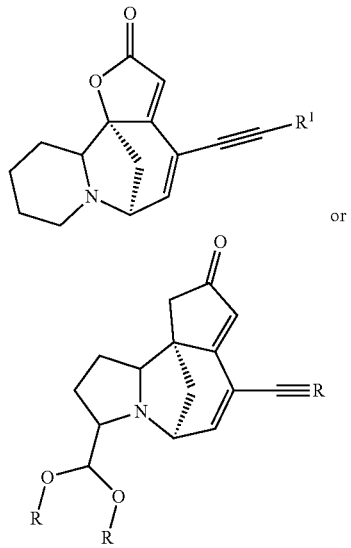

wherein X is a C, C—C, C=C or C≡C and R is a substituted or unsubstituted $C_1$-$C_{24}$ alkyl, $C_2$-$C_{24}$ alkenyl, $C_2$-$C_{24}$ alkynyl, $C_3$-$C_{20}$ aryl, hydrogen, halogen, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_5$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof and pharmaceutically acceptable salts thereof. By way of example, R may include the following structures:

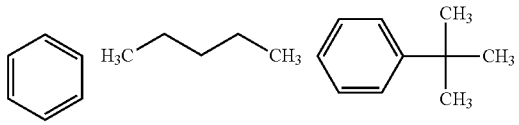

wherein R or R1 is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, hydrogen, halogen, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl) oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof and pharmaceutically acceptable salts thereof. By way of example, R and R1 may include the following structures:

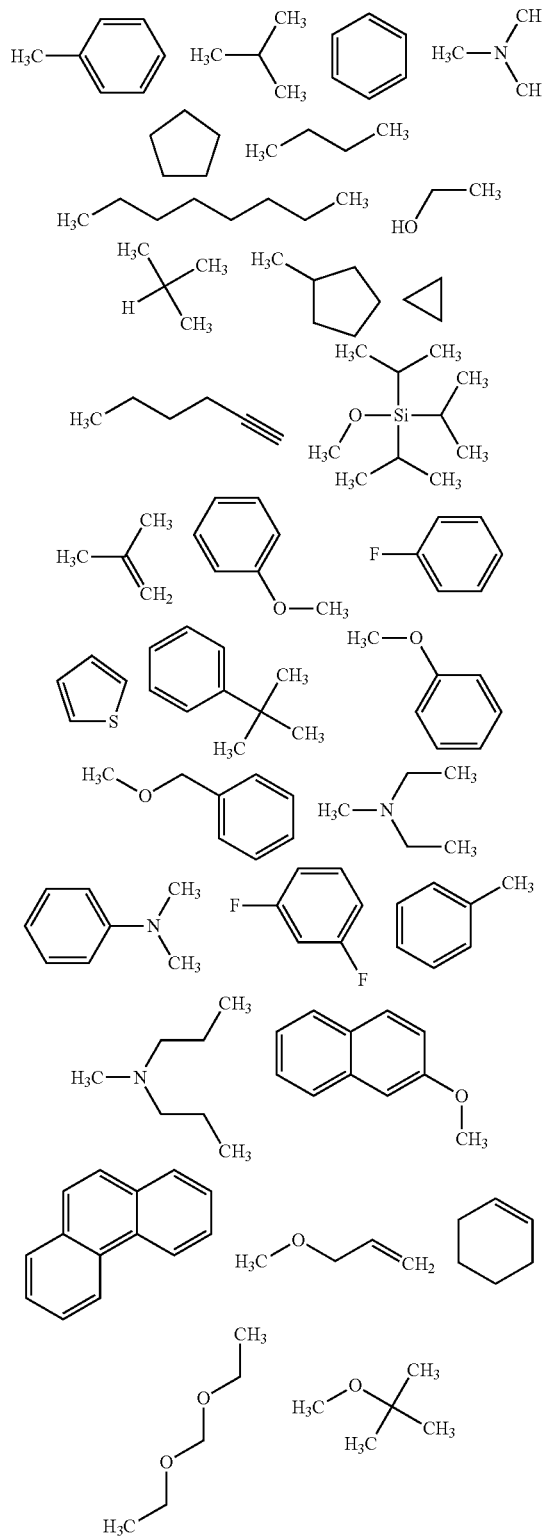

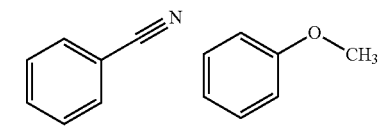

-continued

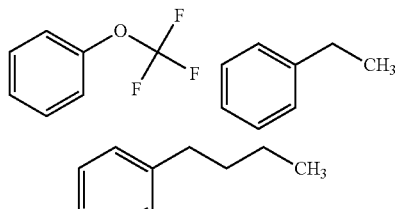

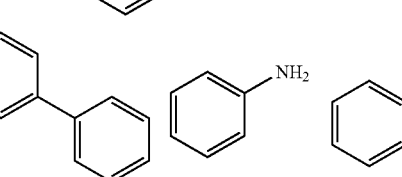

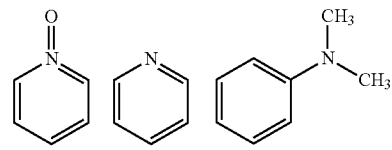

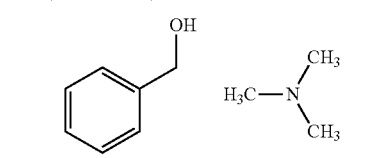

The present invention provides for securinine and norsecurinine analogs with a functional group affixed at C14 and a non-reduced γ,δ double bond. The γ-iodo derivative of securinine (C14-iodo derivative of securinine, INVS-MG-52A) can be prepared from securinine using N-iodosuccinimide in MeOH (see, Li et al, *Tetrahedron* 2012, 68, 3972-3979):

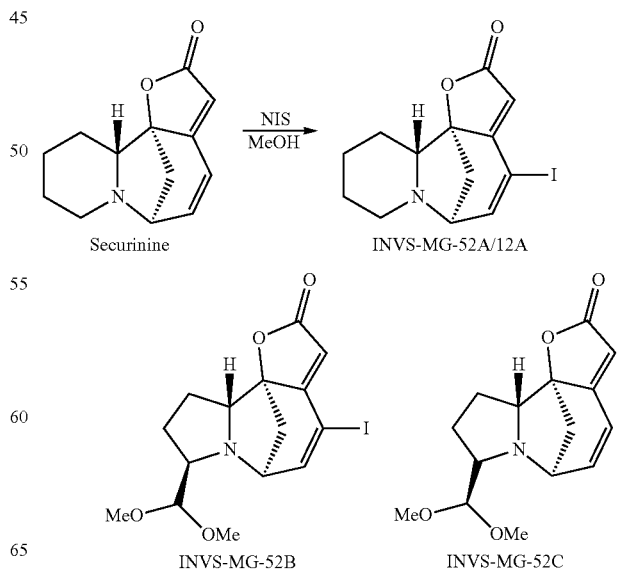

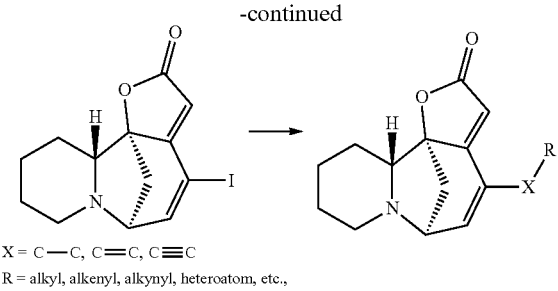

X = C—C, C=C, C≡C
R = alkyl, alkenyl, alkynyl, heteroatom, etc.,

During the product isolation from the reaction mixture, side products INVS-MG-52B and INVS-MG-52D may also be isolated. The intermediates INVS-MG-52A and INVS-MG-52B can then be adapted to prepare further C-14 analogs of securinine. Those skilled in the art will appreciate that the analogs described herein can further be obtained through modifications to the synthetic pathways as those described herein.

An example of the synthesis of C-14 alkyl/aryl analogs of securinine can be prepared using INVS-MG-52A and the corresponding boronic acids/esters as follows:

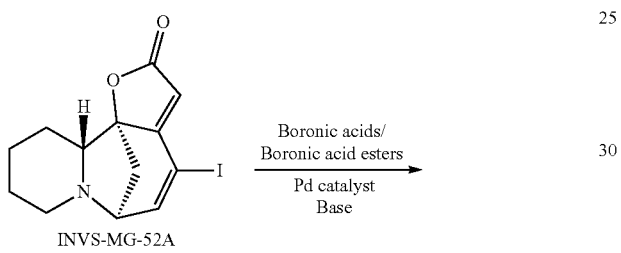

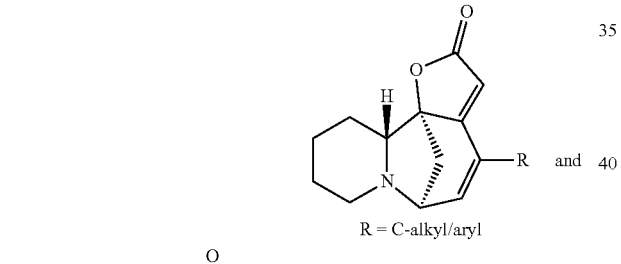

R = C-alkyl/aryl and

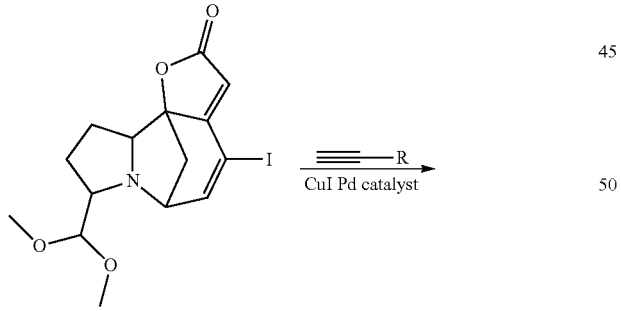

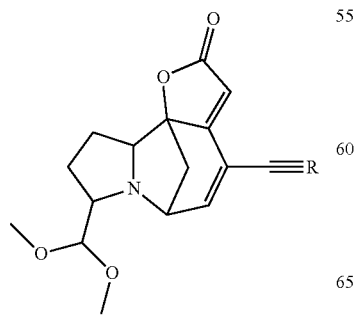

By way of example, and not by way of limitation, bis(triphenylphosphine)palladium(II)dichloride can be added to a solution comprising INVS-MG-52A or INVS-MG-52B in a solvent, such as anhydrous toluene or tetrahydrofuran, followed by adding the corresponding boronic acid and potassium carbonate/water. The reaction mixture can then be degassed under nitrogen atmosphere and then heated to 80° C. to 100° C. The reaction mixture may then be extracted, dried and concentrated. The crude product can be purified by chromatography using an appropriate solvent system to afford the desired C-14 alkyl/aryl analog of securinine in 40-70% yield. The following C-14 alkyl/aryl analogs of securinine have been synthesized employing the above:

INVS-MG-56A

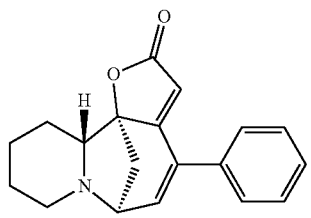

INVS-MG-54B

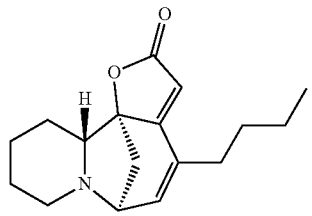

INVS-MG-63B

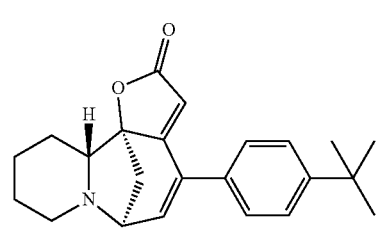

INVS-MG-64A

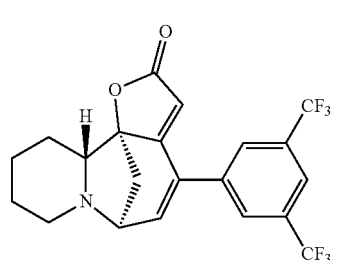

INVS-MG-65B

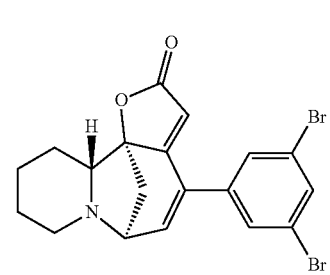

The process comprising the synthesis of C-14 alkynyl analogs of securinine and norsecurinine can be prepared using INVS-MG-52A or INVS-MG-52B and the corresponding terminal alkynes as outlined below.

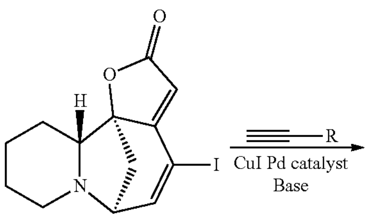

INVS-MG-52A 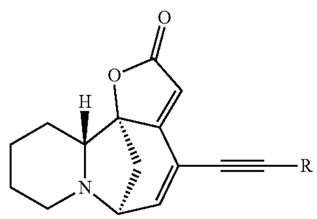 and

R = C-alkynyl 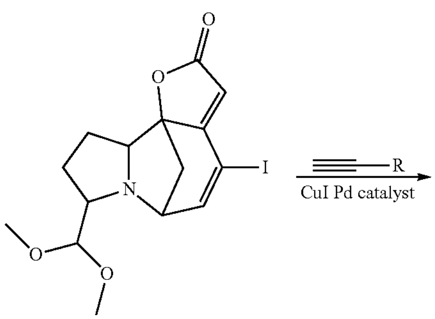 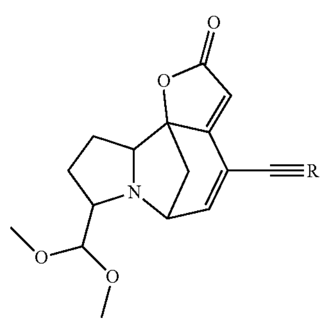 wherein R=alkyl, aryl or vinylic.

By way of further example, to a solution of INVS-MG-52A or INVS-MG-52B in anhydrous 1,4-dioxane/tetrahydrofuran may be added bis(triphenylphosphine)palladium (II)dichloride, copper (I) iodide and tryethylamine. The reaction mixture can be then degassed under nitrogen atmosphere and then gradually heated to 80° C. Heat can then be removed to bring the reaction mixture to room temperature, and the corresponding alkyne added. The reaction mixture can then be poured in water and extracted, such as with ethylacetate, and then dried and concentrated. The following C-14 alkynyl analogs of securinine have been synthesized employing the above procedure:

INVS-MG-108B

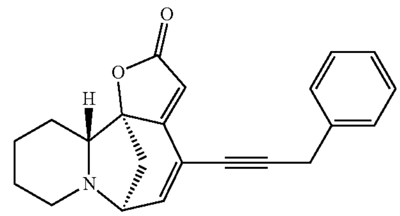

INVS-MG-109-IIA

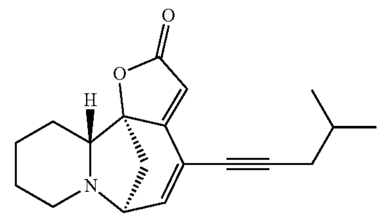

INVS-MG-110B

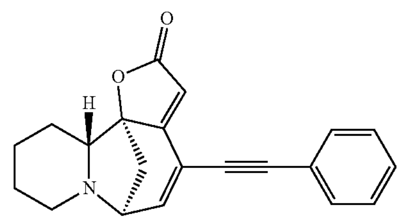

INVS-MG-111B

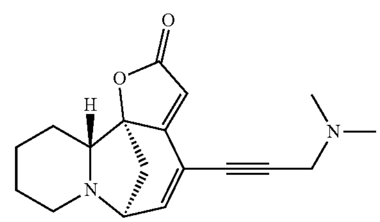

INVS-MG-113A

INVS-MG-117B

INVS-MG-118B

INVS-MG-120A
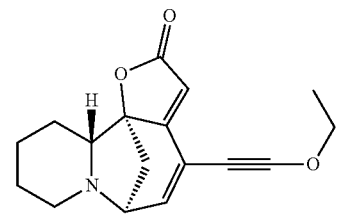
INVS-MG-121A
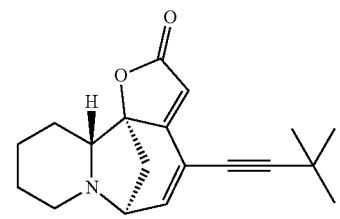
INVS-MG-123B
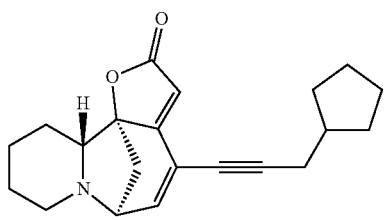
INVS-MG-124A
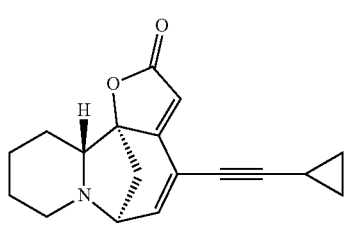
INVS-MG-125A
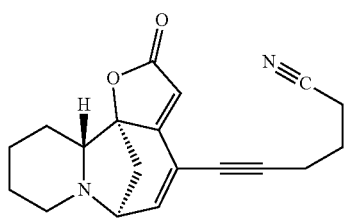
INVS-MG-131A
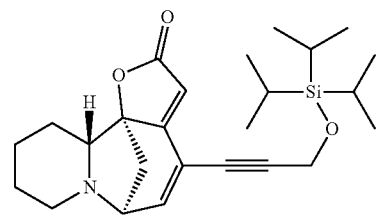
INVS-MG-132A
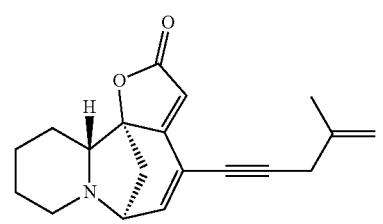
INVS-MG-134C
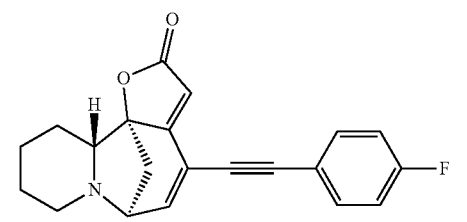
INVS-MG-135B
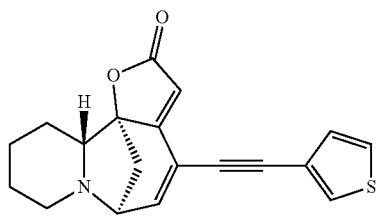
INVS-MG-136B
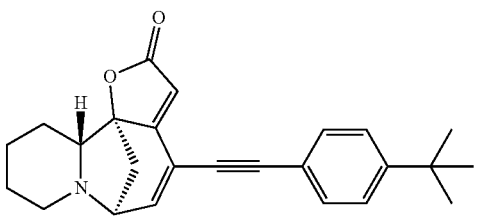
INVS-MG-133B
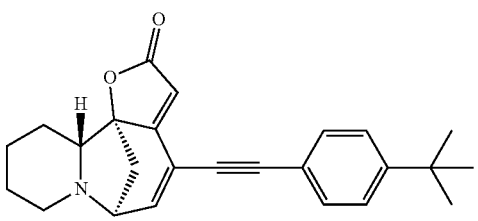
INVS-MG-133B
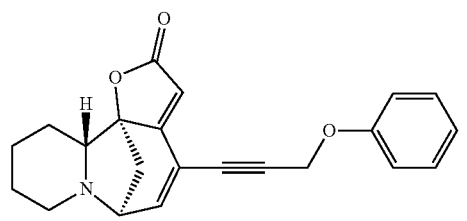
INVS-MG-137B INVS-MG-138B
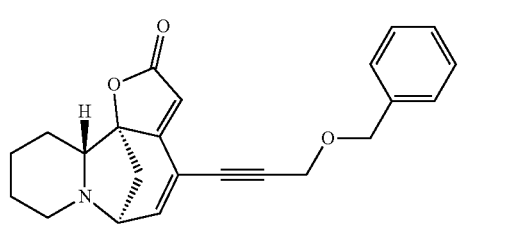
INVS-MG-157B
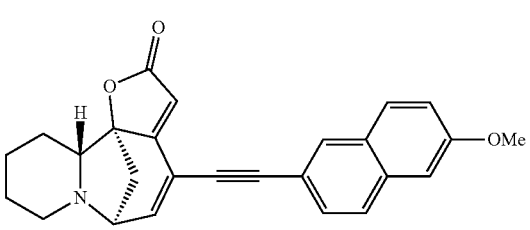
INVS-MG-145A
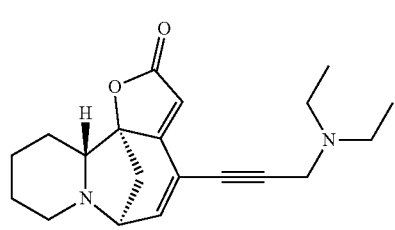
INVS-MG-158B
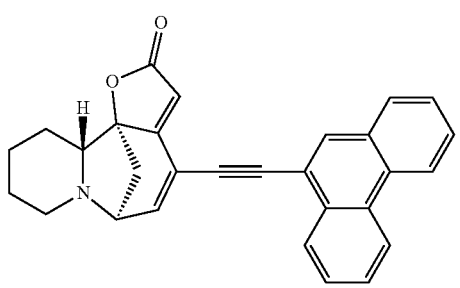
INVS-MG-146B
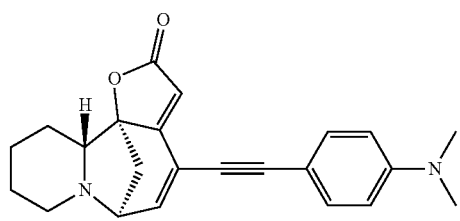
INVS-MG-159A
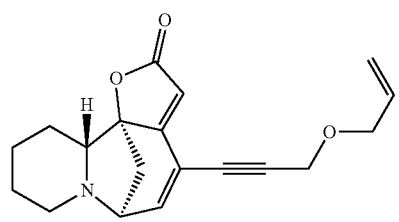
INVS-MG-150B
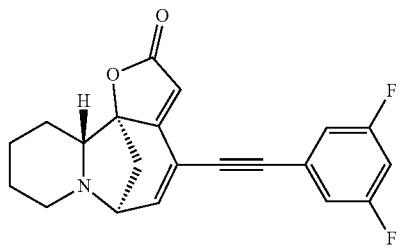
INVS-MG-160B
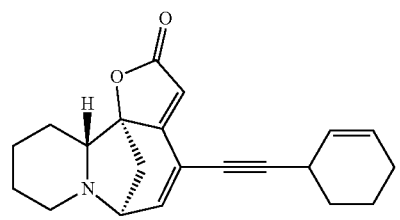
INVS-MG-151B
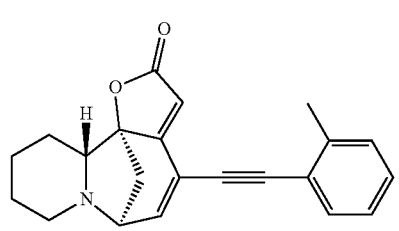
INVS-MG-161B
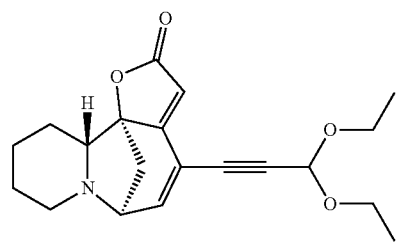
INVS-MG-152A
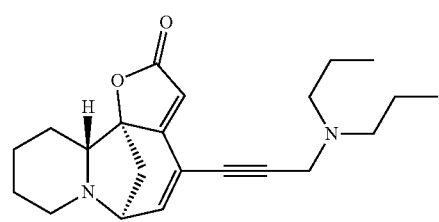
INVS-MG-162B
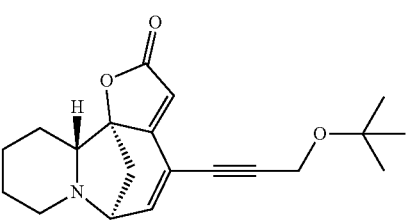

INVS-MG-164B
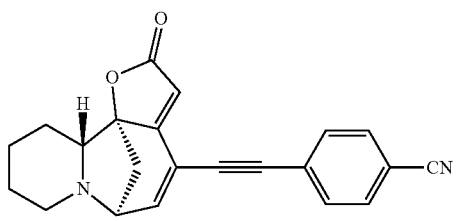

INVS-MG-165B
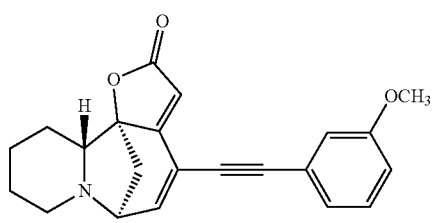

INVS-MG-166B
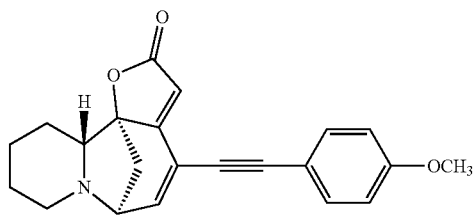

INVS-MG-167B
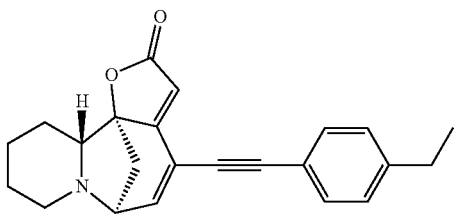

INVS-MG-168B
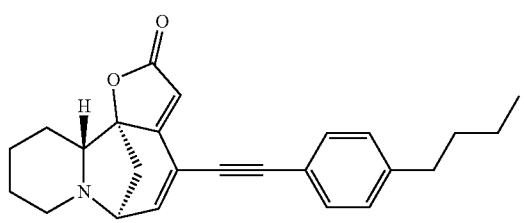

INVS-MG-169B
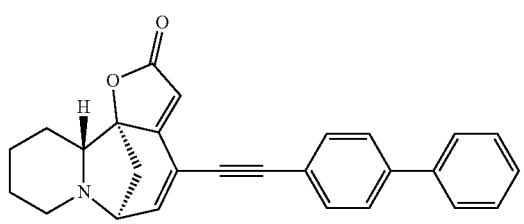

INVS-MG-170B
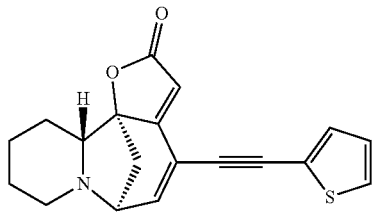

INVS-MG-175A
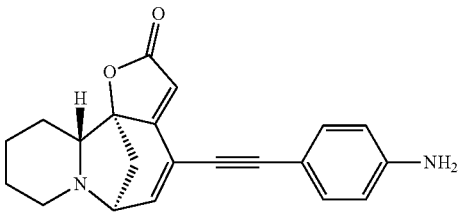

INVS-MG-193B
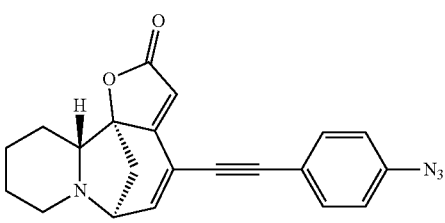

In another variation, the process comprising the synthesis of various pharmaceutically useful salts can be prepared as follows: a securinine or norsecurinine analog may be dissolved in 1,4-dioxane added to a 2N HCl/1,4-dioxane solution mixture at 0° C. The reaction mixture may be stirred as the product slowly precipitates. Hexanes or ether can then be added and the solids then filtered and washed to obtain the corresponding HCl salts. Similarly, a securinine analog can be dissolved in methanol and tartaric acid then added. The reaction mixture can be gradually heated to 80° C. as the product slowly precipitates. Ether can then be added and the solids filtered and washed to obtain the corresponding tartarate salts. Further still, securinine or norsecurinine analogs may be dissolved in methanol with tartaric acid added. The reaction mixture may be heated to 80° C. and product allowed to precipitate. Ether may then be added and the solids filtered and washed to obtain the corresponding tartarate salts. The following various pharmaceutically useful salts of securinine analogs have been thusly prepared, isolated and identified:

INVS-MG-70
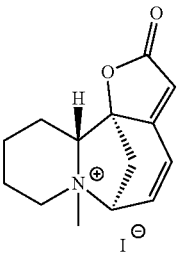

INVS-MG-72
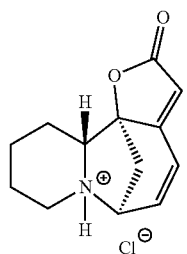
INVS-MG-83
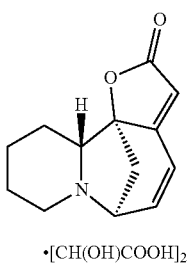
•[CH(OH)COOH]₂
INVS-MG-71
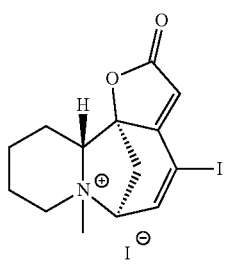
INVS-MG-73
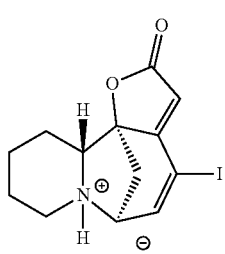
INVS-MG-84
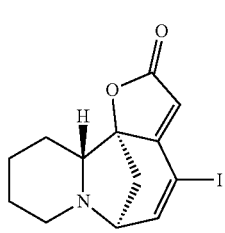
•[CH(OH)COOH]₂
INVS-MG-111-IV
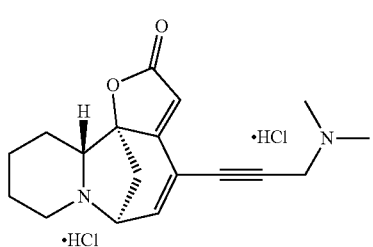
INVS-MG-125-III
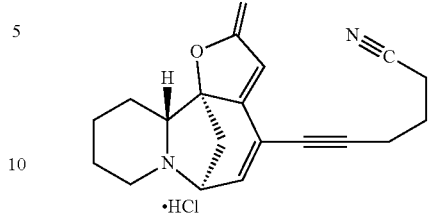
INVS-MG-157-III
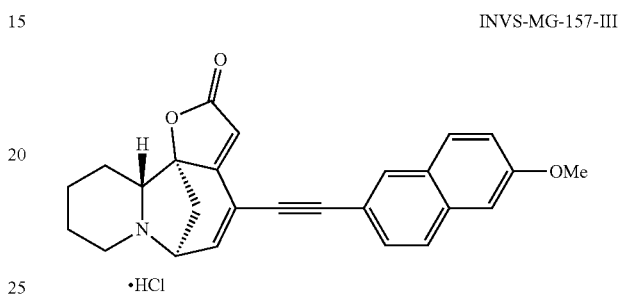
INVS-MG-158-III
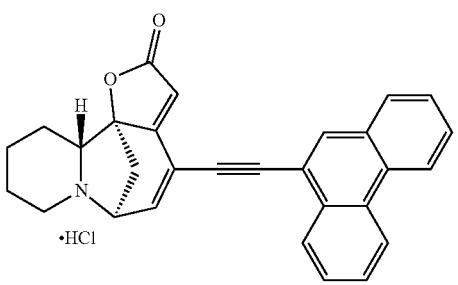
INVS-MG-169-III
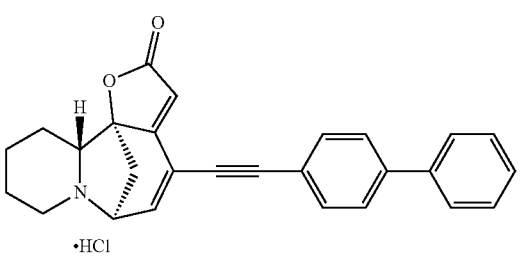
INVS-MG-170-III INVS-MG-146-III
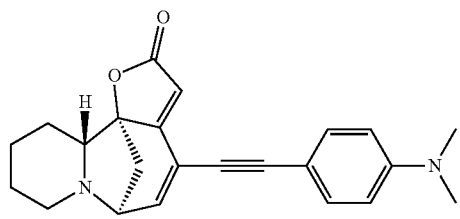
•2HCl
INVS-MG-152-III
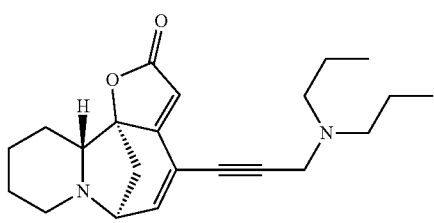
•2HCl
INVS-MG-175-V
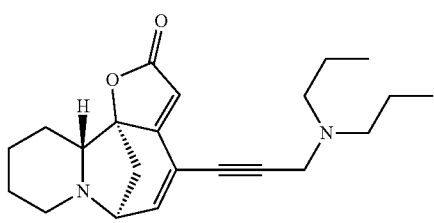
•2HCl
INVS-MG-193-III
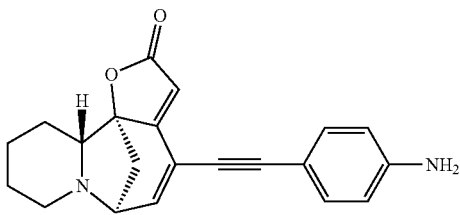
•HCl
INV-SZ-113-2
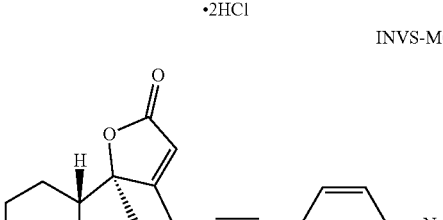
INV-SZ-114-1
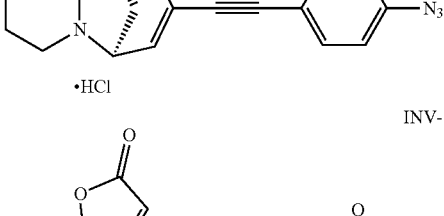
INV-SZ-115-1
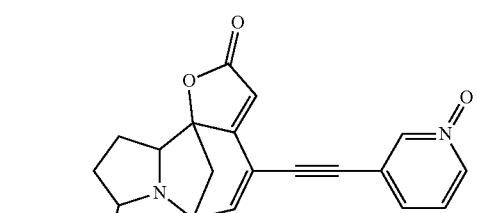
INV-SZ-116-1
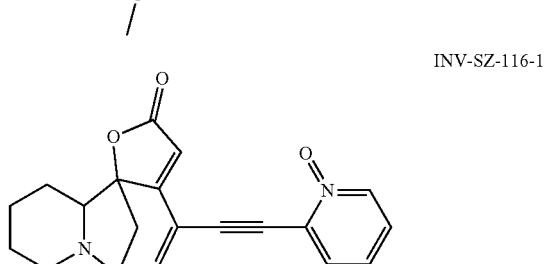
INV-SZ-117-3
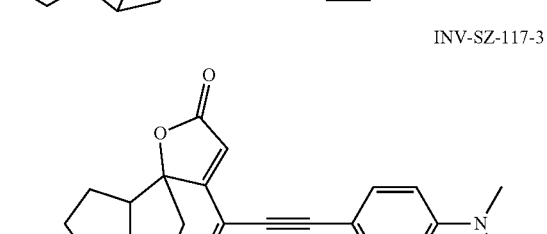
INV-SZ-118-2
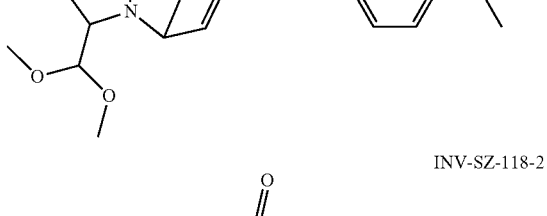
INV-SZ-120-1
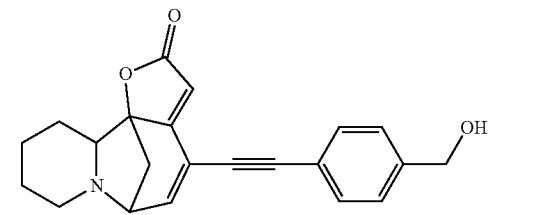
INV-SZ-121-1
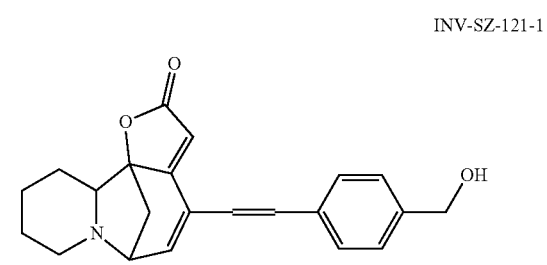

INV-SZ-122-1
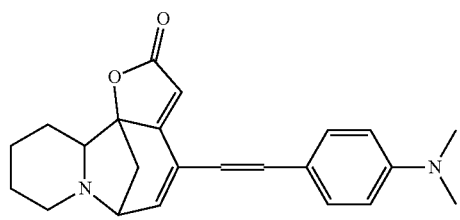
INV-SZ-123-2
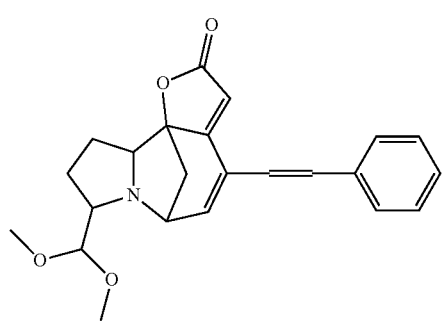
INV-SZ-123-3
INV-SZ-125-1
INV-SZ-125-2
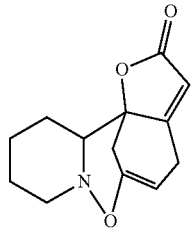
INV-SZ-125-3
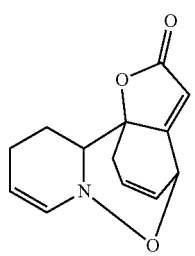
INV-SZ-127-1
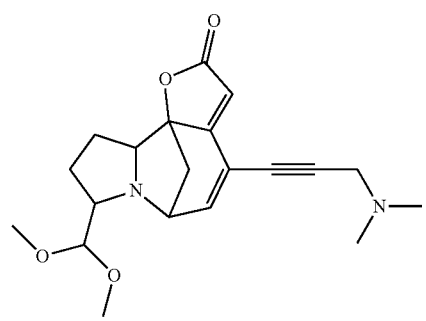
INV-SZ-129-1
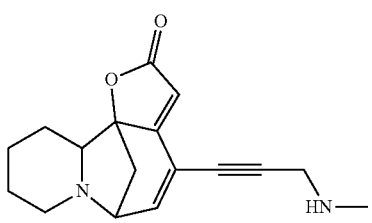
The following list provides an example of securinine and/or norsecurinine analogs produced by the methods described herein:
| Sample Code | Structure |
| --- | --- |
| Securinine | 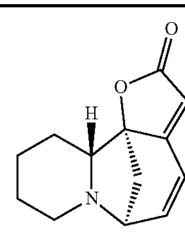 |

-continued

| Sample Code | Structure |
|---|---|
| INV-2B (INVS-MG-34B) | 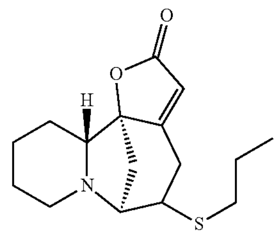 [SMILES: CCCSC1CC2=CC(=O)O[C@@]23C[C@@H]1N1CCCC[C@@H]13] |
| INV-26C/ INVS-MG-37B/ Sec-7/Sec-22 | 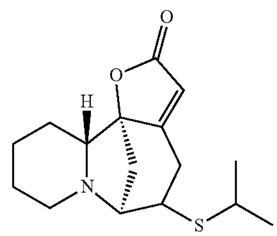 [SMILES: CC(C)SC1CC2=CC(=O)O[C@@]23C[C@@H]1N1CCCC[C@@H]13] |
| INVS-MG-3B | 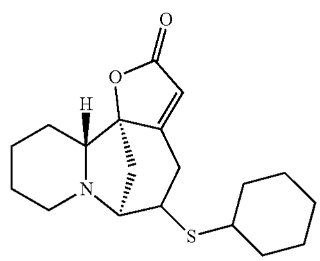 [SMILES: O=C1C=C2CC(SC3CCCCC3)[C@@H]3C[C@@]2(O1)[C@H]1CCCCN31] |
| INVS-MG-4B | 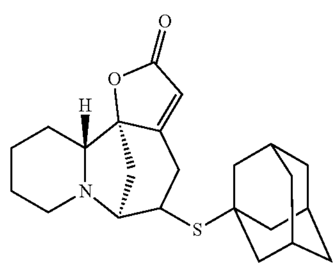 [SMILES: O=C1C=C2CC(SC34CC5CC(CC(C5)C3)C4)[C@@H]3C[C@@]2(O1)[C@H]1CCCCN31] |
| INVS-MG-7C | 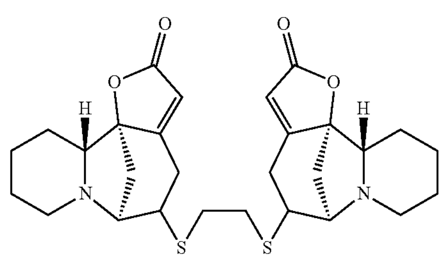 [SMILES: O=C1C=C2CC(SCCSC3CC4=CC(=O)O[C@]45C[C@H]3N3CCCC[C@H]35)[C@@H]3C[C@@]2(O1)[C@H]1CCCCN31] |
| INVS-MG-9A | 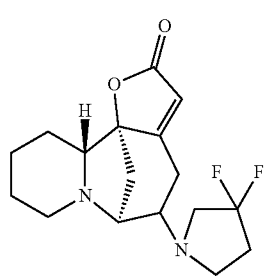 [SMILES: O=C1C=C2CC(N3CCC(F)(F)C3)[C@@H]3C[C@@]2(O1)[C@H]1CCCCN31] |

-continued

| Sample Code | Structure |
|---|---|
| INVS-MG-12A | 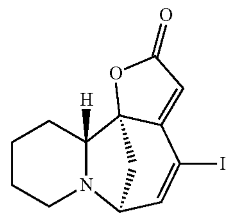 [SMILES: O=C1C=C2C(I)=C[C@@H]3C[C@@]2(O1)[C@H]1CCCCN31] |
| INVS-MG-14B | 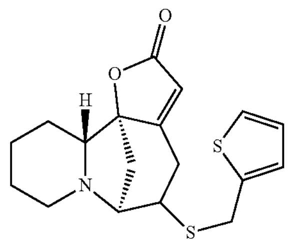 [SMILES: O=C1C=C2CC(SCc3cccs3)[C@@H]3C[C@@]2(O1)[C@H]1CCCCN31] |
| INVS-MG-16A | 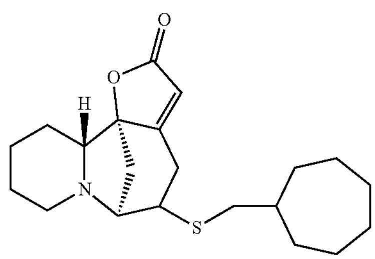 [SMILES: O=C1C=C2CC(SCC3CCCCCC3)[C@@H]3C[C@@]2(O1)[C@H]1CCCCN31] |
| INVS-MG-5A | 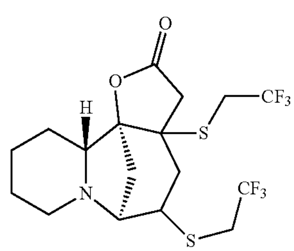 [SMILES: O=C1CC2(SCC(F)(F)F)CC(SCC(F)(F)F)[C@@H]3C[C@@]2(O1)[C@H]1CCCCN31] |
| INVS-MG-26A | 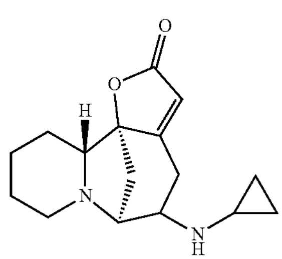 [SMILES: O=C1C=C2CC(NC3CC3)[C@@H]3C[C@@]2(O1)[C@H]1CCCCN31] |
| INVS-MG-27B | 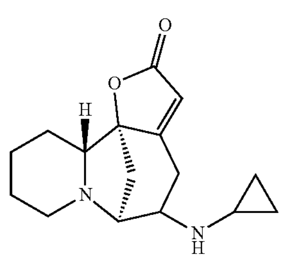 [SMILES: O=C1C=C2CC(NC3CC3)[C@@H]3C[C@@]2(O1)[C@H]1CCCCN31] |

-continued

| Sample Code | Structure |
|---|---|
| INVS-MG-28B | 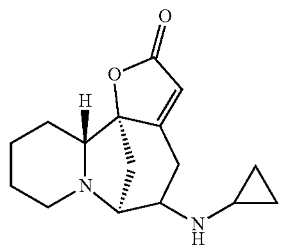 [SMILES: O=C1C=C2CC(NC3CC3)[C@@H]3C[C@@]2(O1)[C@H]1CCCCN31] |
| INVS-MG-29A | 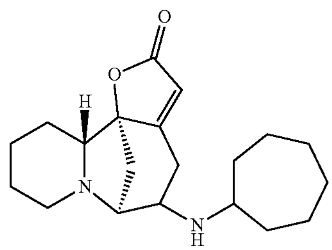 [SMILES: O=C1C=C2CC(NC3CCCCCC3)[C@@H]3C[C@@]2(O1)[C@H]1CCCCN31] |
| INVS-MG-30A | 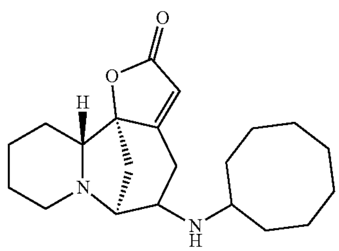 [SMILES: O=C1C=C2CC(NC3CCCCCCC3)[C@@H]3C[C@@]2(O1)[C@H]1CCCCN31] |
| INVS-MG-19A | 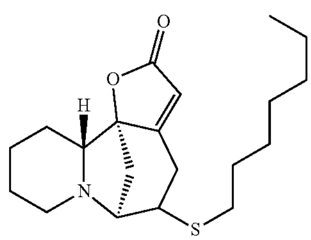 [SMILES: CCCCCCCSC1CC2=CC(=O)O[C@@]23C[C@@H]1N1CCCC[C@@H]13] |
| Sec-1 | 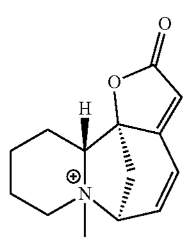 [SMILES: C[N+]12CCCC[C@@H]1[C@]13C[C@H]2C=CC1=CC(=O)O3] |
| INVS-MG-5B | 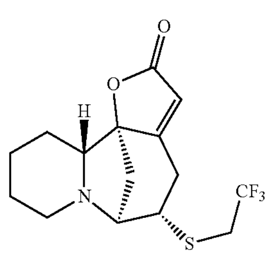 [SMILES: O=C1C=C2C[C@H](SCC(F)(F)F)[C@@H]3C[C@@]2(O1)[C@H]1CCCCN31] |

-continued

| Sample Code | Structure |
|---|---|
| INVS-MG-5C | *(structure with CF₃ group)* |
| Sec-2 | *(structure with OH and benzyl group)* |
| Sec-3 | *(structure with propyl-thio group)* |
| INVS-MG-20B | *(structure with butyl-thio group)* |
| INVS-MG-21B | *(structure with diethylaminoethyl-thio group)* |
| Sec-4 | *(structure with hydroxybenzyl group, ·HCl)* |

-continued

| Sample Code | Structure |
|---|---|
| Sec-5 | (structure) |
| Sec-6 | (structure) |
| Sec-8 | (structure) |
| Sec-9 | (structure) |
| Sec-11 | (structure) |
| Sec-12 | (structure) |

-continued

| Sample Code | Structure |
|---|---|
| Sec-13 | 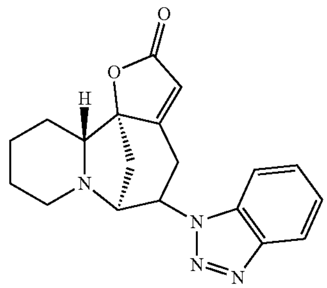 [SMILES: O=C1C=C2CC(n3nnc4ccccc43)[C@@H]3C[C@@]2(O1)[C@H]1CCCCN31] |
| Sec-15 | 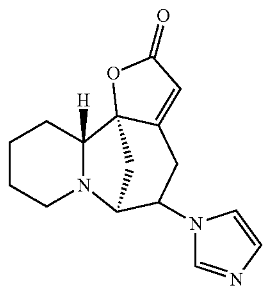 [SMILES: O=C1C=C2CC(n3ccnc3)[C@@H]3C[C@@]2(O1)[C@H]1CCCCN31] |
| Sec-16 | 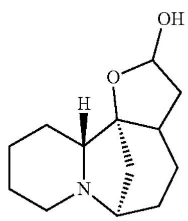 [SMILES: OC1CC2CC[C@@H]3C[C@@]2(O1)[C@H]1CCCCN31] |
| Sec-17 | 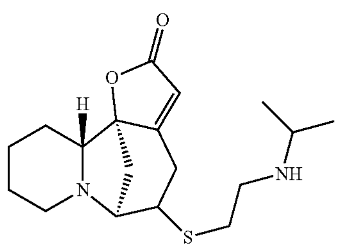 [SMILES: CC(C)NCCSC1CC2=CC(=O)O[C@@]23C[C@@H]1N1CCCC[C@@H]13] |
| Sec-18/20 | 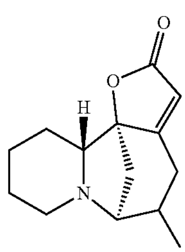 [SMILES: CC1CC2=CC(=O)O[C@@]23C[C@@H]1N1CCCC[C@@H]13] |
| Sec-23 | 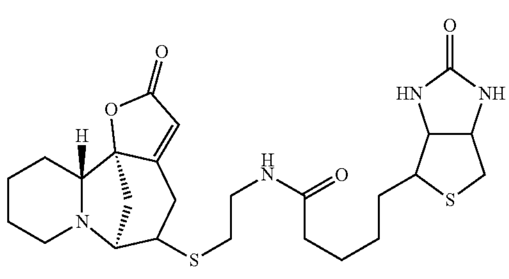 [SMILES: O=C(CCCCC1SCC2NC(=O)NC21)NCCSC1CC2=CC(=O)O[C@@]23C[C@@H]1N1CCCC[C@@H]13] |

-continued

| Sample Code | Structure |
|---|---|
| INVS-MG-46B | 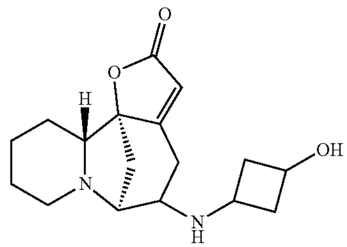 [SMILES: O=C1C=C2CC(NC3CC(O)C3)[C@@H]3C[C@@]2(O1)[C@H]1CCCCN31] |
| INVG-27-2/ INVS-MG-52B | 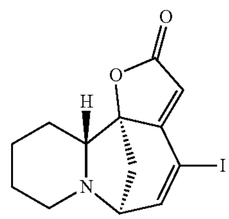 [SMILES: O=C1C=C2C(I)=C[C@@H]3C[C@@]2(O1)[C@H]1CCCCN31] |
| INVG-Z-27-4/ INVS-MG-52D | 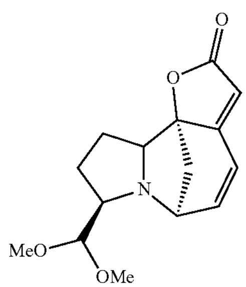 [SMILES: COC(OC)[C@H]1CCC2N1[C@@H]1C=CC3=CC(=O)O[C@@]32C1] |
| INVG-28-1/ INVS-MG-56B | 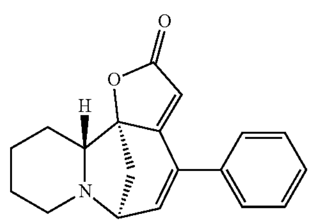 [SMILES: O=C1C=C2C(c3ccccc3)=C[C@@H]3C[C@@]2(O1)[C@H]1CCCCN31] |
| INVS-MG-54B | 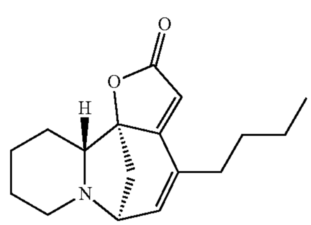 [SMILES: CCCCC1=C[C@@H]2C[C@@]3(OC(=O)C=C13)[C@H]1CCCCN21] |
| INVS MG-25-B | 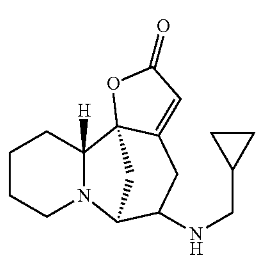 [SMILES: O=C1C=C2CC(NCC3CC3)[C@@H]3C[C@@]2(O1)[C@H]1CCCCN31] |

-continued
| Sample Code | Structure |
|---|---|
| INVS-MG-57A | 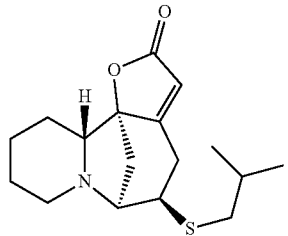 [SMILES: CC(C)CS[C@@H]1CC2=CC(=O)O[C@@]23C[C@@H]1N1CCCC[C@@H]13] |
| INVS-MG-55B/57B | 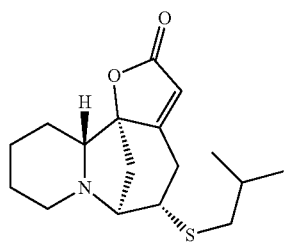 [SMILES: CC(C)CS[C@H]1CC2=CC(=O)O[C@@]23C[C@@H]1N1CCCC[C@@H]13] |
| INVS-MG-58C/34B | 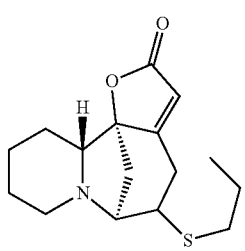 [SMILES: CCCSC1CC2=CC(=O)O[C@@]23C[C@@H]1N1CCCC[C@@H]13] |
| INVS-MG-63B | 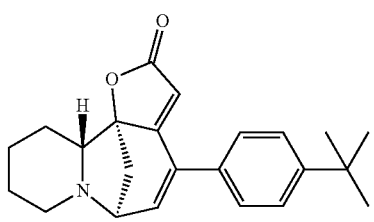 [SMILES: CC(C)(C)c1ccc(C2=C[C@@H]3C[C@@]4(OC(=O)C=C24)[C@H]2CCCCN32)cc1] |
| INVS-MG-64A | 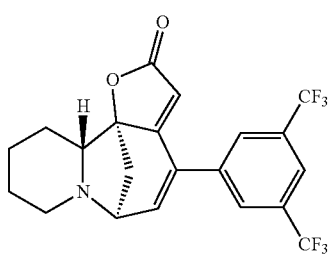 [SMILES: O=C1C=C2C(c3cc(C(F)(F)F)cc(C(F)(F)F)c3)=C[C@@H]3C[C@@]2(O1)[C@H]1CCCCN31] |
| Sec-19 | 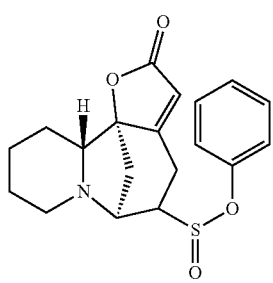 [SMILES: O=C1C=C2CC(S(=O)Oc3ccccc3)[C@@H]3C[C@@]2(O1)[C@H]1CCCCN31] |

-continued

| Sample Code | Structure |
|---|---|
| Sec-21 | 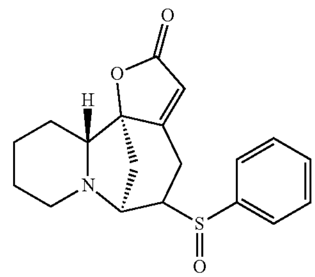 [SMILES: O=C1C=C2CC(S(=O)c3ccccc3)[C@@H]3C[C@@]2(O1)[C@H]1CCCCN31] |
| INVS-MG-65B | 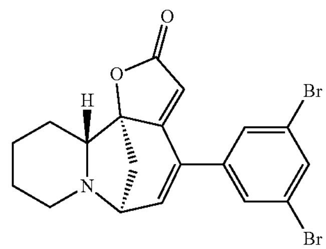 [SMILES: O=C1C=C2C(c3cc(Br)cc(Br)c3)=C[C@@H]3C[C@@]2(O1)[C@H]1CCCCN31] |
| INVS-MG-70 | 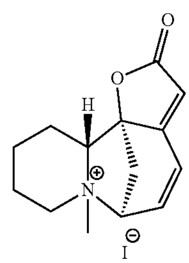 [SMILES: C[N+]12CCCC[C@@H]1[C@]13C[C@H]2C=CC1=CC(=O)O3 ; [I-]] |
| INVS-MG-71 | 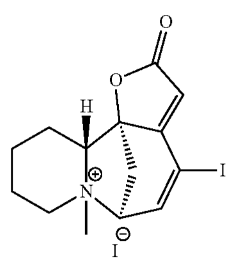 [SMILES: C[N+]12CCCC[C@@H]1[C@]13C[C@H]2C=C(I)C1=CC(=O)O3 ; [I-]] |
| INVS-MG-72/12A | 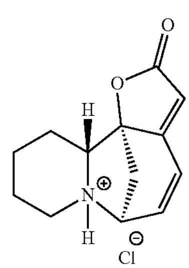 [SMILES: O=C1C=C2C=C[C@@H]3C[C@@]2(O1)[C@H]1CCCC[NH+]31 ; [Cl-]] |
| INVS-MG-59/ Sec-22/INV-26C | 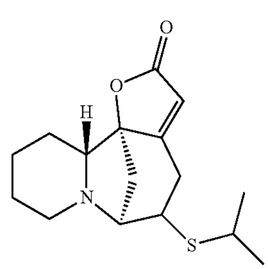 [SMILES: CC(C)SC1CC2=CC(=O)O[C@@]23C[C@@H]1N1CCCC[C@@H]13] |

-continued

| Sample Code | Structure |
|---|---|
| INVS-MG-60 | (structure) |
| INVS-MG-66B | (structure) |
| INVS-MG-82/12A HCl salt | (structure) |
| INVS-MG-83 | (structure) [CH(OH)COOH]$_2$ |
| INVS-MG-84 | (structure) [CH(OH)COOH]$_2$ |
| INVS-MG-44 | (structure) |

-continued
| Sample Code | Structure |
|---|---|
| INVS-MG-86B | 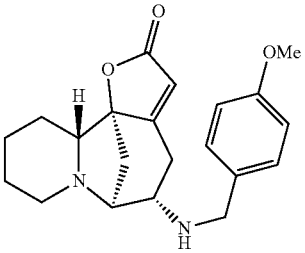 [SMILES: COc1ccc(CN[C@H]2CC3=CC(=O)O[C@@]34C[C@@H]2N2CCCC[C@@H]24)cc1] |
| INVS-MG-94 | 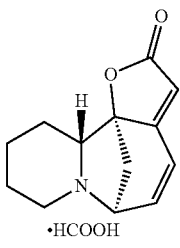 [SMILES: O=C1C=C2C=C[C@@H]3C[C@@]2(O1)[C@H]1CCCCN31 ; "·HCOOH"] |
| INVS-MG-97 IIB | 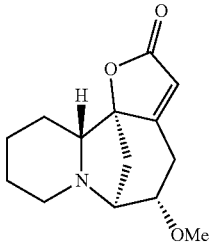 [SMILES: CO[C@H]1CC2=CC(=O)O[C@@]23C[C@@H]1N1CCCC[C@@H]13] |
| INVS-MG-97 IIE | 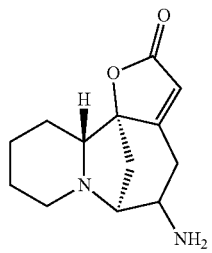 [SMILES: NC1CC2=CC(=O)O[C@@]23C[C@@H]1N1CCCC[C@@H]13] |
| INVS-MG-74A | 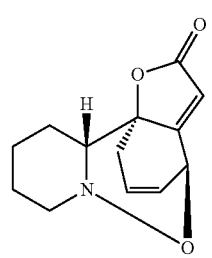 [SMILES: O=C1C=C2[C@@H]3C=CC[C@@]2(O1)[C@H]1CCCCN1O3] |
| INVS-MG-52D | 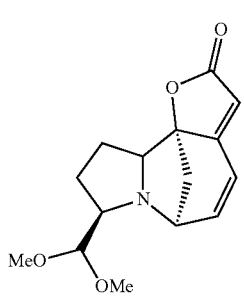 [SMILES: COC(OC)[C@H]1CCC2N1[C@@H]1C=CC3=CC(=O)O[C@@]32C1] |

-continued

| Sample Code | Structure |
|---|---|
| INVS-MG-108-IIB | 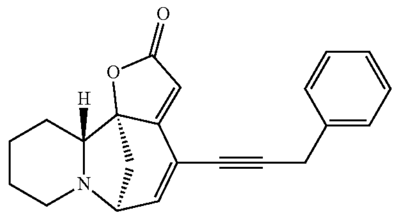 [SMILES: O=C1C=C2C(C#CCc3ccccc3)=C[C@@H]3C[C@@]2(O1)[C@H]1CCCCN31] |
| INVS-MG-109-IIA | 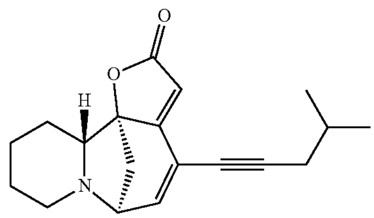 [SMILES: CC(C)CC#CC1=C[C@@H]2C[C@@]3(OC(=O)C=C13)[C@H]1CCCCN21] |
| INVS-MG-110B | 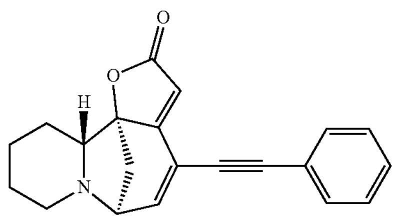 [SMILES: O=C1C=C2C(C#Cc3ccccc3)=C[C@@H]3C[C@@]2(O1)[C@H]1CCCCN31] |
| INVS-MG-105C | 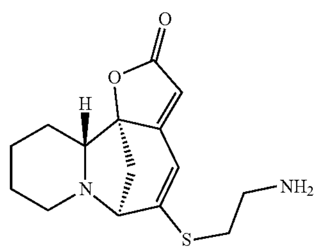 [SMILES: NCCSC1=CC2=CC(=O)O[C@@]23C[C@@H]1N1CCCC[C@@H]13] |
| INVS-MG-117B | 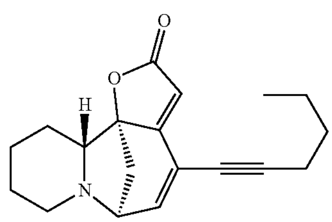 [SMILES: CCCCC#CC1=C[C@@H]2C[C@@]3(OC(=O)C=C13)[C@H]1CCCCN21] |
| INVS-MG-120A | 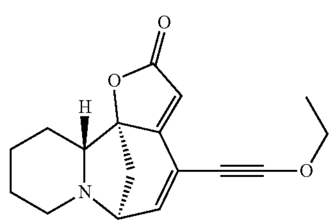 [SMILES: CCOC#CC1=C[C@@H]2C[C@@]3(OC(=O)C=C13)[C@H]1CCCCN21] |
| INVS-MG-121A | 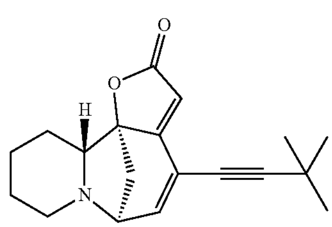 [SMILES: CC(C)(C)C#CC1=C[C@@H]2C[C@@]3(OC(=O)C=C13)[C@H]1CCCCN21] |

-continued

| Sample Code | Structure |
|---|---|
| INVS-MG-123B | 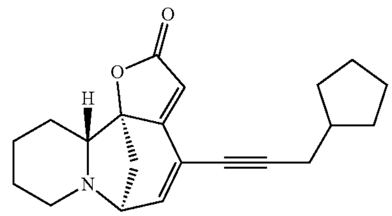 [SMILES: O=C1C=C2C(C#CCC3CCCC3)=C[C@@H]3C[C@@]2(O1)[C@H]1CCCCN31] |
| INVS-MG-98B | 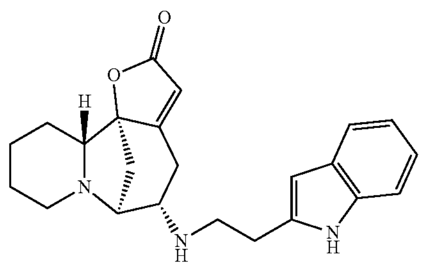 [SMILES: O=C1C=C2C[C@H](NCCc3cc4ccccc4[nH]3)[C@@H]3C[C@@]2(O1)[C@H]1CCCCN31] |
| INVS-MG-106B | 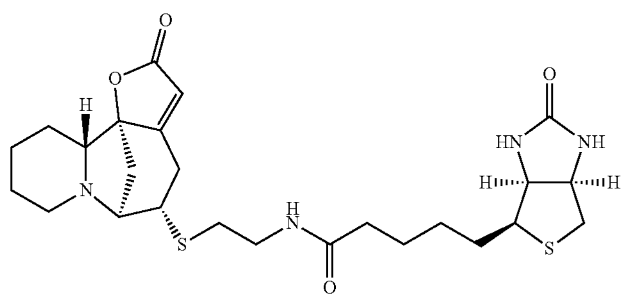 [SMILES: O=C(CCCC[C@@H]1SC[C@@H]2NC(=O)N[C@@H]21)NCCS[C@H]1CC2=CC(=O)O[C@@]23C[C@@H]1N1CCCC[C@@H]13] |
| INVS-MG-111B | 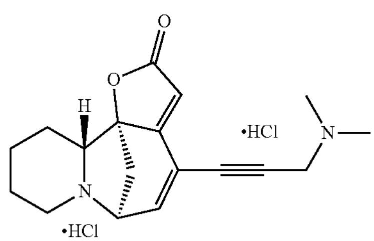 [SMILES: CN(C)CC#CC1=C[C@@H]2C[C@@]3(OC(=O)C=C13)[C@H]1CCCCN21 ; Cl ; Cl] |
| INVS-MG-125A | 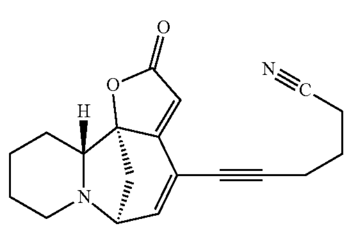 [SMILES: N#CCCCC#CC1=C[C@@H]2C[C@@]3(OC(=O)C=C13)[C@H]1CCCCN21] |
| INVS-MG-118-IIB | 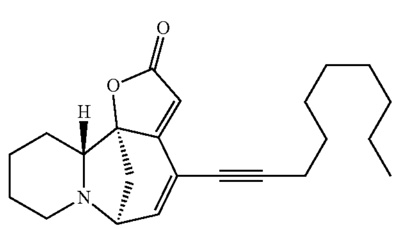 [SMILES: CCCCCCCCC#CC1=C[C@@H]2C[C@@]3(OC(=O)C=C13)[C@H]1CCCCN21] |

| Sample Code | Structure |
|---|---|
| INVS-MG-111B | 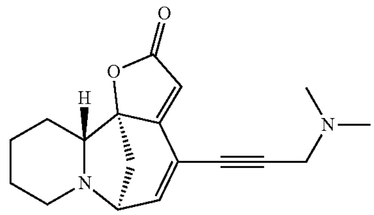 [SMILES: CN(C)CC#CC1=C[C@@H]2C[C@@]3(OC(=O)C=C13)[C@H]1CCCCN21] |
| INVS-MG-113A | 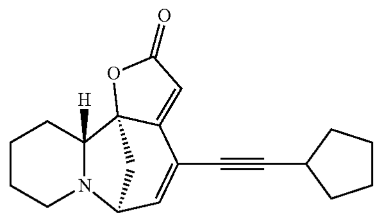 [SMILES: O=C1C=C2C(C#CC3CCCC3)=C[C@@H]3C[C@@]2(O1)[C@H]1CCCCN31] |
| INVS-MG-110B | 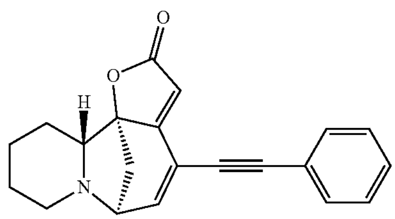 [SMILES: O=C1C=C2C(C#Cc3ccccc3)=C[C@@H]3C[C@@]2(O1)[C@H]1CCCCN31] |
| INVS-MG-133-II | 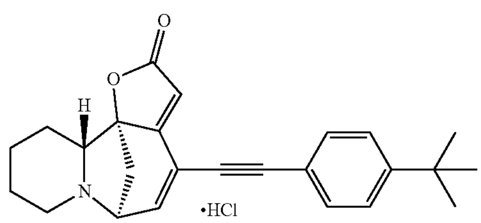 [SMILES: CC(C)(C)c1ccc(C#CC2=C[C@@H]3C[C@@]4(OC(=O)C=C24)[C@H]2CCCCN32)cc1 ; Cl] |
| INVS-MG-133B | 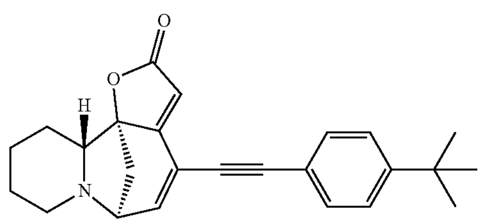 [SMILES: CC(C)(C)c1ccc(C#CC2=C[C@@H]3C[C@@]4(OC(=O)C=C24)[C@H]2CCCCN32)cc1] |
| INVS-MG-137-II | 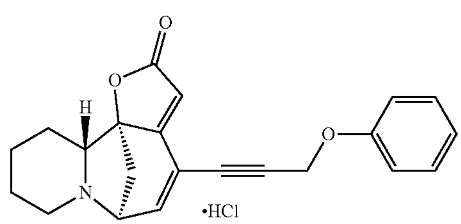 [SMILES: O=C1C=C2C(C#CCOc3ccccc3)=C[C@@H]3C[C@@]2(O1)[C@H]1CCCCN31 ; Cl] |
| INVS-MG-124A | 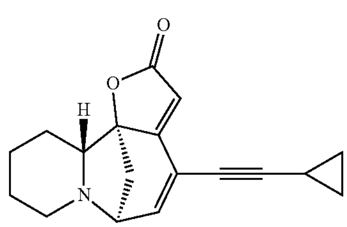 [SMILES: O=C1C=C2C(C#CC3CC3)=C[C@@H]3C[C@@]2(O1)[C@H]1CCCCN31] |

-continued

| Sample Code | Structure |
|---|---|
| INVS-MG-125A | 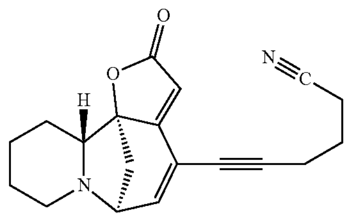 [SMILES: N#CCCCC#CC1=C[C@@H]2C[C@@]3(OC(=O)C=C13)[C@H]1CCCCN21] |
| INVS-MG-152A | 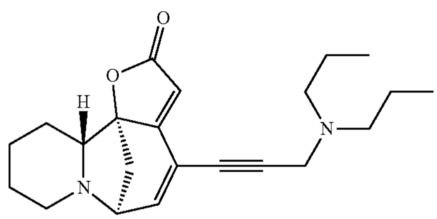 [SMILES: CCCN(CC#CC1=C[C@@H]2C[C@@]3(OC(=O)C=C13)[C@H]1CCCCN21)CCC] |
| INVS-MG-119A | 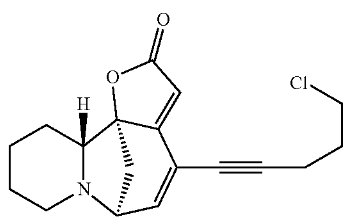 [SMILES: O=C1C=C2C(C#CCCCCl)=C[C@@H]3C[C@@]2(O1)[C@H]1CCCCN31] |
| INVS-MG-119B | 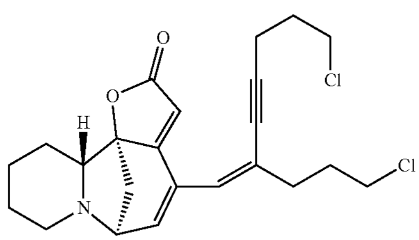 [SMILES: O=C1C=C2C(/C=C(\C#CCCCCl)CCCCl)=C[C@@H]3C[C@@]2(O1)[C@H]1CCCCN31] |
| INVS-MG-125 IIB | 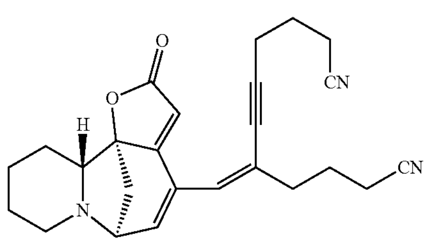 [SMILES: N#CCCCC#C/C(=C\C1=C[C@@H]2C[C@@]3(OC(=O)C=C13)[C@H]1CCCCN21)CCCC#N] |
| INVS-MG-147B | 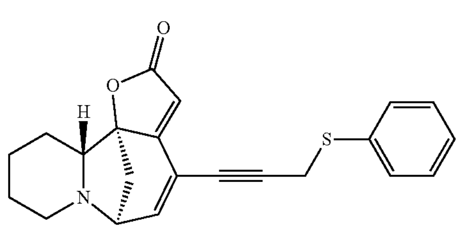 [SMILES: O=C1C=C2C(C#CCSc3ccccc3)=C[C@@H]3C[C@@]2(O1)[C@H]1CCCCN31] |

-continued

| Sample Code | Structure |
|---|---|
| INVS-MG-77 | 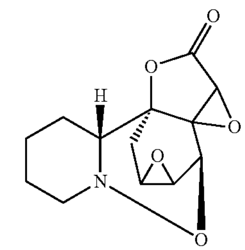 [SMILES: O=C1O[C@]23CC4OC4[C@H](ON4CCCC[C@@H]42)C32OC12] |
| INVS-MG-52B | 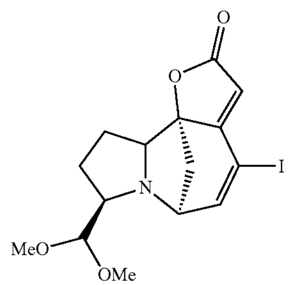 [SMILES: COC(OC)[C@H]1CCC2N1[C@@H]1C=C(I)C3=CC(=O)O[C@@]32C1] |
| INVS-MG-132A | 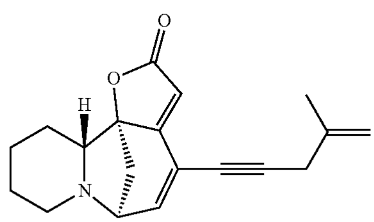 [SMILES: C=C(C)CC#CC1=C[C@@H]2C[C@@]3(OC(=O)C=C13)[C@H]1CCCCN21] |
| INVS-MG-134C | 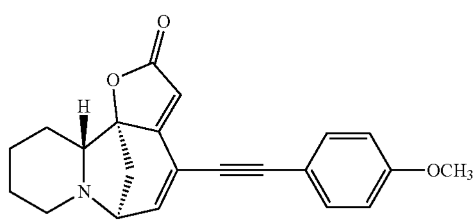 [SMILES: COc1ccc(C#CC2=C[C@@H]3C[C@@]4(OC(=O)C=C24)[C@H]2CCCCN32)cc1] |
| INVS-MG-135B | 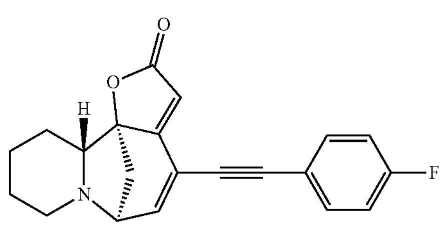 [SMILES: O=C1C=C2C(C#Cc3ccc(F)cc3)=C[C@@H]3C[C@@]2(O1)[C@H]1CCCCN31] |
| INVS-MG-145-II | 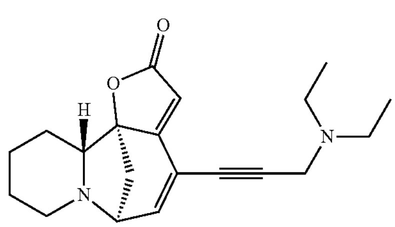 |

-continued

| Sample Code | Structure |
|---|---|
| INVS-MG-86C | 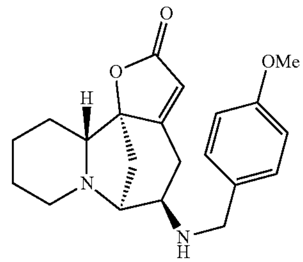 [SMILES: COc1ccc(CN[C@@H]2CC3=CC(=O)O[C@@]34C[C@@H]2N2CCCC[C@@H]24)cc1] |
| INVS-MG-146-II | 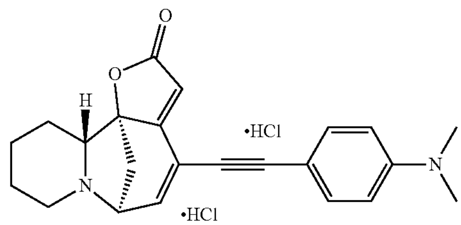 [SMILES: CN(C)c1ccc(C#CC2=C[C@@H]3C[C@@]4(OC(=O)C=C24)[C@H]2CCCCN32)cc1 ; Cl ; Cl] |
| INVS-MG-146B | 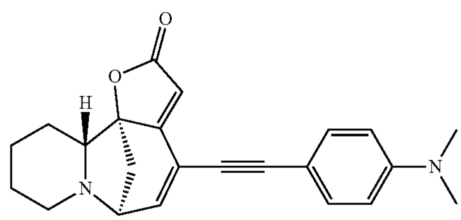 [SMILES: CN(C)c1ccc(C#CC2=C[C@@H]3C[C@@]4(OC(=O)C=C24)[C@H]2CCCCN32)cc1] |
| INVS-MG-150B | 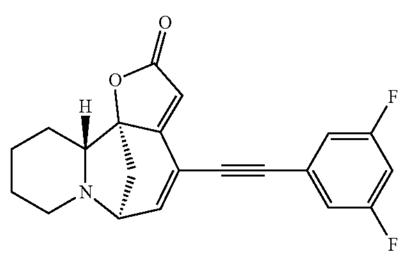 [SMILES: O=C1C=C2C(C#Cc3cc(F)cc(F)c3)=C[C@@H]3C[C@@]2(O1)[C@H]1CCCCN31] |
| INVS-MG-136B | 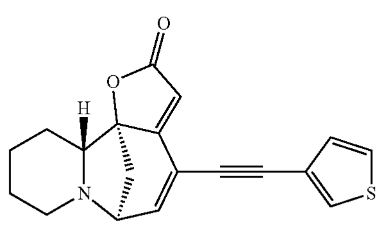 [SMILES: O=C1C=C2C(C#Cc3ccsc3)=C[C@@H]3C[C@@]2(O1)[C@H]1CCCCN31] |
| INVS-MG-149B | 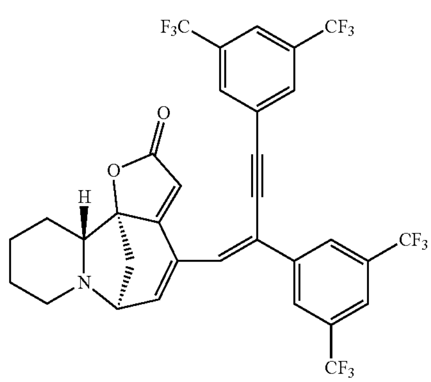 [SMILES: O=C1C=C2C(/C=C(\C#Cc3cc(C(F)(F)F)cc(C(F)(F)F)c3)c3cc(C(F)(F)F)cc(C(F)(F)F)c3)=C[C@@H]3C[C@@]2(O1)[C@H]1CCCCN31] |

| Sample Code | Structure |
|---|---|
| INVS-MG-149B' | 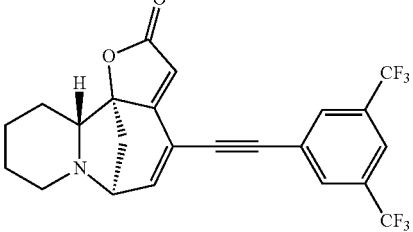 |
| INVS-MG-157-B | 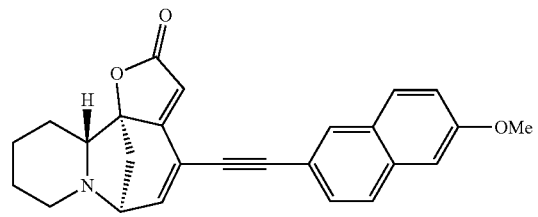 [SMILES: COc1ccc2cc(C#CC3=C[C@@H]4C[C@@]5(OC(=O)C=C35)[C@H]3CCCCN43)ccc2c1] |
| INVS-MG-152-IIB | 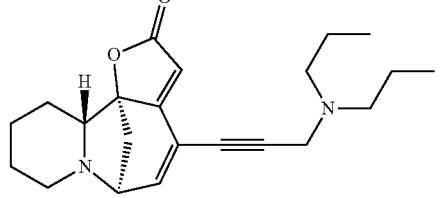 |
| INVS-MG-151B | 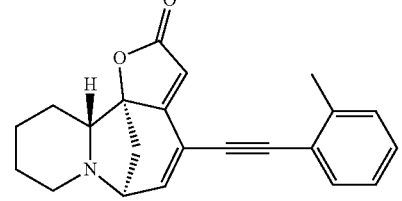 |
| INVS-MG-158B | 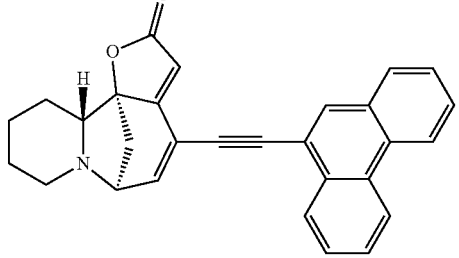 |
| INVS-MG-159A | 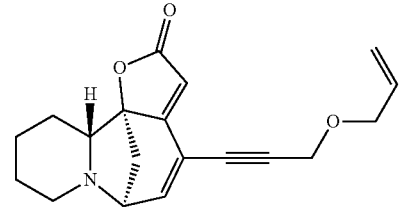 [SMILES: C=CCOCC#CC1=C[C@@H]2C[C@@]3(OC(=O)C=C13)[C@H]1CCCCN21] |

-continued

| Sample Code | Structure |
|---|---|
| INVS-MG-160B | 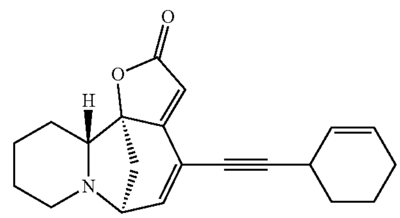 [SMILES: O=C1C=C2C(C#CC3C=CCCC3)=C[C@@H]3C[C@@]2(O1)[C@H]1CCCCN31] |
| INVS-MG-161B | 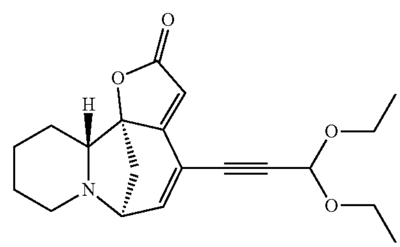 [SMILES: CCOC(C#CC1=C[C@@H]2C[C@@]3(OC(=O)C=C13)[C@H]1CCCCN21)OCC] |
| INVS-MG-162B | 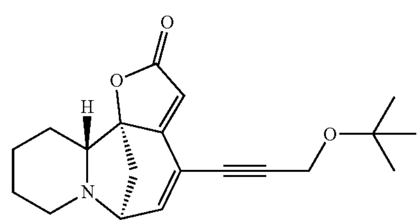 [SMILES: CC(C)(C)OCC#CC1=C[C@@H]2C[C@@]3(OC(=O)C=C13)[C@H]1CCCCN21] |
| INVS-MG-163-IIB | 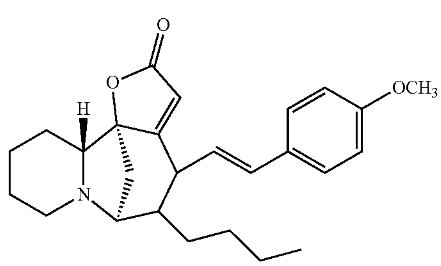 [SMILES: CCCCC1C(/C=C/c2ccc(OC)cc2)C2=CC(=O)O[C@@]23C[C@@H]1N1CCCC[C@@H]13] |
| INVS-MG-167B | 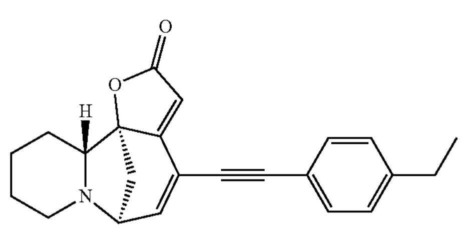 [SMILES: CCc1ccc(C#CC2=C[C@@H]3C[C@@]4(OC(=O)C=C24)[C@H]2CCCCN32)cc1] |
| INVS-MG-168B | 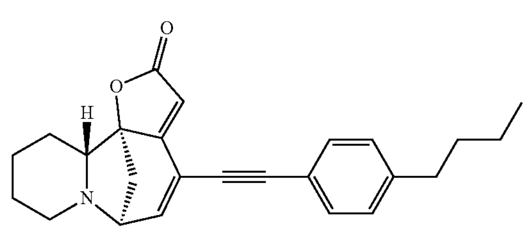 [SMILES: CCCCc1ccc(C#CC2=C[C@@H]3C[C@@]4(OC(=O)C=C24)[C@H]2CCCCN32)cc1] |

| Sample Code | Structure |
|---|---|
| INVS-MG-169B | 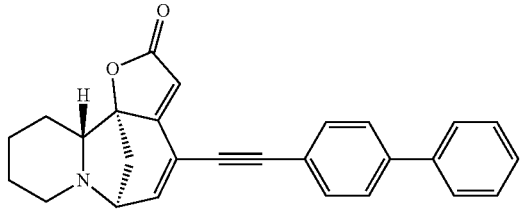 [SMILES: O=C1C=C2C(C#Cc3ccc(-c4ccccc4)cc3)=C[C@@H]3C[C@@]2(O1)[C@H]1CCCCN31] |
| INVS-MG-170B | 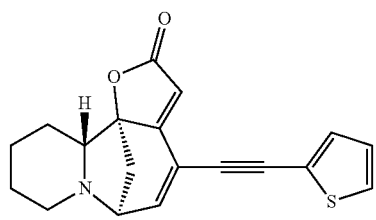 [SMILES: O=C1C=C2C(C#Cc3cccs3)=C[C@@H]3C[C@@]2(O1)[C@H]1CCCCN31] |
| INVS-MG-175A | 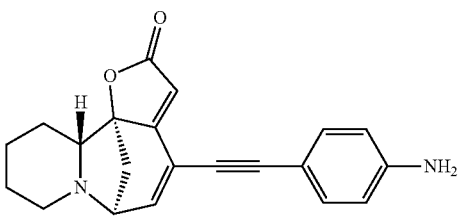 [SMILES: Nc1ccc(C#CC2=C[C@@H]3C[C@@]4(OC(=O)C=C24)[C@H]2CCCCN32)cc1] |
| INVS-MG-152-III | 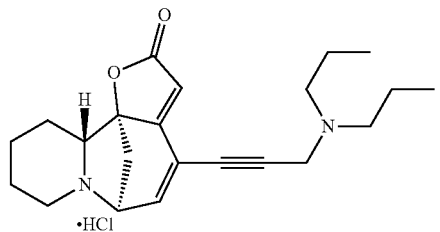 [SMILES: CCCN(CC#CC1=C[C@@H]2C[C@@]3(OC(=O)C=C13)[C@H]1CCCCN21)CCC ; Cl] |
| INVS-MG-157-IIB | 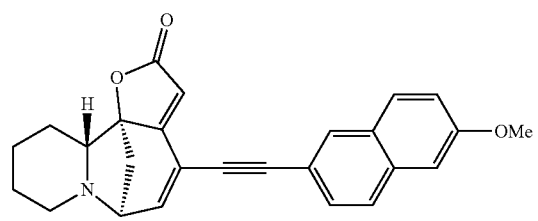 [SMILES: COc1ccc2cc(C#CC3=C[C@@H]4C[C@@]5(OC(=O)C=C35)[C@H]3CCCCN43)ccc2c1] |
| INVS-MG-157 III | 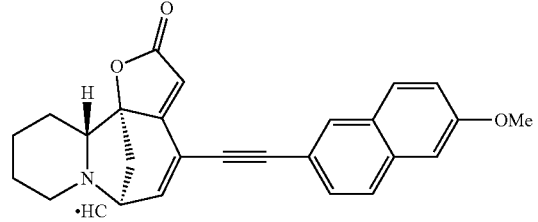 |

-continued
| Sample Code | Structure |
|---|---|
| INVS-MG-158-IIB | 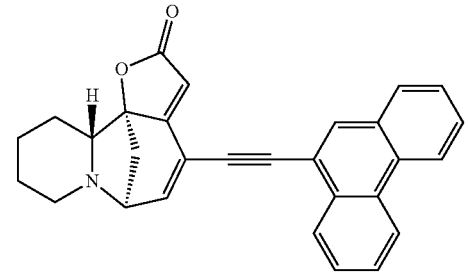 [SMILES: O=C1C=C2C(C#Cc3cc4ccccc4c4ccccc34)=C[C@@H]3C[C@@]2(O1)[C@H]1CCCCN31] |
| INVS-MG-158-III | 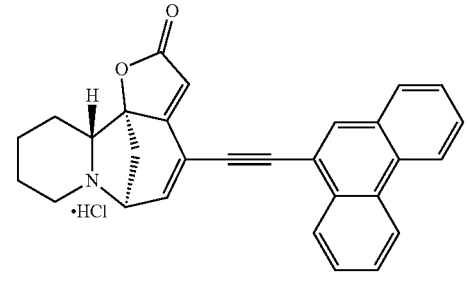 [SMILES: O=C1C=C2C(C#Cc3cc4ccccc4c4ccccc34)=C[C@@H]3C[C@@]2(O1)[C@H]1CCCCN31 ; Cl] |
| INVS-MG-169-IIB | 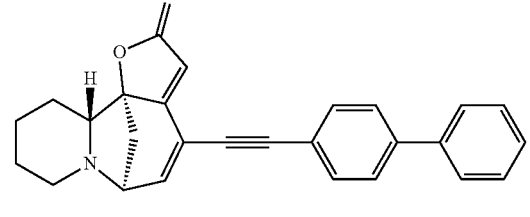 |
| INVS-MG-164B | 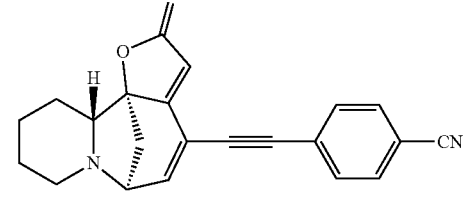 |
| INVS-MG-165B | 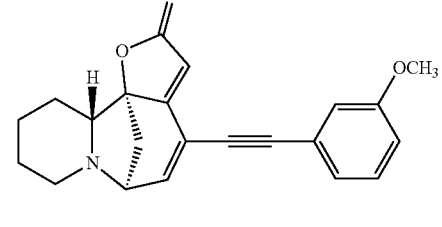 |
| INVS-MG-166B | 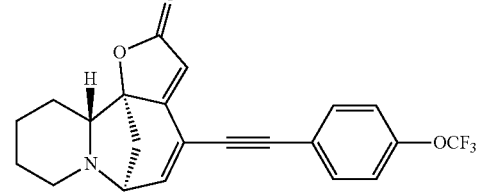 |

-continued

| Sample Code | Structure |
|---|---|
| INVS-MG-169-III | 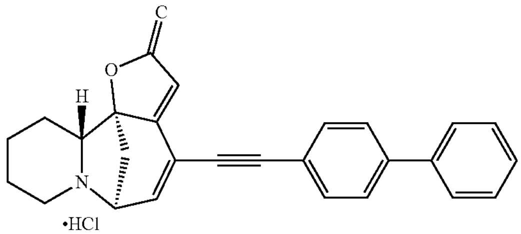 [SMILES: C=C1C=C2C(C#Cc3ccc(-c4ccccc4)cc3)=C[C@@H]3C[C@@]2(O1)[C@H]1CCCCN31 ; Cl] |
| INVS-MG-170-IIB | 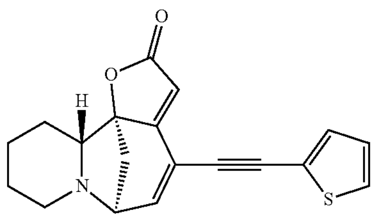 [SMILES: O=C1C=C2C(C#Cc3cccs3)=C[C@@H]3C[C@@]2(O1)[C@H]1CCCCN31] |
| INVS-MG-170-III | 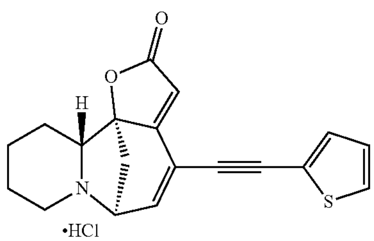 [SMILES: O=C1C=C2C(C#Cc3cccs3)=C[C@@H]3C[C@@]2(O1)[C@H]1CCCCN31 ; Cl] |
| INVS-MG-172C | 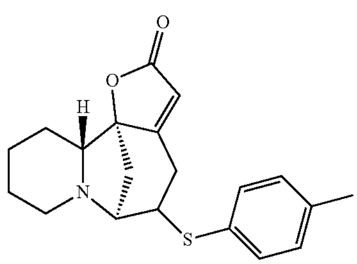 [SMILES: Cc1ccc(SC2CC3=CC(=O)O[C@@]34C[C@@H]2N2CCCC[C@@H]24)cc1] |
| INVS-MG-184B | 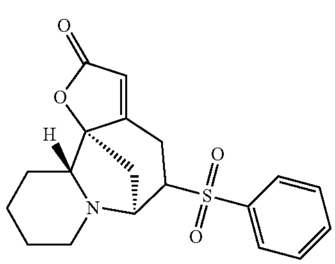 [SMILES: O=C1C=C2CC(S(=O)(=O)c3ccccc3)[C@@H]3C[C@@]2(O1)[C@H]1CCCCN31] |
| INVS-MG-146 IIIB | 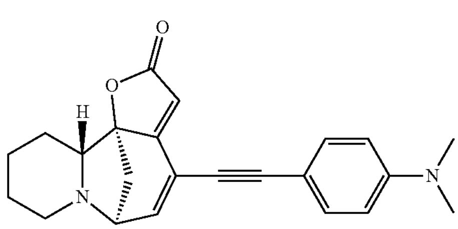 [SMILES: CN(C)c1ccc(C#CC2=C[C@@H]3C[C@@]4(OC(=O)C=C24)[C@H]2CCCCN32)cc1] |

-continued
| Sample Code | Structure |
|---|---|
| INVS-MG-175V | 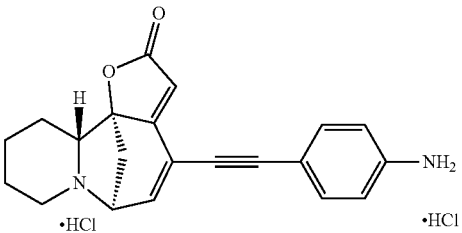 [SMILES: Nc1ccc(C#CC2=C[C@@H]3C[C@@]4(OC(=O)C=C24)[C@H]2CCCCN32)cc1 ; Cl ; Cl] |
| INVS-MG-193B | 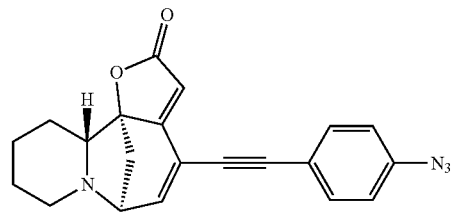 [SMILES: [N-]=[N+]=Nc1ccc(C#CC2=C[C@@H]3C[C@@]4(OC(=O)C=C24)[C@H]2CCCCN32)cc1] |
| INVS-MG-193-III | 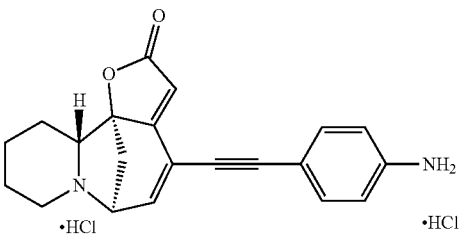 [SMILES: Nc1ccc(C#CC2=C[C@@H]3C[C@@]4(OC(=O)C=C24)[C@H]2CCCCN32)cc1 ; Cl ; Cl] |
| INVS-MG-176B | 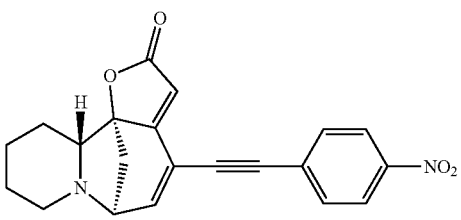 [SMILES: O=C1C=C2C(C#Cc3ccc([N+](=O)[O-])cc3)=C[C@@H]3C[C@@]2(O1)[C@H]1CCCCN31] |
| INVS-MG-176-II | 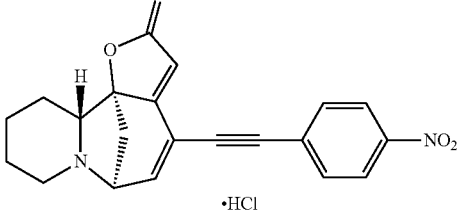 |
| INVS-MG-179B | 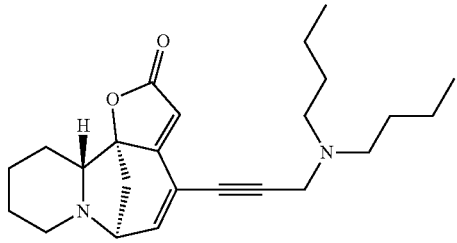 [SMILES: CCCCN(CC#CC1=C[C@@H]2C[C@@]3(OC(=O)C=C13)[C@H]1CCCCN21)CCCC] |

-continued
| Sample Code | Structure |
|---|---|
| INVS-MG-145-IIIA | 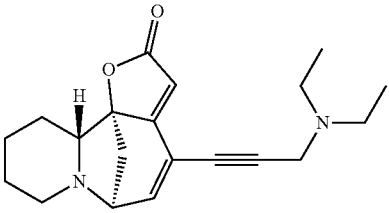 [SMILES: CCN(CC)CC#CC1=C[C@@H]2C[C@@]3(OC(=O)C=C13)[C@H]1CCCCN21] |
| INVS-MG-145-V | 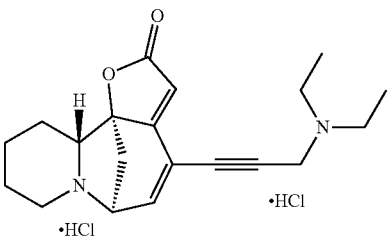 [SMILES: CCN(CC)CC#CC1=C[C@@H]2C[C@@]3(OC(=O)C=C13)[C@H]1CCCCN21 ; Cl ; Cl] |
| INVS-MG-158-IVC | 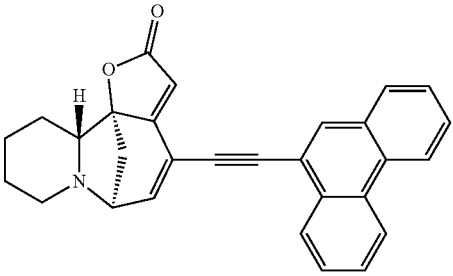 [SMILES: O=C1C=C2C(C#Cc3cc4ccccc4c4ccccc34)=C[C@@H]3C[C@@]2(O1)[C@H]1CCCCN31] |
| INVS-MG-158-V | 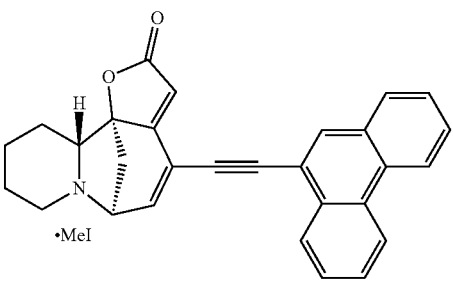 [SMILES: "·MeI" ; O=C1C=C2C(C#Cc3cc4ccccc4c4ccccc34)=C[C@@H]3C[C@@]2(O1)[C@H]1CCCCN31] |
| INVS-MG-158-VI | 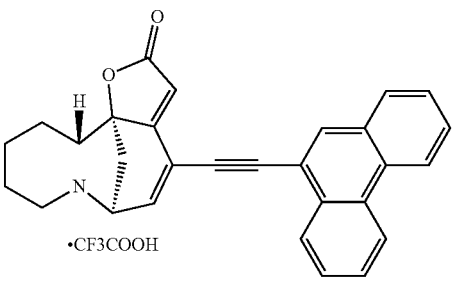 |
| INVS-MG-165-IIB | 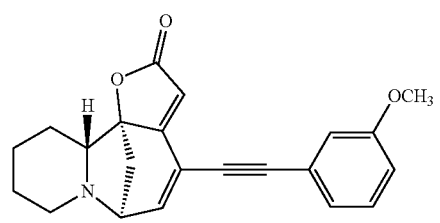 [SMILES: COc1cccc(C#CC2=C[C@@H]3C[C@@]4(OC(=O)C=C24)[C@H]2CCCCN32)c1] |

| Sample Code | Structure |
|---|---|
| INVS-MG-99 IVD | 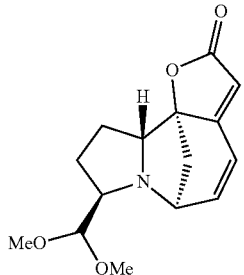 [SMILES: COC(OC)[C@H]1CC[C@H]2N1[C@@H]1C=CC3=CC(=O)O[C@@]32C1] |
| INVS-MG-99 IVDI | 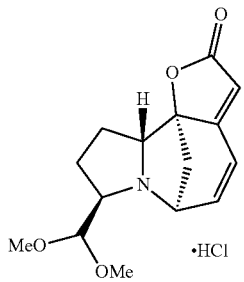 [SMILES: COC(OC)[C@H]1CC[C@H]2N1[C@@H]1C=CC3=CC(=O)O[C@@]32C1 ; Cl] |
| INVS-MG-219A | 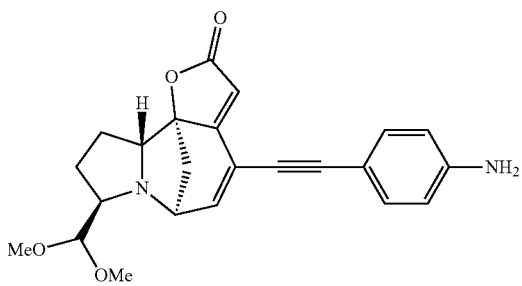 [SMILES: COC(OC)[C@H]1CC[C@H]2N1[C@@H]1C=C(C#Cc3ccc(N)cc3)C3=CC(=O)O[C@@]32C1] |
| INVS-MG-220B | 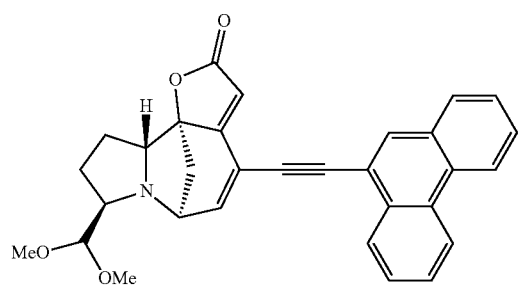 [SMILES: COC(OC)[C@H]1CC[C@H]2N1[C@@H]1C=C(C#Cc3cc4ccccc4c4ccccc34)C3=CC(=O)O[C@@]32C1] |
| INVS-MG-220C | 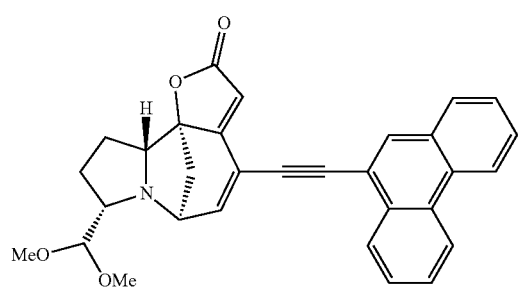 [SMILES: COC(OC)[C@@H]1CC[C@H]2N1[C@@H]1C=C(C#Cc3cc4ccccc4c4ccccc34)C3=CC(=O)O[C@@]32C1] |
str?? aromatic disturbed -continued
| Sample Code | Structure |
|---|---|
| INVS-MG-221B | 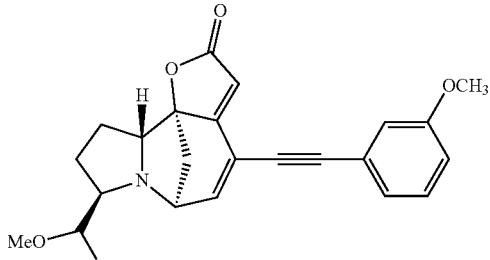 |
| INVS-MG-179-II | 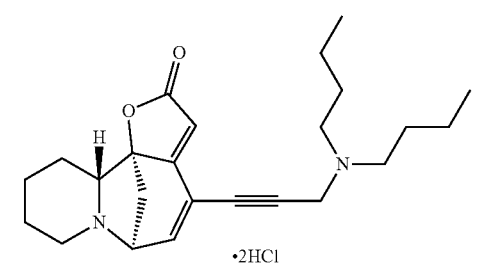 [SMILES: CCCCN(CC#CC1=C[C@@H]2C[C@@]3(OC(=O)C=C13)[C@H]1CCCCN21)CCCC] |
| INVS-MG-207A | 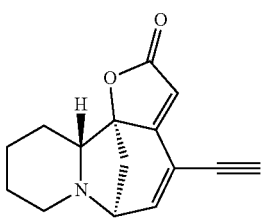 [SMILES: C#CC1=C[C@@H]2C[C@@]3(OC(=O)C=C13)[C@H]1CCCCN21] |
| INVS-MG-207-II | 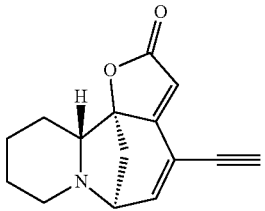 |
| INVS-MG-207 IIIA | 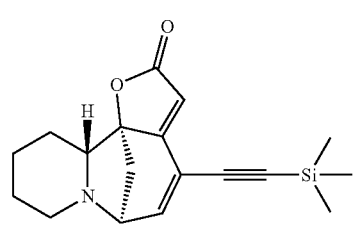 [SMILES: C[Si](C)(C)C#CC1=C[C@@H]2C[C@@]3(OC(=O)C=C13)[C@H]1CCCCN21] |
| INVS-MG-224A | 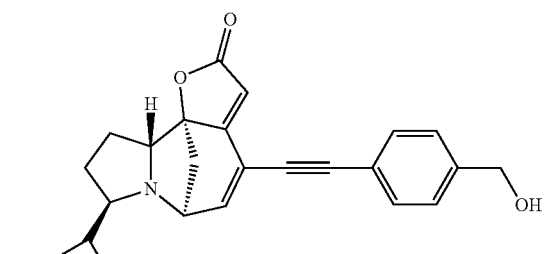 |

-continued
| Sample Code | Structure |
|---|---|
| INVS-MG-222-III | 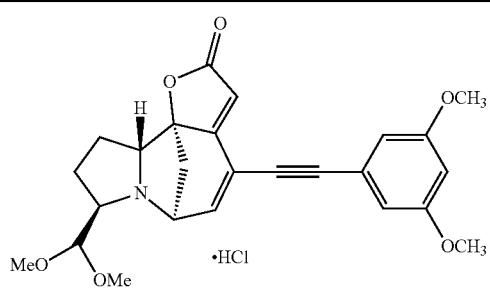 |
| INVS-MG-165-III | 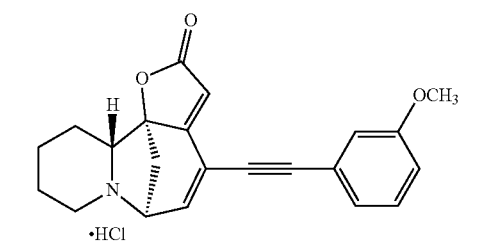 [SMILES: COc1cccc(C#CC2=C[C@@H]3C[C@@]4(OC(=O)C=C24)[C@H]2CCCCN32)c1 ; Cl] |
| INVS-MG-99-IVB | 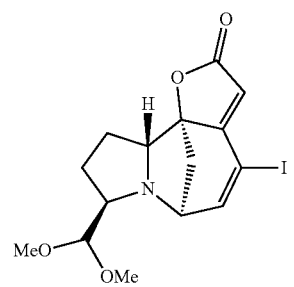 |
| INV-SZ-117-3 | 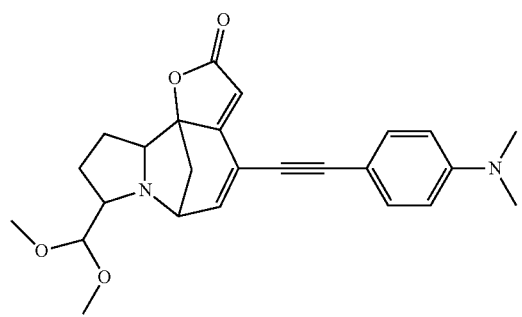 |
| INV-117-4 | 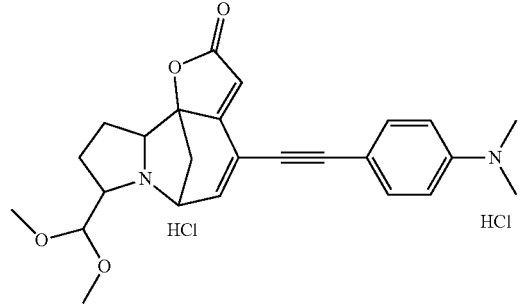 |

| Sample Code | Structure |
|---|---|
| INV-SZ-118-2 | 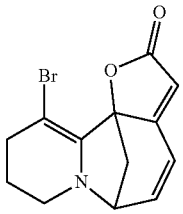 [SMILES: O=C1C=C2C=CC3CC2(O1)C1=C(Br)CCCN13] |
| INV-SZ-120-1 | 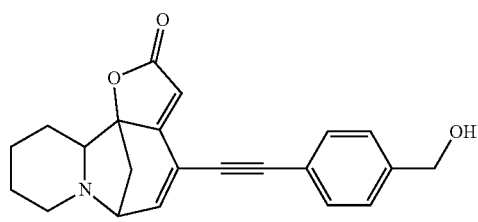 [SMILES: O=C1C=C2C(C#Cc3ccc(CO)cc3)=CC3CC2(O1)C1CCCCN31] |
| INVS-MG-222B | 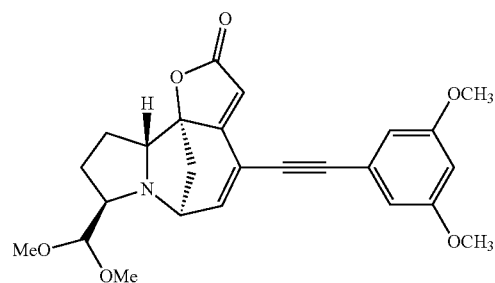 [SMILES: COc1cc(C#CC2=C[C@@H]3C[C@@]4(OC(=O)C=C24)[C@H]2CC[C@H](C(OC)OC)N32)cc(OC)c1] |
| INVS-MG-223B | 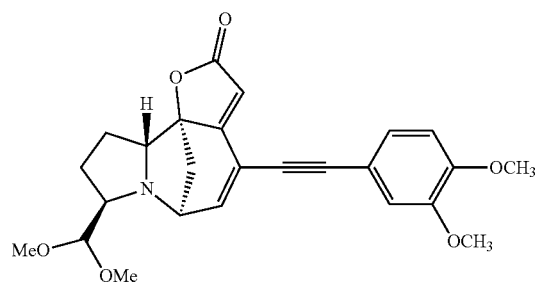 [SMILES: COc1ccc(C#CC2=C[C@@H]3C[C@@]4(OC(=O)C=C24)[C@H]2CC[C@H](C(OC)OC)N32)cc1OC] |
| INV-SZ-125-3 | 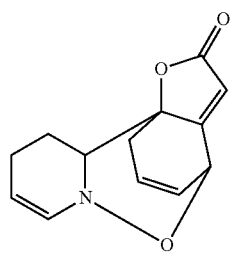 [SMILES: O=C1C=C2C3C=CCC2(O1)C1CCC=CN1O3] |
| INV-SZ-125-2 | 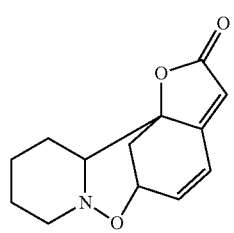 [SMILES: O=C1C=C2C=CC3CC2(O1)C1CCCCN1O3] |

| Sample Code | Structure |
|---|---|
| INV-SZ-125-1 | 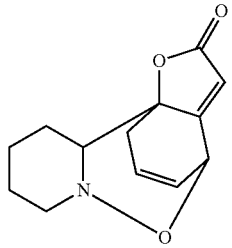 [SMILES: O=C1C=C2C3C=CCC2(O1)C1CCCCN1O3] |
| INV-SZ-127-1 | 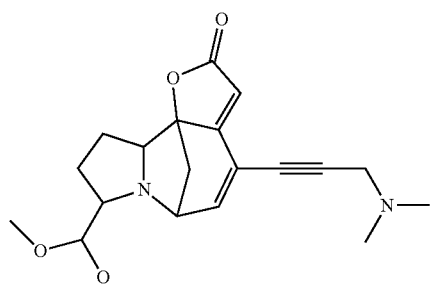 |
| INVS-MG-184-IIB | 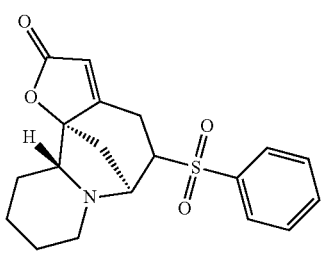 [SMILES: O=C1C=C2CC(S(=O)(=O)c3ccccc3)[C@@H]3C[C@@]2(O1)[C@H]1CCCCN31] |
| INVS-MG-209A | 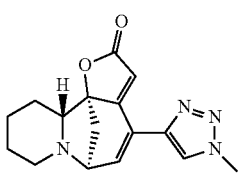 |
| | 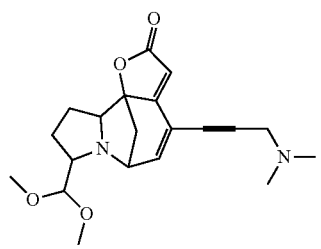 |
| INV-SZ-129-1 | 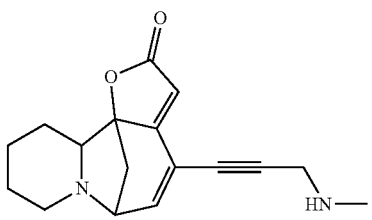 [SMILES: CNCC#CC1=CC2CC3(OC(=O)C=C13)C1CCCCN21] |

-continued
| Sample Code | Structure |
|---|---|
| INV-SZ-134-1 | 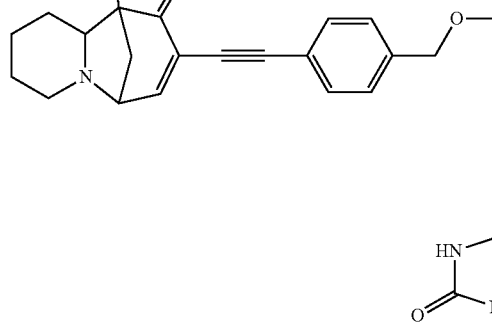 |
| INV-SZ-121-1 | 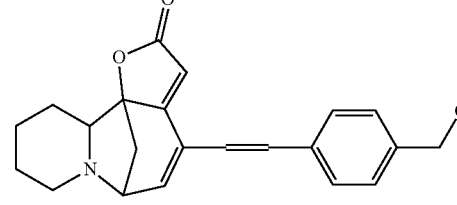 |
| INV-SZ-113-2 | 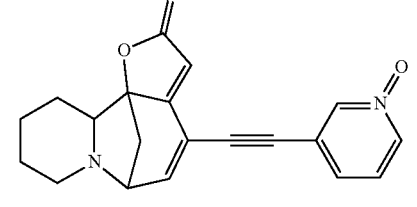 |
| INV-SZ-114-1 | 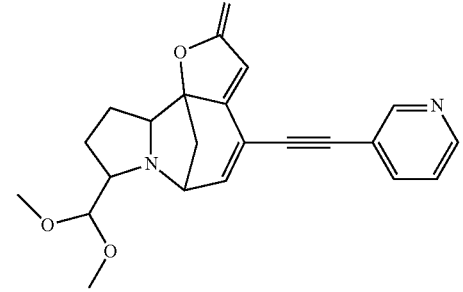 |
| INV-SZ-115-1 | 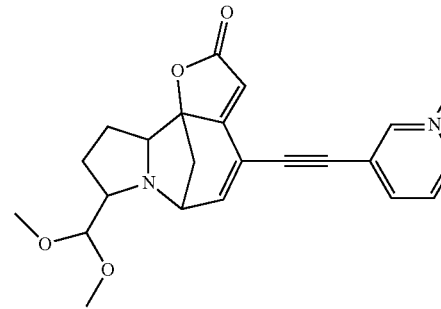 |

-continued
| Sample Code | Structure |
|---|---|
| INV-SZ-116-1 | 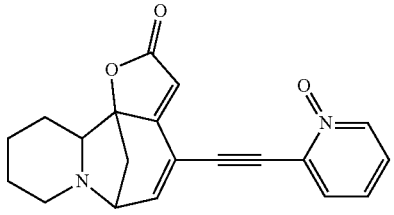 [SMILES: O=C1C=C2C(C#Cc3cccc[n+]3[O-])=CC3CC2(O1)C1CCCCN31] |
| INV-SZ-133-1 | 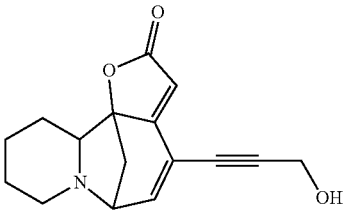 [SMILES: O=C1C=C2C(C#CCO)=CC3CC2(O1)C1CCCCN31] |
| INV-SZ-123-2 | 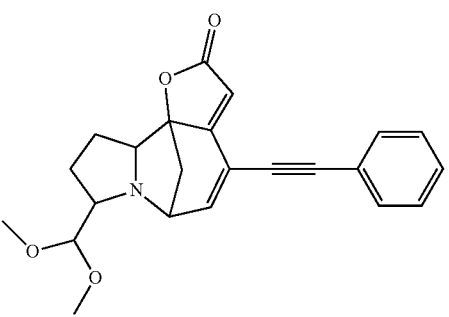 [SMILES: COC(OC)C1CCC2N1C1C=C(C#Cc3ccccc3)C3=CC(=O)OC32C1] |
| INV-SZ-123-3 | 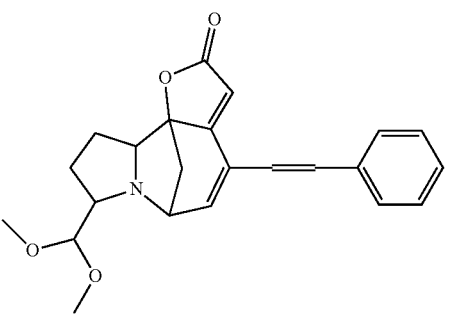 [SMILES: COC(OC)C1CCC2N1C1C=C(C=Cc3ccccc3)C3=CC(=O)OC32C1] |
| INV-SZ-136-1 | 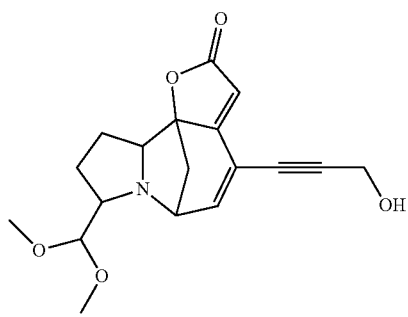 [SMILES: COC(OC)C1CCC2N1C1C=C(C#CCO)C3=CC(=O)OC32C1] |

-continued
| Sample Code | Structure |
|---|---|
| INV-SZ-137-1 | 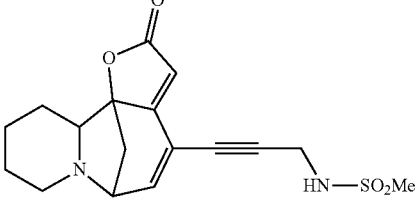 |
| INV-SZ-138-2 | 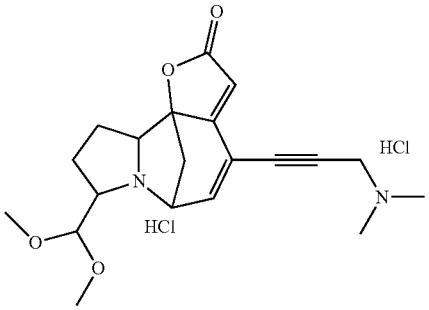 |
| INV-SZ-140-1 | 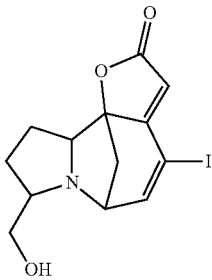 [SMILES: O=C1C=C2C(I)=CC3CC2(O1)C1CCC(CO)N31] |
| INV-SZ-132-1 | 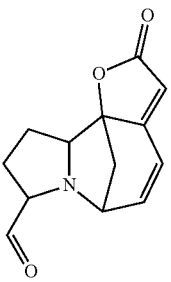 [SMILES: O=CC1CCC2N1C1C=CC3=CC(=O)OC32C1] |
| INV-SZ-141-1 | 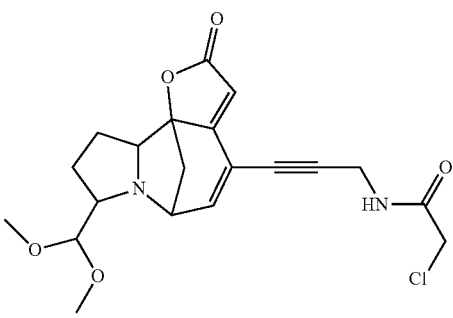 [SMILES: COC(OC)C1CCC2N1C1C=C(C#CCNC(=O)CCl)C3=CC(=O)OC32C1] |

| Sample Code | Structure |
|---|---|
| INVS-MG-184-III | *(structure shown: tricyclic core with furanone, fused piperidine N, phenylsulfonyl substituent; ·HCl salt)* |
| INV-SZ-122-1 | *(structure shown: tricyclic furanone core with alkyne linker to 4-(dimethylamino)phenyl group)* |
| INVS-MG-111B | *(structure shown: tricyclic furanone core with propargyl-dimethylamine substituent)* |
| INVS-MG-136-III | *(structure shown: tricyclic furanone core with alkyne linker to 3-thienyl group; ·HCl)* |
| INVS-MG-144B | *(structure shown: tricyclic furanone core with alkyne linker to 3-pyridyl group)* |
| INVS-MG-99 IVB-I | *(structure shown: bicyclic furanone core with iodo substituent on vinyl, pyrrolidine N, and CH(OMe)$_2$ dimethyl acetal group; ·HCl)* |

| Sample Code | Structure |
|---|---|
| INVS-MG-145A | 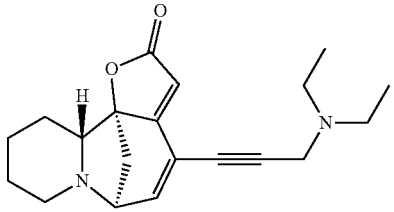 |
| INVS-MG-146-II | 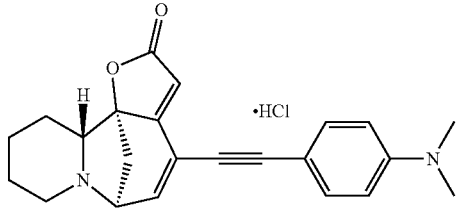 |

The present invention also provides for pharmaceutical compositions comprising the securinine and/or norsecurinine compounds described herein. The pharmaceutical compositions comprise at least one securinine or norsecurinine derivative as described herein or a salt thereof and a pharmaceutically acceptable carrier, which are known in the art. Pharmaceutically acceptable carriers include diluents, fillers, salts, buffers, stabilizers, solubilizers and other materials that are well-known in the art and may routinely comprise salt, buffering agents, preservatives, compatible carriers, and optionally other therapeutic agents. Those skilled in the art will understand that intermediate non-pharmaceutically acceptable salts may be used to prepare pharmaceutically-acceptable salts thereof and are not to be considered excluded from the scope of the invention. Pharmaceutically acceptable salts may include, but are not limited to, those prepared from the following acids: hydrochloric, hydrobromic, sulfuric, nitric, phosphoric, maleic, acetic, salicylic, citric, formic, malonic, succinic, and the like. Similarly, pharmaceutically-acceptable salts can be prepared as alkaline metal or alkaline earth salts, such as sodium, potassium or calcium salts.

The securinine and/or norsecurinine analogs described herein may be formulated into preparations in solid, semi-solid, liquid or gaseous forms such as tablets, capsules, powders, granules, ointments, solutions, depositories, inhalants and injections, and usual ways for oral, parenteral, intravenal, intragastric, rectal, intraperitoneal, intraarterial, subcutaneous, intravascular, topical, ocular, intranasal, intratracheal, intracranial, intramuscular, intracardiac, intrathoracic, intracranial, or surgical administration. As may be evident, the securinine and norsecurinine compounds described herein may further be derived into a prodrug which, as is known in the art, involves covalently attaching a further group, such as a protecting group, to the compound that will be removed by the subject's own biology, such as through metabolizing the compound (e.g. by cytochrome p450 or other enzymatic reactions), enzymatic degradation, or through changes in surrounding pH or ionic environment or temperature (see, e.g. epharmacology.hubpages.com/hub/Pharmacological-Effects-Prodrugs-Definition-Examples-and-Sources-of-Drug-Information). Prodrugs may improve the administration, distribution, metabolism and/or excretion of the compound. Prodrugs may improve the half life of administered analogs, increase the therapeutic index or alter the effective dose (e.g., ED50). For example, a protecting group can be easily introduced as ethers or esters at the oxygen molecules attached methyl of the rearranged ring in norsecurinine.

The present invention also provides methods of using the securinine and norsecurinine analogs described herein. The securinine and/or norsecurinine analogs may be administered to a cell, such as a cell of an organism in vivo or isolated from an organism in vitro or ex vivo. The cell may be part of an organ, such as the lungs, kidney, liver, intestine, brain, skin, gall bladder, circulatory system, heart, eye, testes, ovaries, bladder, prostate, colon or lymph. The cell may be within an organ system, such as the circulatory system, digestive system, cardiovascular system, immune system, lymphatic system, skeletal system, reproductive system, urinary system, endocrine system, respiratory system, muscular system or nervous system.

The securinine analogs may be administered or be caused to come into contact with a small molecule, such as a protein, enzyme, nucleic acid, carbohydrate, ion, anion, lipid or amino acid, within or superficially to the cell and alter the small molecule's function within the cell, such as by improving catalytic activity (e.g. blocking suppressing molecules or improving access to a catalytic domain) or inhibiting an active site on the small molecule, such as a catalytic domain or a binding site for another interacting molecule. The cell may be isolated or be part of an organism, such as a eukaryote. The cell may be a diseased or malfunctioning cell, e.g. cells wherein undesired genes and proteins are being expressed. The cell may be an abnormally arrested cell, such that it is unable to properly mature.

The methods of the present invention comprise selecting a cell or a subject in known or suspected need of treatment with the securinine and norsecurinine analogs described herein. For example, as set forth in the Examples below, securinine and norsecurinine analogs have demonstrated efficacy in treating or ameliorating various conditions, such as cell malignancy, cell proliferation, tumor growth, inflammation, immune system modulation, or myeloid disorders or enzyme catalytic action. The cell or subject may be selected by assaying for a suspected complication. A subject may be selected following a diagnosis of a physician upon analysis of the subject's symptoms and overall physiology. A cell may be selected based upon phenotype or known/identified classification. The subject may be an animal, such as a mammal, reptile, amphibian, bird or fish, or a plant. The subject may be a mammal, such as human, bovine, canine, feline, porcine, equine, murine, marsupial, ovine or related mammal. Cells or subjects appropriate for treatment can be determined with assays known in the art. For example, biomarkers, such as overexpressed or underexpressed proteins, deformed genes, or mutant post-translationally modified proteins can be detected by various mechanisms known in the art, such as chromatography, blotting, NMR, HPLC, ELISA, LC-MS/MS, and so forth. Following detection, further analysis may be performed as needed to confirm or refute the underlying condition.

The methods of the present invention comprise treating or ameliorating a cell undergoing abnormal growth, such as a neoplastic cell, a malignant cell, a metastatic cell or a tumor cell. As described herein, securinine and norsecurinine analogs have demonstrated efficacy in treating various cells that are representative of uncontrolled or mutant cell growth. As is known in the art, cells can malfunction and begin to proliferate in an abnormal manner, the cause of which can be wide ranging including: DNA or gene mutations, improperly expressed or translated proteins, abnormal gene expression, abnormal DNA or gene repair, exposure to chemical carcinogens, inhibited apoptosis, environmental exposure, lifestyle choices or any combination thereof. The present invention provides in part methods of addressing or rectifying the abnormality within the cell(s) by administering the securinine and/or norsecurinine analogs described herein in a therapeutically effective amount, namely that amount that will elicit the biological or medical response of a tissue system, animal or human that is being sought, resulting in a beneficial effect for at least a statistically significant fraction of subjects, such as an improvement of symptoms, a cure, a reduction in disease load, reduction in tumor mass, extended life of the subject, or improved quality of life. Contacting cancerous cells with a securinine or norsecurinine analog of the present invention may cease or inhibit or reduce the rate of cancerous cell proliferation. Contacting cancerous cells with a securinine or norsecurinine analog of the present invention may trigger cancerous cell death or induce cancerous cell apoptosis. Contacting cancerous cells with a securinine or norsecurinine analog of the present invention may induce cellular differentiation, such as cell maturing and thereby reduce overall cell proliferation.

The present invention also provides combination therapy for the treatment of a cancer or a cancerous cell by combining the securinine or norsecurinine analogs describes herein with a known chemotherapeutic agent. Cancerous cells may be part of a malignant or non-malignant cancer or tumor. Cancers or tumors include but are not limited to benign and malignant tumors; Acute lymphoblastic leukemia (ALL), acute myeloid leukemia, adrenocortical carcinoma, AIDS-related cancers, AIDS-related lymphoma, anal cancer, appendix cancer, astrocytoma (cerebellar or cerebral), basal-cell carcinoma, bile duct cancer (cholangiocarcinoma), bladder cancer, bone tumor (osteosarcoma/malignant fibrous histiocytoma), brainstem glioma, brain cancer, brain tumor (cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumor (gastrointestinal), carcinomas, cerebellar astrocytoma, cerebral astrocytoma/malignant glioma, cervical cancer, childhood cancers, chronic bronchitis, chronic lymphocytic leukemia, chronic myelogenous leukemia, chronic myeloproliferative disorders, chronic obstructive pulmonary disease (COPD), colon cancer, cutaneous T-cell lymphoma, desmoplastic small round cell tumor, emphysema, endometrial cancer, ependymoma, esophageal cancer, Ewing's sarcoma, extracranial germ cell tumor, extragonadal germ cell tumor, extrahepatic bile duct cancer, eye cancer (intraocular melanoma, retinoblastoma), gallbladder cancer, gastric (stomach) cancer, gastrointestinal carcinoid tumor, gastrointestinal stromal tumor (GIST), germ cell tumor (extracranial, extragonadal, or ovarian), gestational trophoblastic tumor, gastric carcinoid, hairy cell leukemia, head and neck cancer, heart cancer, hepatocellular (liver) cancer, Hodgkin lymphoma, hypopharyngeal cancer, hypothalamic and visual pathway glioma, intraocular melanoma, islet cell carcinoma (endocrine pancreas), Kaposi sarcoma, kidney cancer (renal cell cancer), laryngeal cancer, leukemia (acute lymphoblastic, acute myeloid, chronic lymphocytic, chronic myelogenous), lip and oral cavity cancer, liposarcoma, liver cancer, lung cancer (non-small cell, small cell), lymphoma (AIDS-related, Burkitt, cutaneous T-Cell, Hodgkin, Non-Hodgkin, primary central nervous system), Macroglobulinemia, Waldenström, male breast cancer, malignant fibrous histiocytoma of bone/osteosarcoma, medulloblastoma, melanoma, Merkel cell cancer, mesothelioma, childhood, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myeloid leukemia, myeloma, multiple (cancer of the bone-marrow), myeloproliferative disorders, nasal cavity and paranasal sinus cancer, nasopharyngeal carcinoma, neuroblastoma, oral cancer, oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, pleuropulmonary blastoma, primary central nervous system lymphoma, prostate cancer, rectal cancer, renal cell carcinoma, retinoblastoma, rhabdomyosarcoma, salivary gland cancer, sarcoma (Ewing family of tumors, Kaposi, soft tissue, uterine), Sézary syndrome, skin cancer, small cell lung cancer, small intestine cancer, soft tissue sarcoma, squamous cell carcinoma, squamous neck cancer with occult primary, stomach cancer, supratentorial primitive neuroectodermal tumor, testicular cancer, throat cancer, thymoma and thymic carcinoma, thyroid cancer, transitional cell cancer of the renal pelvis and ureter, trophoblastic tumor, ureter and renal pelvis cancer, uterine cancer, uterine sarcoma, vaginal cancer, visual pathway and hypothalamic glioma, vulvar cancer, Waldenström macroglobulinemia, and Wilms tumor (kidney cancer).

Those skilled in the art will appreciate that the securinine and/or norsecurinine analogs described herein can be used in combination with each other.

The present invention provides in part methods for treating cancerous cells by administering one or more of the securinine and/or norsecurinine analogs described herein to a cancerous cell, either in vitro or in vivo or ex vivo. The cancerous cell may be of a subject or derived from a subject with myeloid leukemia or a myeloid disorder including but not limited to: acute myeloid leukemia, chronic myeloid leukemia, myeloid proliferative dysplasias, myelodysplastic syndrome, myelodysplastic/myeloproliferative neoplasias (MDS/MPN), myeloid and lymphoid neoplasias together with eosinophilia and abnormalities of PDGFRA, PDGFRB and FGFR1, chronic myeloid leukemia (CML), polycythaemia vera (PV), essential thrombocytosis (ET), primary myelofibrosis (PMF), chronic eosinophilic leukemia (CEL), systematic mastocytosis (SM), and myeloproliferative neoplasias not to be classified (MPN-U).

As demonstrated herein, administration and/or contacting premyeloid and myeloid human leukemia cells (e.g. HL60, Molm-3 and OCI) with securinine and/or norsecurinine analogs described herein produced improved differentiation of the cells. The tested compounds and their respective results are produced in Table 1. Those skilled in the art will appreciate that combining the securinine and/or norsecurinine analogs with other differentiation inducing agents, such as all-trans retinoic acid, cytarabine and/or an anthracycline, would be of further benefit. Those skilled in the art will appreciate that inducing differentiation may further reduce oxidative damage due to lower presence of radical inducing enzymes (see, e.g., Yamada et al. J Biol Chem 259(5)3021-3025 (1984) and Weil et al., PNAS 84:2057-2061 (1987)).

The present invention also provides in part methods of inducing differentiation in a cell, such as a cell of a subject. Inducing differentiating may be achieved by contacting or administering to an undifferentiated cell the securinine and/or norsecurinine analogs of the present invention. As described herein, the securinine and norsecurinine analogs of the present invention have demonstrated unexpected improved ability over the parent molecules in inducing the differentiation of an abnormal cell that is failing to properly mature, such as the differentiation of a myeloid cell to a granulocyte or a neutrophil. Other differentiation based disorders, such as AML and APL, as well as cancers in general which feature improperly differentiated cells over proliferating, can be regulated and induced into proper differentiation by administering or contacting the abnormally differentiated cell with a securinine and/or a norsecurinine derivative as described herein. These methods further include selecting a subject in need based on diagnosis of improperly differentiating cells and administering a therapeutically effective amount of securinine and/or norsecurinine derivative(s).

The present invention also provides, in part, for treating cancer cells in general by administering to or contacting a cancerous cell with a securinine and/or norsecurinine derivative as described herein to thereby inhibit proliferation and/or cause cancer cell death. The securinine and norsecurinine analogs have demonstrated themselves to be also effective in inhibiting myeloid growth as well as encouraging myeloid differentiation which leads to the irreversible growth arrest of the cells (see Table 1). Further, as demonstrated in the Examples and as set forth in Table 2, the analogs of the present invention have shown efficacy in inhibiting acute myelocytic leukemia cell growth, colon cancer cell growth and ovarian cancer cell growth. Contacting or administering to a cancer cell or to a subject with cancer a securinine or norsecurinine derivative as described herein, in a therapeutically effective amount, provides for reduced proliferation and cell death of the cell or the cancerous cells of the subject. The present invention provides for methods of treating or ameliorating myeloid disorders by contacting or administering to a subject or a cell, such as a myeloid cell or regulating cell thereof or precursor thereof, the securinine and/or norsecurinine analogs of the present invention. Myeloid disorders are understood in the art and may include acute myeloid leukemia, chronic myeloid leukemia, myeloid proliferative dysplasias, myelodysplastic syndrome, myelodysplastic/myeloproliferative neoplasias (MDS/MPN), myeloid and lymphoid neoplasias together with eosinophilia and abnormalities of PDGFRA, PDGFRB and FGFR1, chronic myeloid leukemia (CML), polycythaemia vera (PV), essential thrombocytosis (ET), primary myelofibrosis (PMF), chronic eosinophilic leukemia (CEL), systematic mastocytosis (SM), and myeloproliferative neoplasias not to be classified (MPN-U). Those skilled in the art will appreciate that myeloid disorders may be detected through the presence or expression of biomarkers, such as on the basis of a clonal marker (Philadelphia chromosome/BCR-ABL fused gene). Further, the molecular basics of myeloid disorders may not be because of a single molecular defect, but within a multi-level process, for example, the a JAK2 mutation, activated tyrosine kinase PDGFR-A, PDGFR-B or FGFR1, or mutations of genes of epigenetic active proteins like TET2, EZH2, CBL (see, e.g. www.kim2.uniklinikum-jena.de/en/KIM+II/Haematology+and+Medical+Oncology/Consultation+Center+for+Myeloid+Di seases.html).

The present invention also provides for methods of treating inflammatory or immune disorders in a subject comprising contacting a subject with the securinine and/or norsecurinine analogs described herein. Securinine and/or securinine analogs can be used to stimulate monocytes that can lead to an enhancement of the immune response (see, e.g., Shipman et al. 2012, PLoS ONE 7(9): e41278. doi: 10.1371/journal.pone.0041278). One use of this enhanced immune response is to assist the subject in controlling infections with pathogens.

The present invention provides for methods of treating a condition as described herein with less adverse additional effects. As is known in the art, securinine antagonizes the $GABA_A$ receptor. The securinine and/or norsecurinine analogs may demonstrate reduced binding/antagonizing of the receptor (see, e.g. Neganova et al., Neurochem J. (2001) 5(3): 208-214). Unlike securinine which causes seizures in mice due to GABA receptor binding, none of the C14 or C15 substituted analogues cause seizures in mice at high doses (up to 100 mg/kg)

The present invention provides for methods of using the securinine and/or norsecurinine analogs as an adjuvant. As is known in the art, an adjuvant refers to an agent that modifies the pharmacological effect or immunological effect of another agent. Adjuvants are frequently used in administered vaccines to subvert the immune response. Adjuvants can also stabilize formulations. Securinine is documented as stimulating monocytes through acting upon the $GABA_A$ receptor. Thus, the invention provides for administering the securinine and norsecurinine analogs as an immune adjuvant along with an antigen from which a desired vaccination is directed, such as dengue fever, polio, measles, mumps, rubella, distemper, small pox, chicken pox, shingles, ebola, HIV, anthrax, diphtheria, HBV, HPV, influenza, hepatitis (A and B), encephalitis, meningococcal, pertussis, pneumococcal, rabies, typhoid, tetanus, and yellow fever.

The present invention further provides for methods of treating pathogens. Securinine is identified as a $GABA_A$ receptor antagonist with inhibitory activity against *Toxoplasma gondii* growth (Holmes et al. 2011 Exp. Parisitol. 127:370-375). Thus, the present invention provides for methods of inhibiting pathogen growth by contacting a pathogen with the securinine and/or norsecurinine analogs described herein.

Examples

Synthesis of Non-Reduced Analogs

In another variation, γ-iodo derivative of securinine (C14-iodo derivative of securinine, INVS-MG-52A) can be prepared from securinine using N-iodosuccinimide in MeOH (Reported, *Tetrahedron* 2012, 68, 3972-3979). During the product isolation from the reaction mixture, side products INVS-MG-52B and INVS-MG-52D also isolated. Using the intermediates INVS-MG-52A and -52B, further C-14 analogs of securinine can be prepared as outlined below.

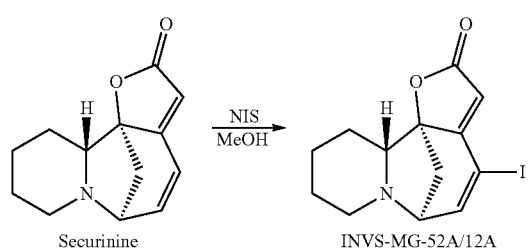

Securinine → INVS-MG-52A/12A (NIS / MeOH)

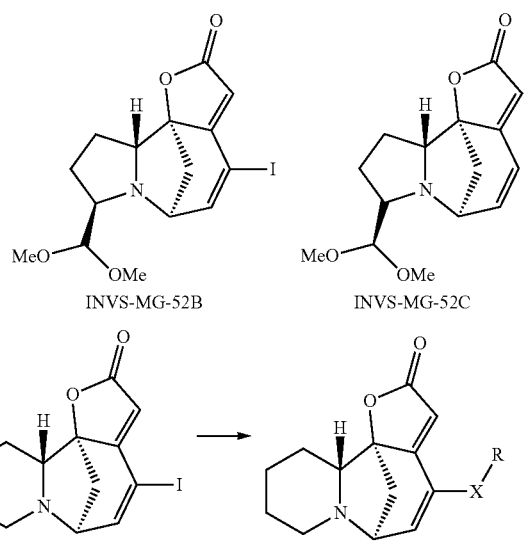

INVS-MG-52B, INVS-MG-52C

X = C—C, C=C, C≡C
R = alkyl, alkenyl, alkynyl, heteroatom, etc.,

In one variation, the process comprising the synthesis of C-14 alkyl/aryl analogs of securinine can be prepared using INVS-MG-52A and the corresponding boronic acids/esters as outlined below.

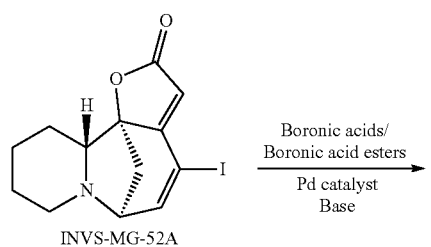

INVS-MG-52A → (Boronic acids/Boronic acid esters, Pd catalyst, Base)

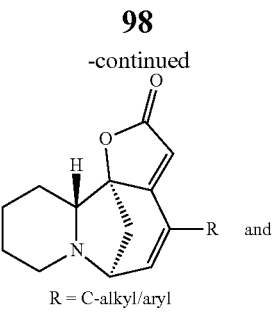

R = C-alkyl/aryl and

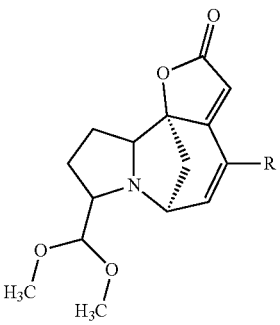

C-14 Alkyl/Aryl Analogs of Securinine:

Bis(triphenylphosphine)palladium(II)dichloride (7 mg, 0.01 mmol) was added to a stirred solution of INVS-MG-52A (34.3 mg, 0.1 mmol) in anhydrous toluene or tetrahydrofuran (0.75 ml) followed by the corresponding boronic acid (0.2 mmol) and then potassium carbonate/water (20 mg, 0.15 mmol/75 uL). The reaction mixture was degassed under nitrogen atmosphere for 15 minutes and then gradually heated to 80° C. to 100° C. The reaction progress was monitored by TLC and the reaction mixture was stirred at that temperature for 1 to 2 h until the starting material was completely consumed. The reaction mixture was poured in water (2 ml) and extracted with ethylacetate (2×3 ml) and the combined organic layers were washed with brine (5 ml), dried over sodium sulfate and concentrated on the rotary evaporator. The crude product was dried under high vacuum and purified by silica gel chromatography using appropriate solvent system to afford the desired C-14 alkyl/aryl analog of securinine in 40-70% yield. The following C-14 alkyl/aryl analogs of securinine have been synthesized employing the above. All the compounds were characterized by 1H NMR.

INVS-MG-56A

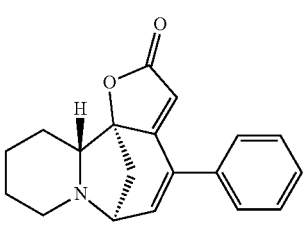

INVS-MG-54B

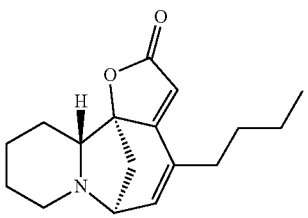

-continued

INVS-MG-63B

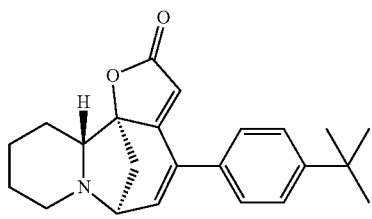

INVS-MG-64A

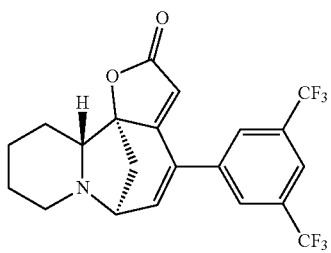

INVS-MG-65B

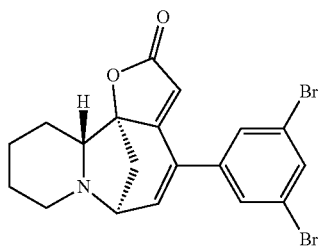

In another variation, the process comprising the synthesis of C-14 alkynyl analogs of securinine can be prepared using INVS-MG-52A and the corresponding terminal alkynes as outlined below.

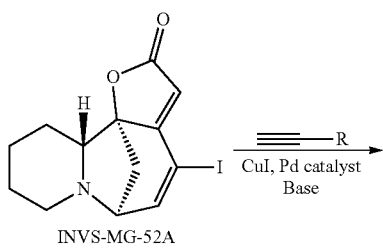

INVS-MG-52A

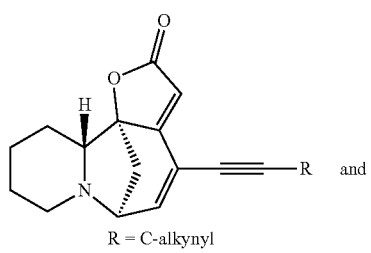

R = C-alkynyl

-continued

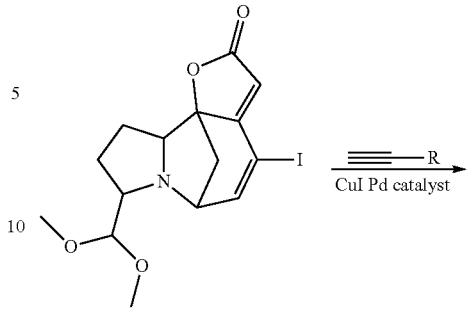

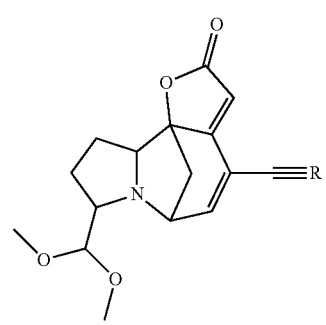

C-14 Alkynyl Analogs of Securinine:

To a solution of INVS-MG-52A (26 mg, 0.075 mmol) in anhydrous 1,4-dioxane/tetrahydrofuran (0.75 ml) was added bis(triphenylphosphine)palladium(II)dichloride (2.6 mg, 0.00375 mmol), CuI (1.5 mg, 0.0075 mmol) and tryethylamine (52 uL, 0.375 mmol). The reaction mixture was degassed under nitrogen atmosphere for 10 minutes and then gradually heated to 80° C. At this point, the reaction mixture turned into homogeneous, clear, dark brown solution. Heating removed to bring the reaction mixture to room temperature, and the corresponding alkyne (0.1125 mmol) was added. The reaction progress was monitored by TLC and the reaction mixture was stirred at that temperature for 1 to 2 h until the starting material was completely consumed. The reaction mixture was poured in water (2 ml) and extracted with ethylacetate (2×3 ml) and the combined organic layers were washed with brine (5 ml), dried over sodium sulfate and concentrated on the rotary evaporator. The crude product was dried under high vacuum and purified by silica gel chromatography using appropriate solvent system to afford the corresponding C-14 alkynyl analog of securinine. The following C-14 alkynyl analogs of securinine have been synthesized employing the above procedure in good yields (50-90%). All the compounds were characterized by 1H NMR.

INVS-MG-108B

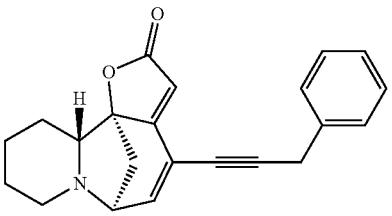

and

INVS-MG-109-IIA
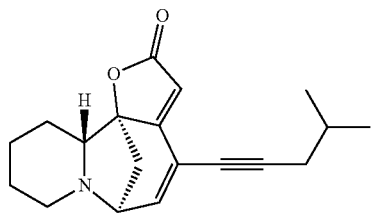
INVS-MG-110B
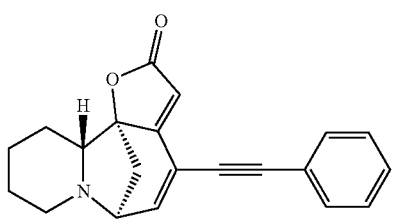
INVS-MG-111B
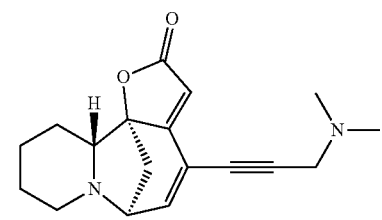
INVS-MG-113A
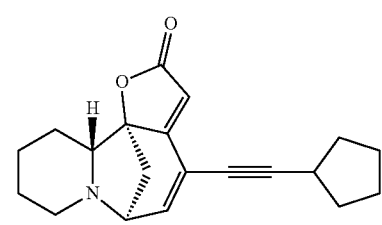
INVS-MG-117B
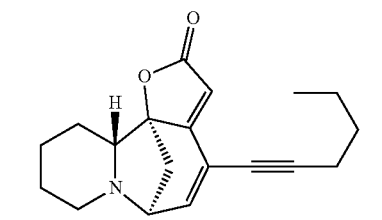
INVS-MG-118B
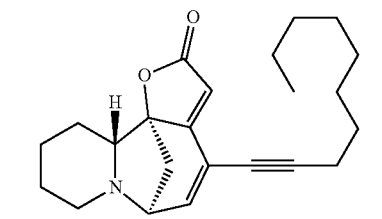
INVS-MG-120A
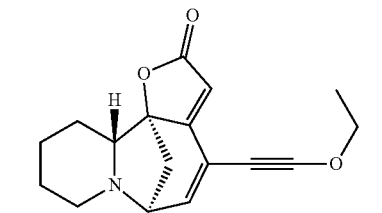
INVS-MG-121A
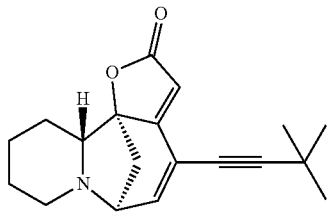
INVS-MG-123B
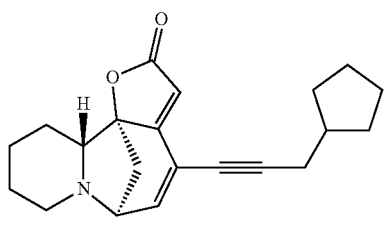
INVS-MG-124A
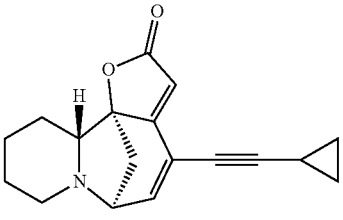
INVS-MG-125A
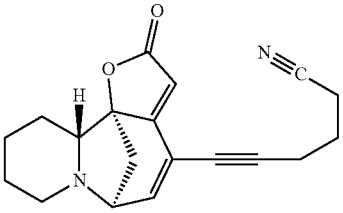
INVS-MG-131A
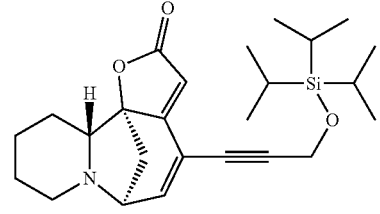
INVS-MG-132A
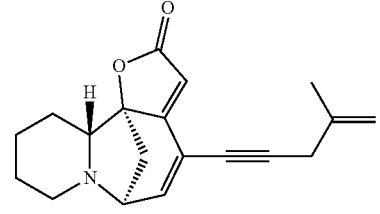
INVS-MG-134C
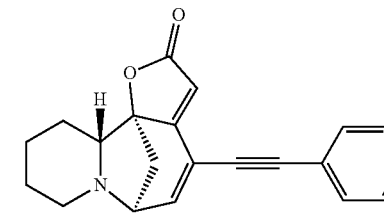

INVS-MG-135B
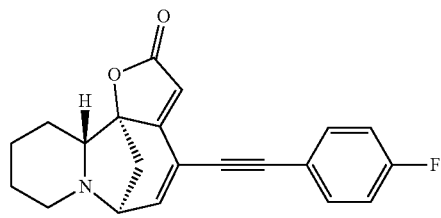
INVS-MG-145A
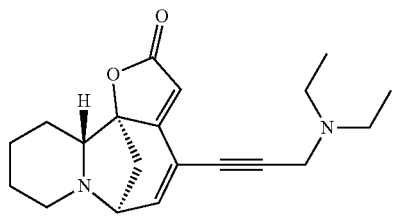 [SMILES: CCN(CC)CC#CC1=C[C@@H]2C[C@@]3(OC(=O)C=C13)[C@H]1CCCCN21]
INVS-MG-136B
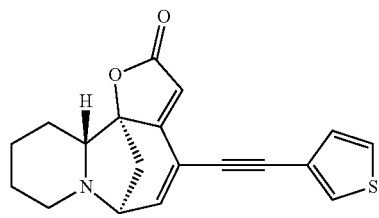
INVS-MG-146B
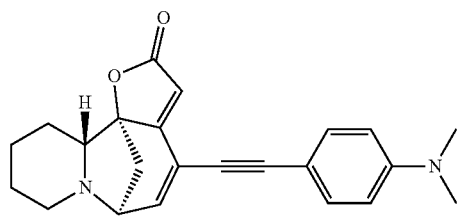
INVS-MG-133B
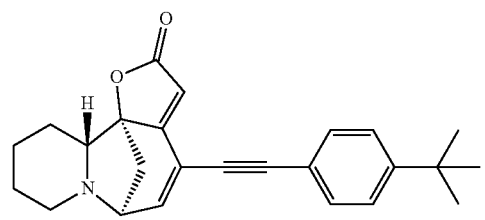
INVS-MG-150B
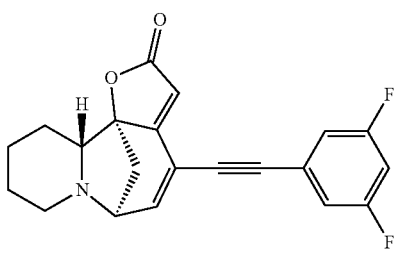
INVS-MG-133B
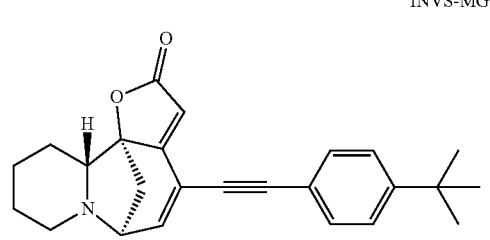
INVS-MG-151B
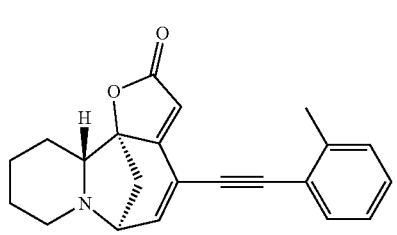
INVS-MG-137B
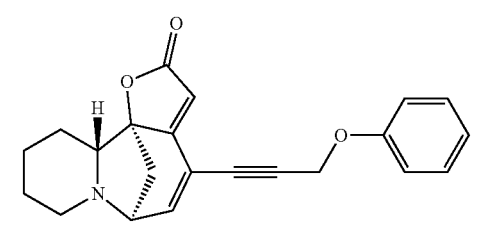
INVS-MG-152A
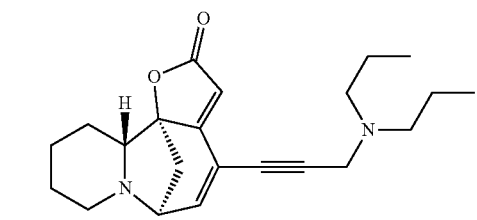
INVS-MG-138B
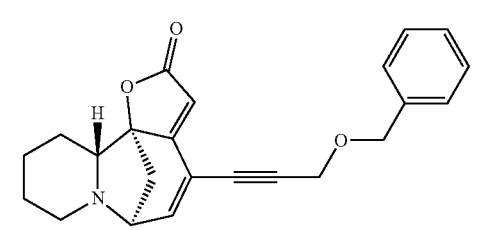
INVS-MG-157B
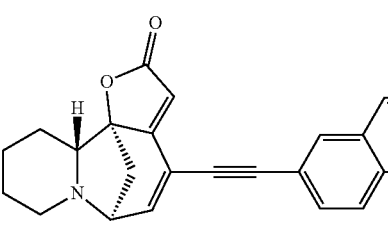

INVS-MG-158B
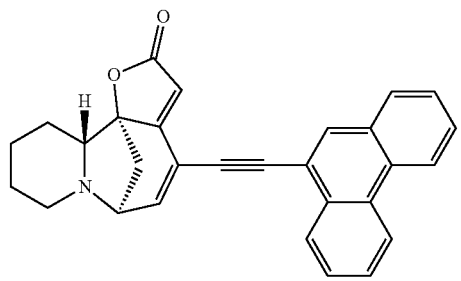
INVS-MG-165B
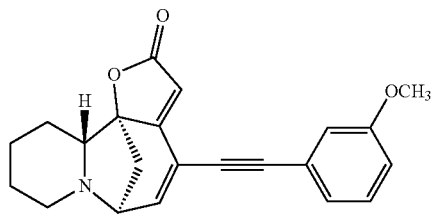
INVS-MG-159A
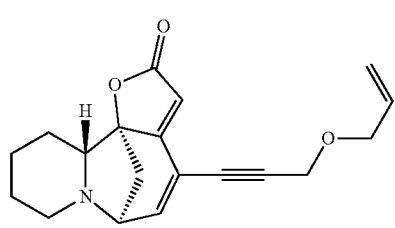
INVS-MG-166B
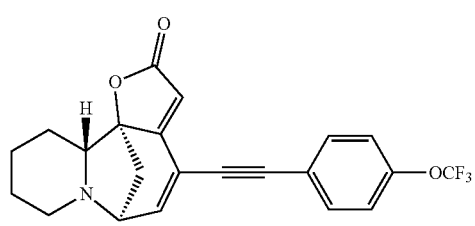
INVS-MG-160B
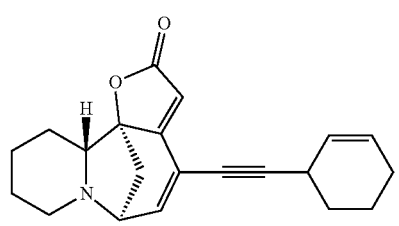
INVS-MG-167B
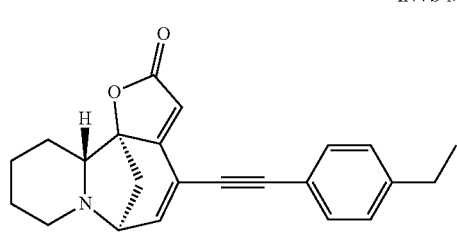
INVS-MG-161B
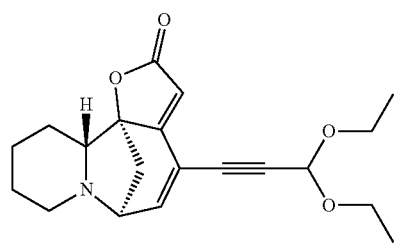
INVS-MG-168B
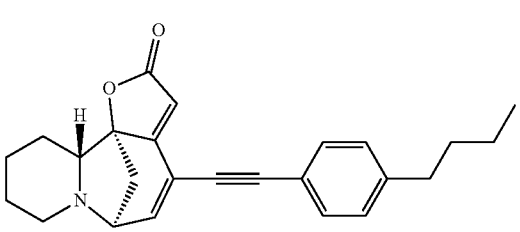
INVS-MG-162B
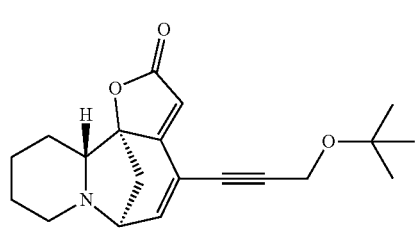
INVS-MG-169B
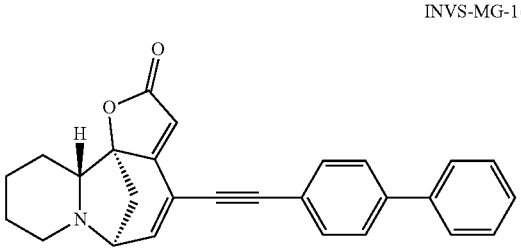
INVS-MG-164B
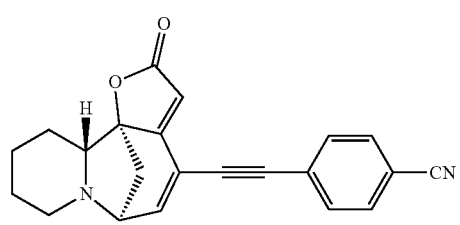
INVS-MG-170B
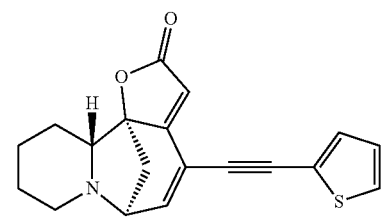

INVS-MG-175A

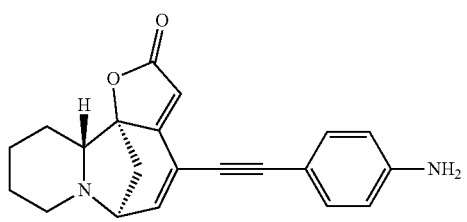

INVS-MG-193B

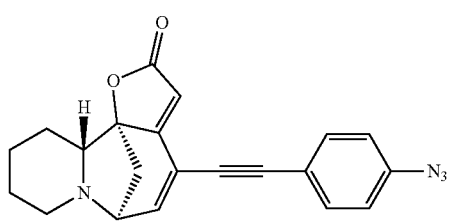

Preparation of Pharmaceutically Useful Salts:

In another variation, the process comprising the synthesis of various pharmaceutically useful salts can be prepared from the corresponding securinine analogs as outlined below.

Securinine analog (0.1 mmol) was dissolved in 1,4-dioxane (0.5 ml) and 2N HCl/1,4-dioxane solution was added to the reaction mixture at 0° C. The reaction mixture was stirred for 30 minutes to 2 hours at 0° C. as the product slowly precipitated. 1 ml of hexanes or ether was added and the solids were filtered, washed with 1 ml of hexanes/ether to obtain the corresponding HCl salt.

Securinine analog (0.1 mmol) was dissolved in methanol and tartaric acid (0.1 mmol) was added. The reaction mixture was gradually heated to 80° C. for several hours as the product slowly precipitated. 1 ml of ether was added and the solids were filtered, washed with 1 ml of ether to obtain the corresponding tartarate salt.

The following various pharmaceutically useful salts of securinine analogs have been prepared and characterized by 1H NMR

INVS-MG-70

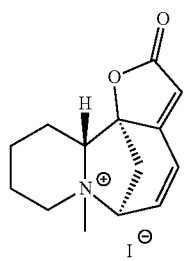

INVS-MG-72

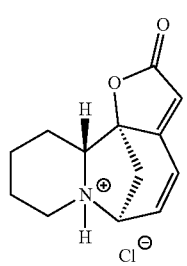

INVS-MG-83

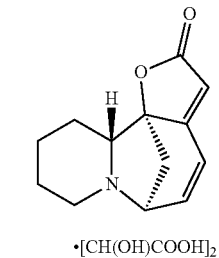

·[CH(OH)COOH]$_2$

INVS-MG-71

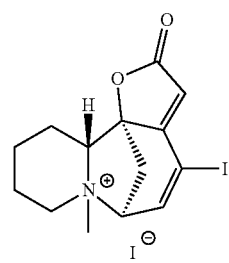

INVS-MG-73

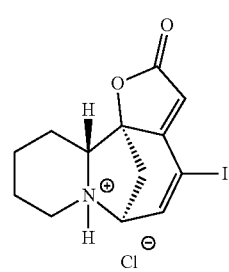

INVS-MG-84

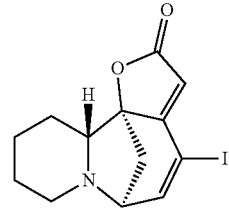

·[CH(OH)COOH]$_2$

INVS-MG-111-IV

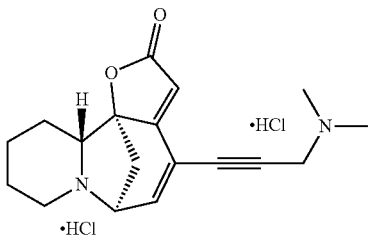

INVS-MG-125-III

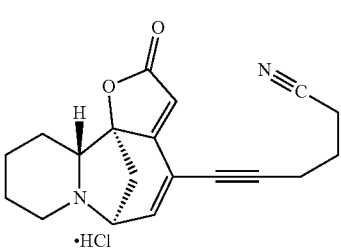

INVS-MG-157-III
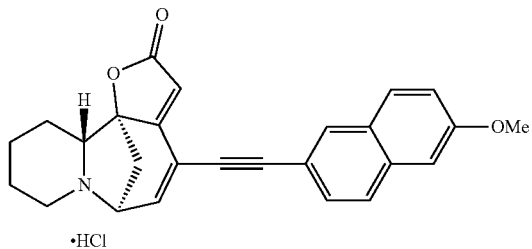
·HCl
INVS-MG-158-III
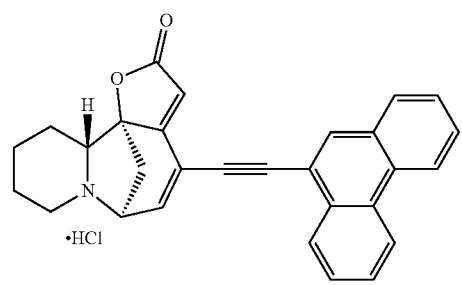
·HCl
INVS-MG-169-III
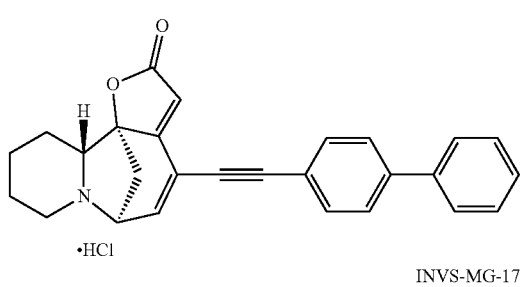
·HCl
INVS-MG-170-III
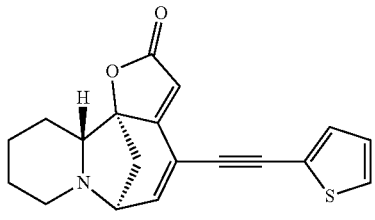
·HCl
INVS-MG-146-III
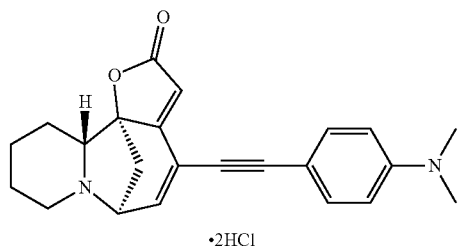
·2HCl
INVS-MG-152-III
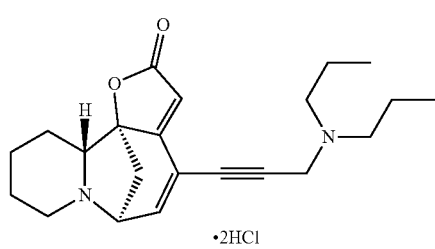
·2HCl
INVS-MG-175-V
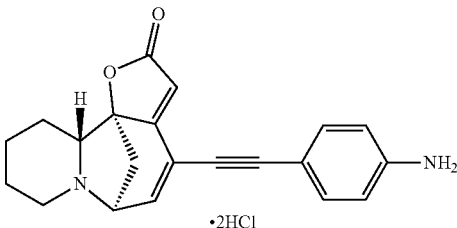
·2HCl
INVS-MG-193-III
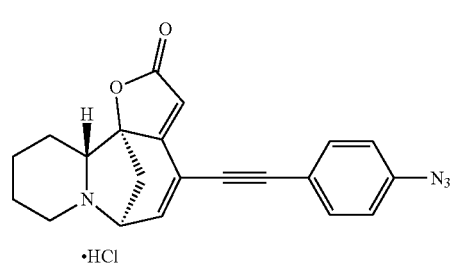
·HCl
INV-SZ-113-2
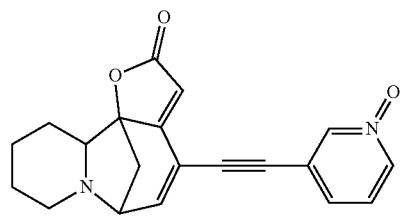
INV-SZ-114-1
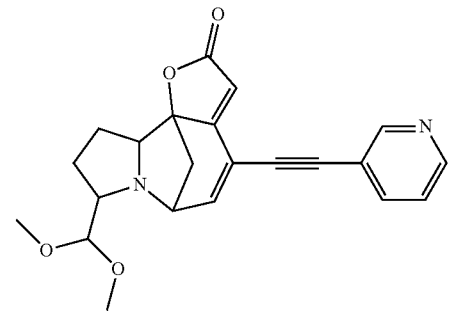
INV-SZ-115-1
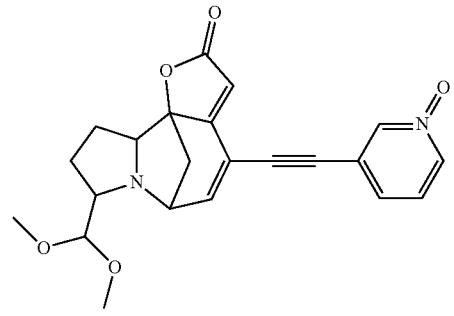

-continued
INV-SZ-116-1
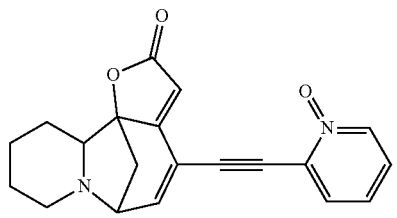
INV-SZ-117-2
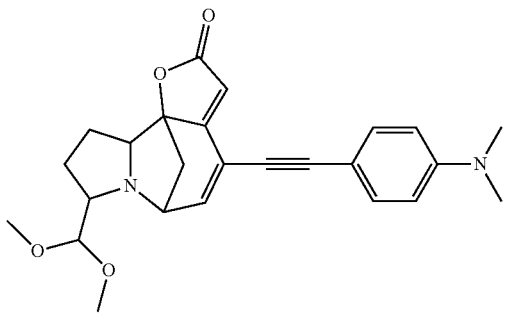
INV-SZ-118-2
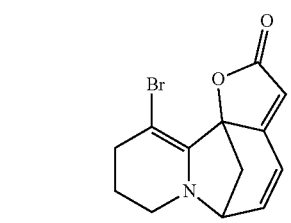
INV-SZ-120-1
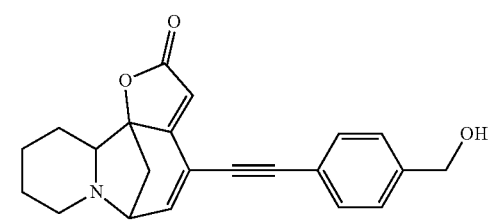
INV-SZ-121-1
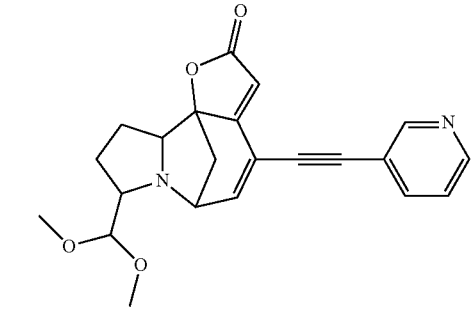
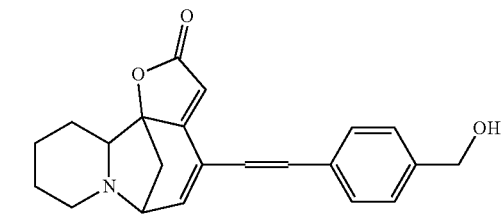
-continued
INV-SZ-122-1
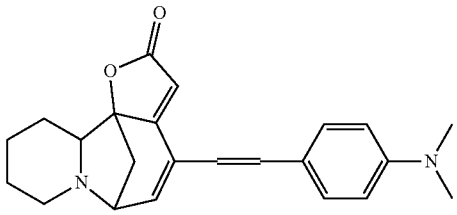
INV-SZ-123-2
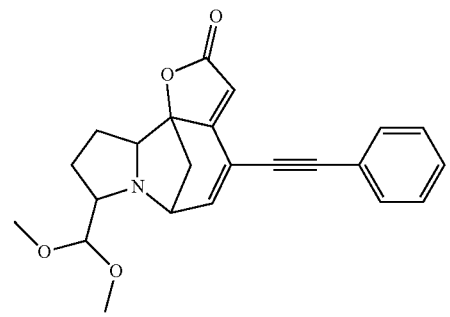
INV-SZ-123-3
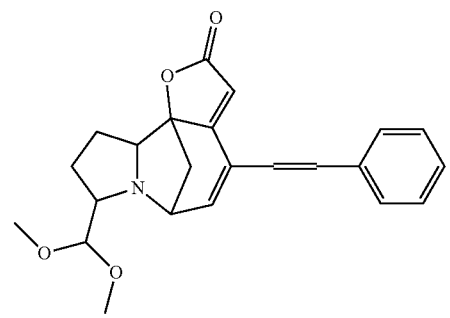
INV-SZ-125-1
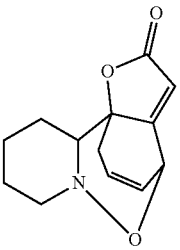
INV-SZ-125-2
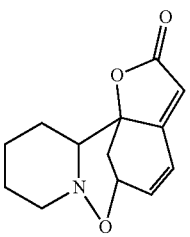

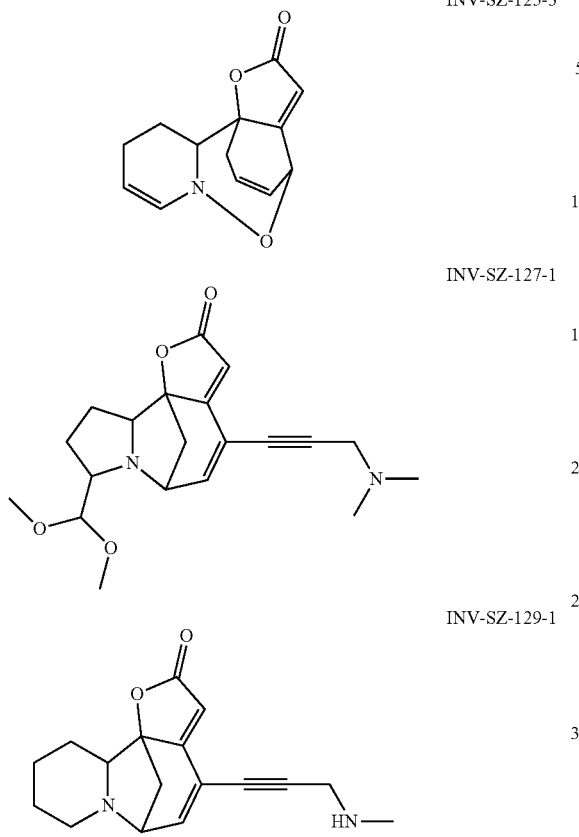

INV-SZ-125-3

INV-SZ-127-1

INV-SZ-129-1

C-15 Reduced Analogs

C-15 reduced analogs of securinine were prepared. C-15 analogs of securinine can be prepared by 1,6-conjugate addition of thials/amines following the general procedure outlined below.

54.3 mg of securinine (0.25 mmol) and 0.3-0.4 mmol of the corresponding amine/thial were weighed in an oven dried reaction flask equipped with a septa or a 4 ml vial with a Teflon cap. 1 ml of acetonitrile followed by tryethylamine (139 uL, 1 mmol) was added and the reaction mixture was stirred under nitrogen atmosphere at room temperature. The reaction mixture was monitored by TLC. The reaction mixture was allowed to stir about 8 h to 2 days at room temperature until the starting material was completely consumed or maximum product formation was observed. All the volatiles in the reaction mixture were evaporated under reduced pressure and the crude product was purified by flash column chromatography on silica gel, using appropriate hexanes/acetone solvent system. The following C-15 analogs of securinine have been synthesized employing the above procedure in good yields (55-95%). All the compounds were characterized by 1H NMR.

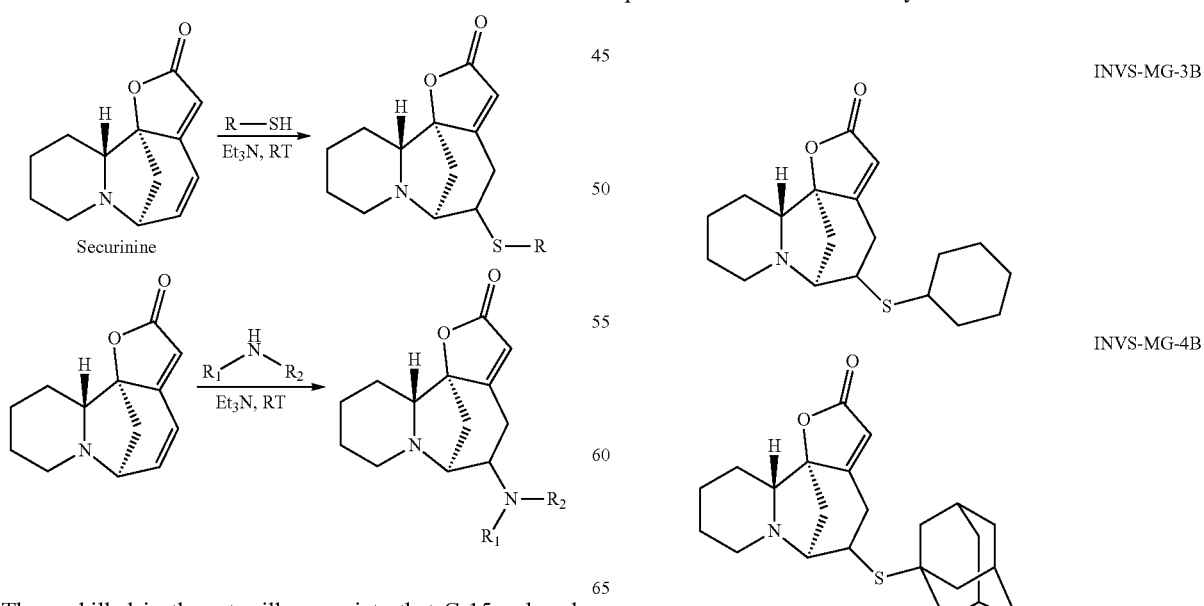

Those skilled in the art will appreciate that C-15 reduced analogs can be similarly prepared using norsecurinine:

INVS-MG-5C
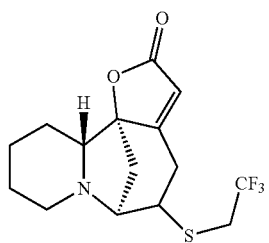
INVS-MG-9A
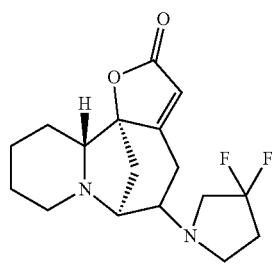
INVS-MG-14B
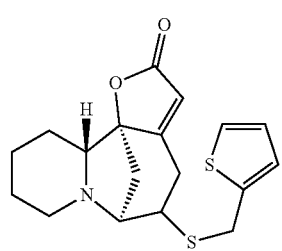
INVS-MG-16A
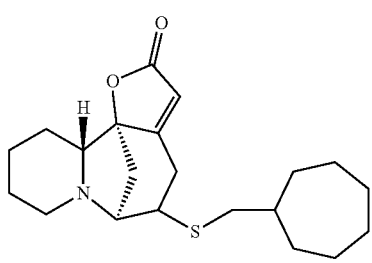
INVS-MG-19A
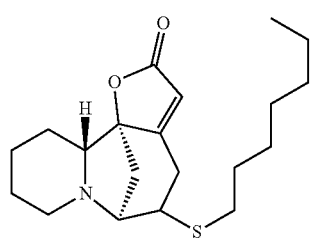
INVS-MG-20B
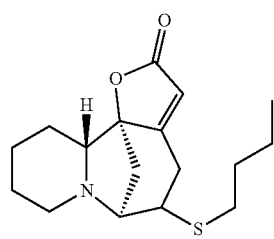
INVS-MG-21B
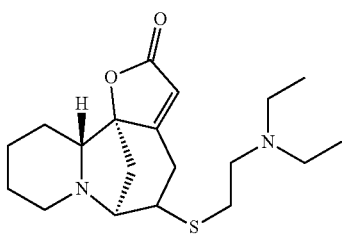
INVS-MG-34B/INV-2B
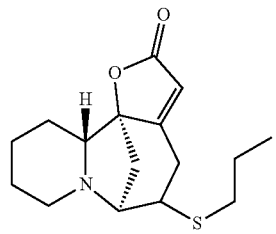
INVS-MG-37B/INV-26C
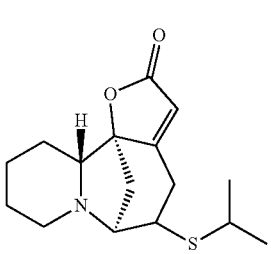
INVS-MG-57B
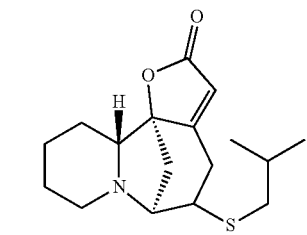
INVS-MG-105C
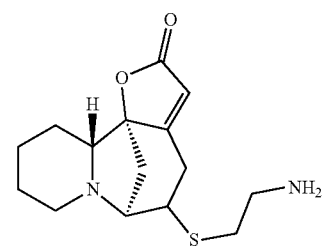
INVS-MG-106B
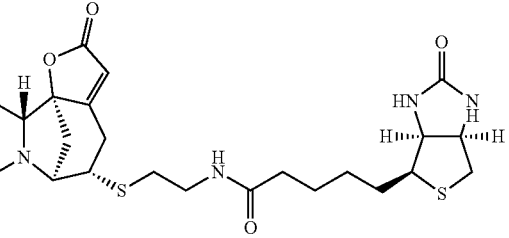

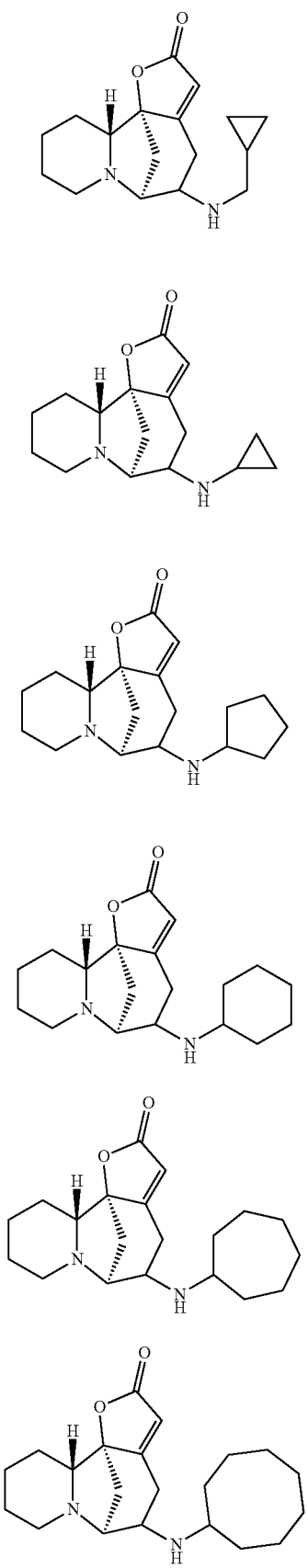
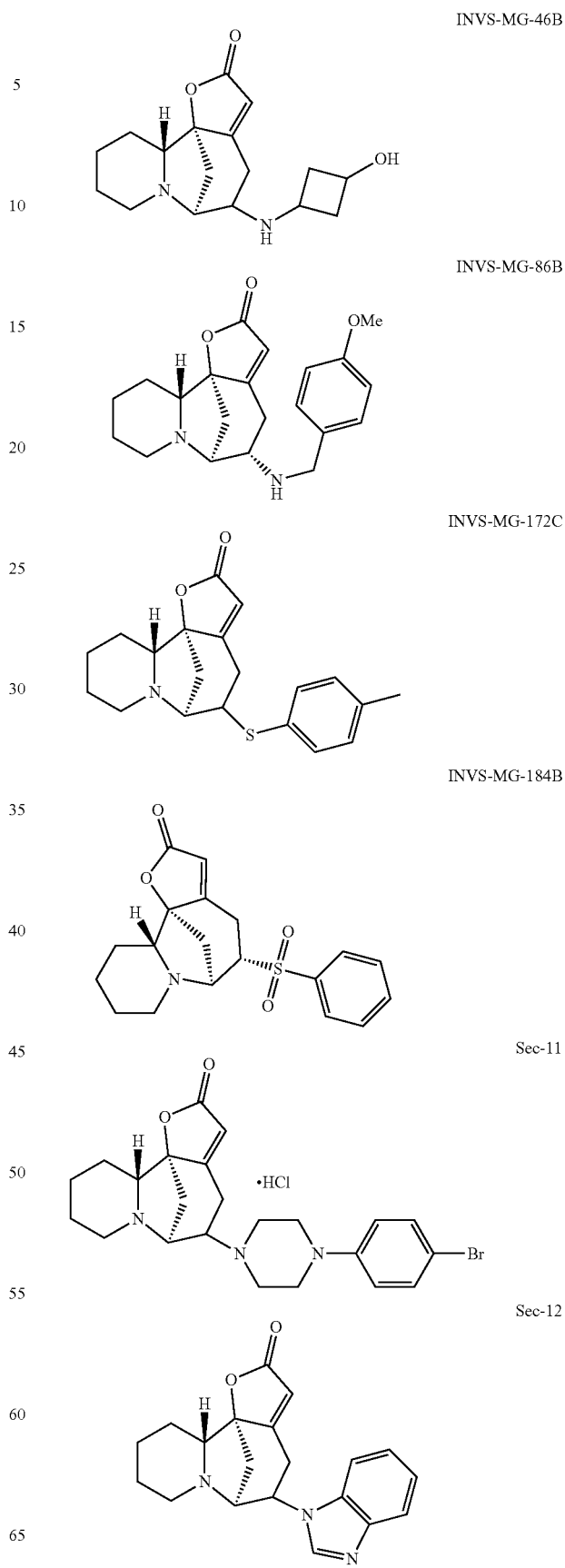

119
-continued
Sec-13
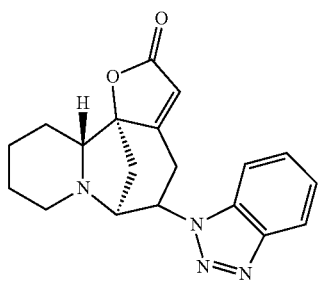
INV₂A
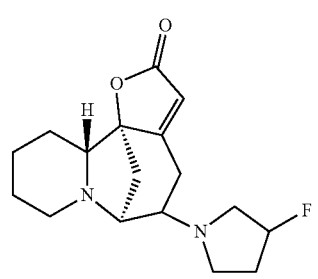
Sec 2
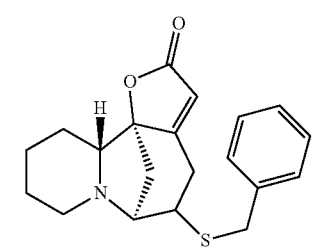
Sec 4
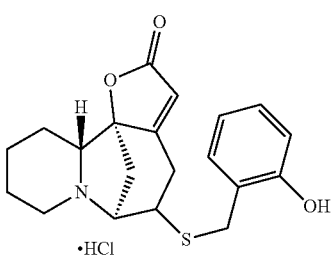
Sec 5
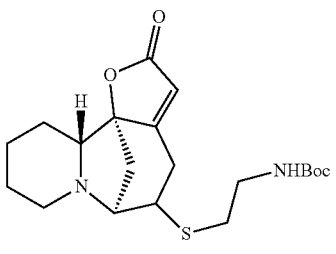
Sec 8
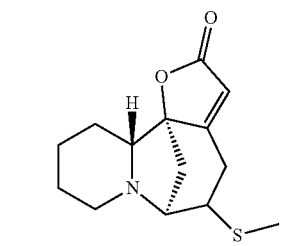
120
-continued
Sec 6
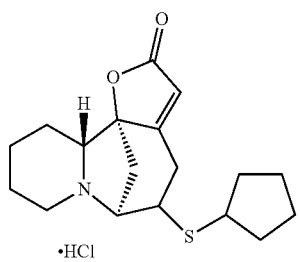
•HCl
Sec 9
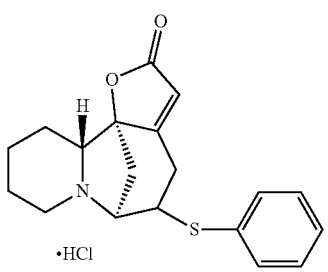
•HCl
Sec 15
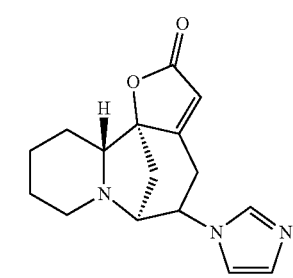
Sec 17
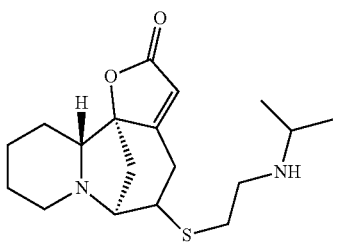
INVS-MG-98B
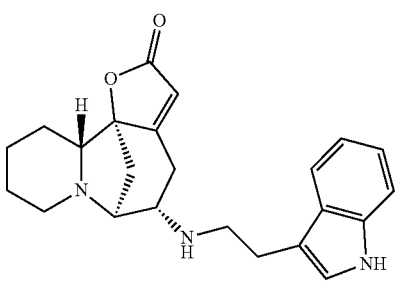
Securinine and Norsecurinine Analogs Efficacy Against Cancer Cells
The analogs were then tested and evaluated on the ability to affect differentiation and growth of HL60 cells. Represented compound biological data are displayed in Table 1:

TABLE 1

| Sample code | Structure | M. Wt | HL-60, Dif50/IC50 |
| --- | --- | --- | --- |
| Securinine | 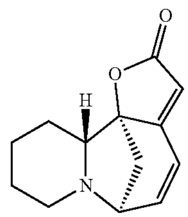 [SMILES: O=C1C=C2C=C[C@@H]3C[C@@]2(O1)[C@H]1CCCCN31] | 217.26 | 10 < Dif50 < 15 |
| INV-2B (INVS-MG-34B) | 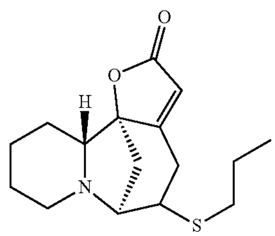 [SMILES: CCCSC1CC2=CC(=O)O[C@@]23C[C@@H]1N1CCCC[C@@H]13] | 293.42 | 15 < Dif50 < 20 |
| INV-26C (INVS-MG-37B) | 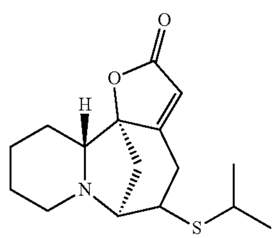 [SMILES: CC(C)SC1CC2=CC(=O)O[C@@]23C[C@@H]1N1CCCC[C@@H]13] | 293.42 | 15 < Dif50 < 20 |
| INVS-MG-3B | 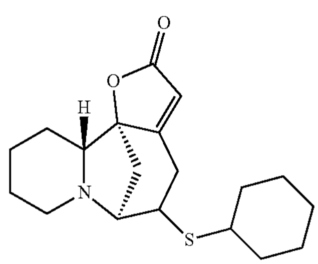 [SMILES: O=C1C=C2CC(SC3CCCCC3)[C@@H]3C[C@@]2(O1)[C@H]1CCCCN31] | 333.49 | 15 < Dif50 < 20 |
| INVS-MG-4B | 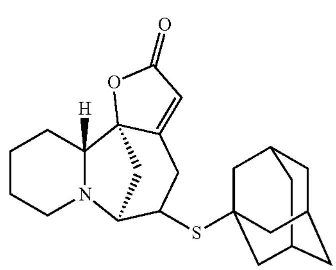 [SMILES: O=C1C=C2CC(SC34CC5CC(CC(C5)C3)C4)[C@@H]3C[C@@]2(O1)[C@H]1CCCCN31] | 385.56 | 30 < Dif50 |
| INVS-MG-5A | 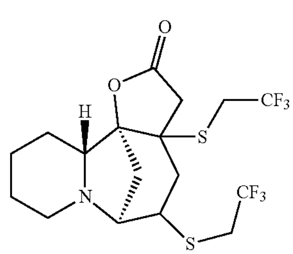 [SMILES: O=C1CC2(SCC(F)(F)F)CC(SCC(F)(F)F)[C@@H]3C[C@@]2(O1)[C@H]1CCCCN31] | 449.47 | 5 < Dif50 < 7.5 |

TABLE 1-continued

| Sample code | Structure | M. Wt | HL-60, Dif50/IC50 |
|---|---|---|---|
| INVS-MG-5B | 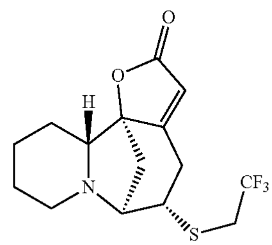 [SMILES: O=C1C=C2C[C@H](SCC(F)(F)F)[C@@H]3C[C@@]2(O1)[C@H]1CCCCN31] | 333.37 | 30 < Dif50 |
| INVS-MG-5C | 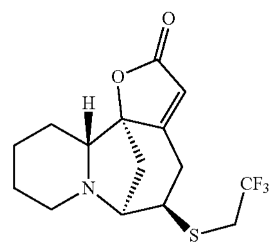 [SMILES: O=C1C=C2C[C@@H](SCC(F)(F)F)[C@@H]3C[C@@]2(O1)[C@H]1CCCCN31] | 333.37 | 20 < Dif50 < 30 |
| INVS-MG-7C | 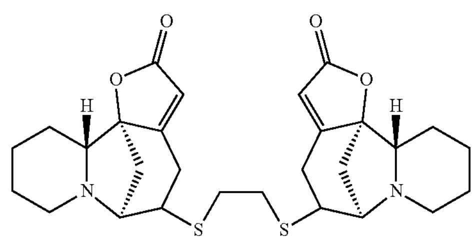 [SMILES: O=C1C=C2CC(SCCSC3CC4=CC(=O)O[C@]45C[C@H]3N3CCCC[C@H]35)[C@@H]3C[C@@]2(O1)[C@H]1CCCCN31] | 528.53 | 10 < Dif50 < 15 |
| INVS-MG-9A | 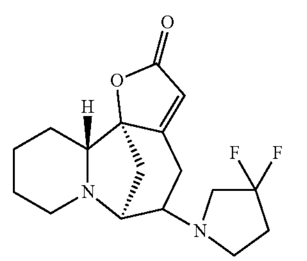 [SMILES: O=C1C=C2CC(N3CCC(F)(F)C3)[C@@H]3C[C@@]2(O1)[C@H]1CCCCN31] | 324.37 | 30 < Dif50 |
| INVS-MG-12A | 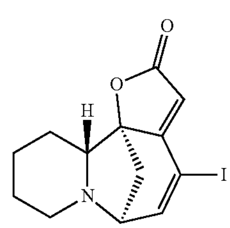 [SMILES: O=C1C=C2C(I)=C[C@@H]3C[C@@]2(O1)[C@H]1CCCCN31] | 343.16 | 0.5 < Dif50 < 0.75 |
| INVS-MG-14B | 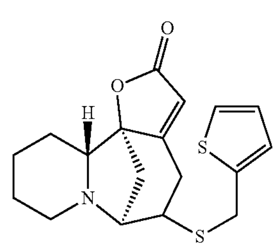 [SMILES: O=C1C=C2CC(SCc3cccs3)[C@@H]3C[C@@]2(O1)[C@H]1CCCCN31] | 347.49 | 20 < Dif ≤ 30 |

TABLE 1-continued

| Sample code | Structure | M. Wt | HL-60, Dif50/IC50 |
| --- | --- | --- | --- |
| INVS-MG-16A | 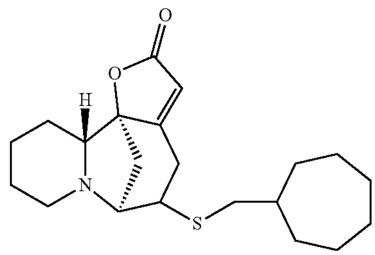 [SMILES: O=C1C=C2CC(SCC3CCCCCC3)[C@@H]3C[C@@]2(O1)[C@H]1CCCCN31] | 361.54 | 10 < Dif50 < 15 |
| INVS-MG-19A | 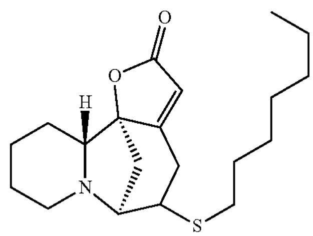 [SMILES: CCCCCCCSC1CC2=CC(=O)O[C@@]23C[C@@H]1N1CCCC[C@@H]13] | 349.53 | 20 < Dif50 < 30 |
| INVS-MG-20B | 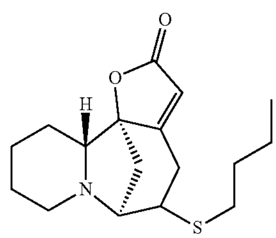 [SMILES: CCCCSC1CC2=CC(=O)O[C@@]23C[C@@H]1N1CCCC[C@@H]13] | 307.45 | 20 < Dif50 < 30 |
| INVS-MG-21B | 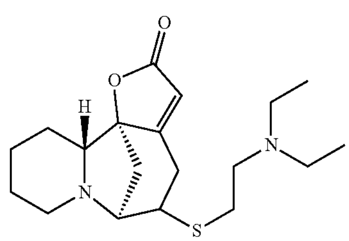 [SMILES: CCN(CC)CCSC1CC2=CC(=O)O[C@@]23C[C@@H]1N1CCCC[C@@H]13] | 350.52 | 10 < Dif < 15 |
| INVS-MG-25B | 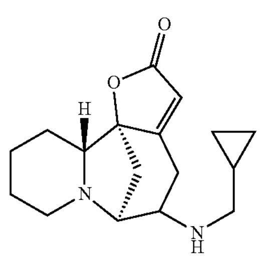 [SMILES: O=C1C=C2CC(NCC3CC3)[C@@H]3C[C@@]2(O1)[C@H]1CCCCN31] | 288.38 | 10 < Dif50 < 15 |
| INVS-MG-26A | 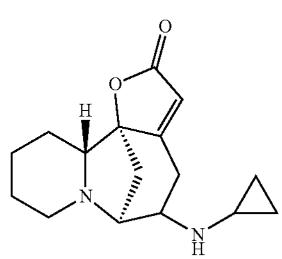 [SMILES: O=C1C=C2CC(NC3CC3)[C@@H]3C[C@@]2(O1)[C@H]1CCCCN31] | 274.36 | 20 < Dif50 < 30 |

TABLE 1-continued

| Sample code | Structure | M. Wt | HL-60, Dif50/IC50 |
|---|---|---|---|
| INVS-MG-27B | 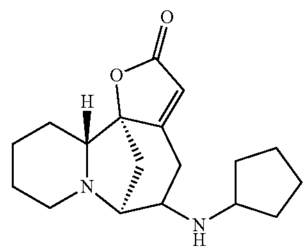 [SMILES: O=C1C=C2CC(NC3CCCC3)[C@@H]3C[C@@]2(O1)[C@H]1CCCCN31] | 302.41 | 10 < Dif50 < 15 |
| INVS-MG-28B | 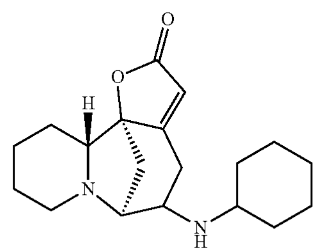 [SMILES: O=C1C=C2CC(NC3CCCCC3)[C@@H]3C[C@@]2(O1)[C@H]1CCCCN31] | 316.44 | 15 < Dif50 < 20 |
| INVS-MG-29A | 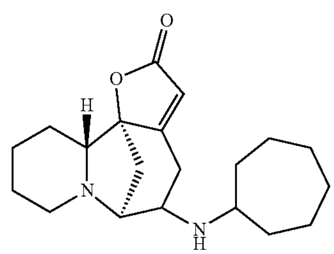 [SMILES: O=C1C=C2CC(NC3CCCCCC3)[C@@H]3C[C@@]2(O1)[C@H]1CCCCN31] | 330.46 | 30 < Dif50 |
| INVS-MG-30A | 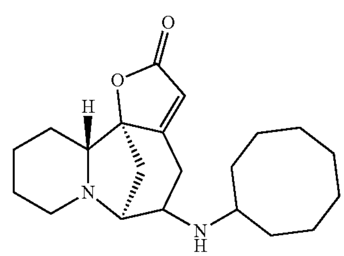 [SMILES: O=C1C=C2CC(NC3CCCCCCC3)[C@@H]3C[C@@]2(O1)[C@H]1CCCCN31] | 344.49 | 30 < Dif50 |
| Sec-1 | 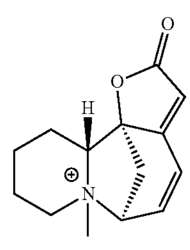 [SMILES: C[N+]12CCCC[C@@H]1[C@]13C[C@H]2C=CC1=CC(=O)O3] | 232.3 | 30 < Dif50 |
| Sec-2 | 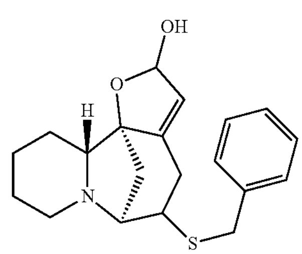 [SMILES: OC1C=C2CC(SCc3ccccc3)[C@@H]3C[C@@]2(O1)[C@H]1CCCCN31] | 343.48 | 30 < Dif50 |

TABLE 1-continued

| Sample code | Structure | M. Wt | HL-60, Dif50/IC50 |
|---|---|---|---|
| Sec-3 | 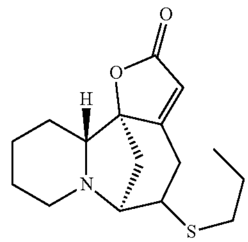 [SMILES: CCCSC1CC2=CC(=O)O[C@@]23C[C@@H]1N1CCCC[C@@H]13] | 293.42 | 10 < Dif50 < 15 |
| Sec-4 | ·HCl | 395.94 | 15 < Dif50 < 20 |
| Sec-5 | 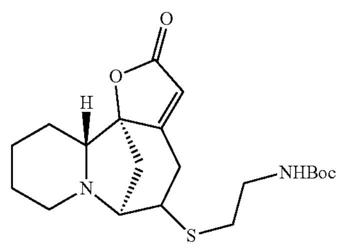 [SMILES: CC(C)(C)OC(=O)NCCSC1CC2=CC(=O)O[C@@]23C[C@@H]1N1CCCC[C@@H]13] | 394.53 | 15 < Dif50 < 20 |
| Sec-6 | ·HCl | 357.94 | 15 < Dif50 < 20 |
| Sec-7 | 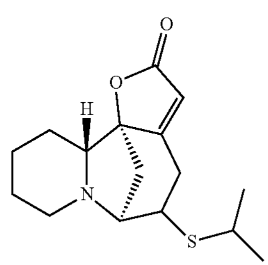 [SMILES: CC(C)SC1CC2=CC(=O)O[C@@]23C[C@@H]1N1CCCC[C@@H]13] | 293.42 | 15 < Dif50 < 20 |
| Sec-8 | 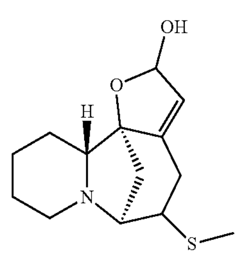 [SMILES: CSC1CC2=CC(O)O[C@@]23C[C@@H]1N1CCCC[C@@H]13] | 267.39 | 10 < Dif50 < 15 |

TABLE 1-continued
| Sample code | Structure | M. Wt | HL-60, Dif50/IC50 |
|---|---|---|---|
| Sec-9 | 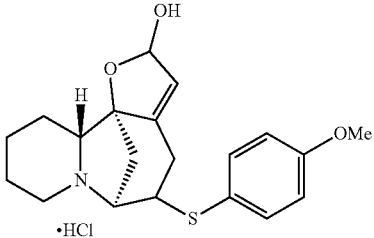 [SMILES: COc1ccc(SC2CC3=CC(O)O[C@@]34C[C@@H]2N2CCCC[C@@H]24)cc1 ; Cl] | 395.94 | 20 < Dif50 < 30 |
| Sec-11 | 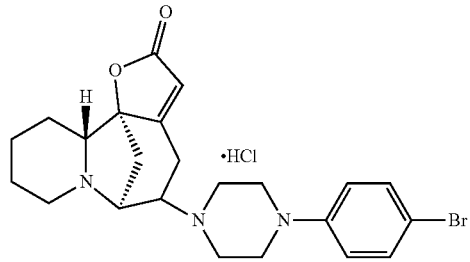 [SMILES: O=C1C=C2CC(N3CCN(c4ccc(Br)cc4)CC3)[C@@H]3C[C@@]2(O1)[C@H]1CCCCN31 ; Cl] | 494.85 | 15 < Dif50 < 20 |
| Sec-12 | 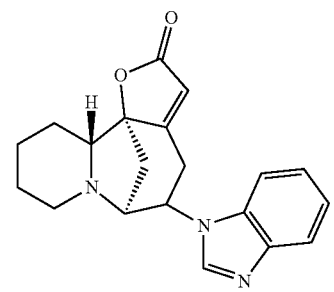 [SMILES: O=C1C=C2CC(n3cnc4ccccc43)[C@@H]3C[C@@]2(O1)[C@H]1CCCCN31] | 335.44 | 30 < Dif50 |
| Sec-13 | 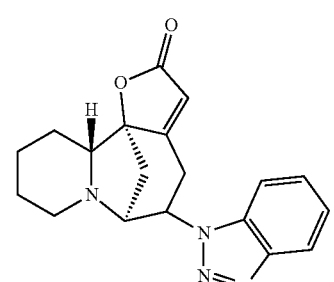 | 336.39 | 20 < Dif50 < 30 |
| Sec-15 | 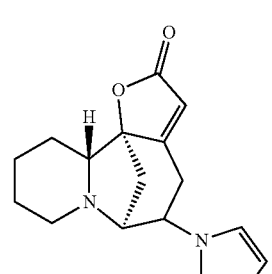 | 285.34 | 15 < Dif50 < 20 |
| Sec-16 | 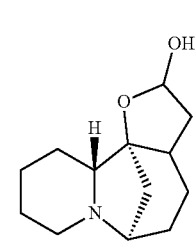 [SMILES: OC1CC2CC[C@@H]3C[C@@]2(O1)[C@H]1CCCCN31] | 223.31 | 20 < Dif50 < 30 |

TABLE 1-continued

| Sample code | Structure | M. Wt | HL-60, Dif50/IC50 |
| --- | --- | --- | --- |
| Sec-17 | 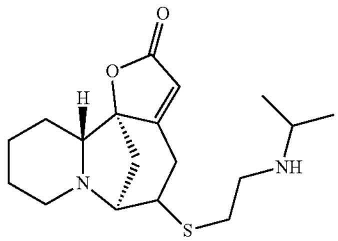 [SMILES: CC(C)NCCSC1CC2=CC(=O)O[C@@]23C[C@@H]1N1CCCC[C@@H]13] | 336.49 | 15 < Dif50 < 20 |
| Sec-18 & Sec-20 | 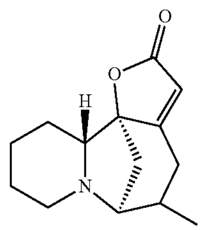 [SMILES: CC1CC2=CC(=O)O[C@@]23C[C@@H]1N1CCCC[C@@H]13] | 233.31 | 20 < Dif50 < 30 |
| Sec-19 | 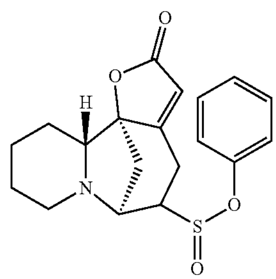 [SMILES: O=C1C=C2CC(S(=O)Oc3ccccc3)[C@@H]3C[C@@]2(O1)[C@H]1CCCCN31] | 359.44 | 20 < Dif50 < 30 |
| Sec-21 | 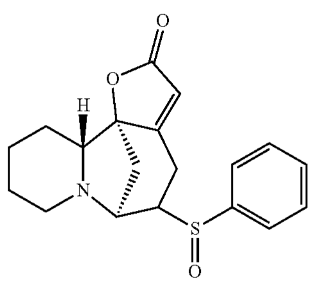 [SMILES: O=C1C=C2CC(S(=O)c3ccccc3)[C@@H]3C[C@@]2(O1)[C@H]1CCCCN31] | 343.44 | 20 < Dif50 < 30 |
| Sec-22 | 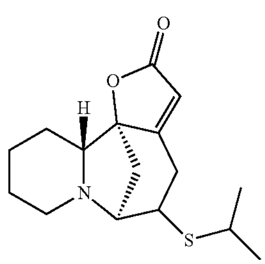 [SMILES: CC(C)SC1CC2=CC(=O)O[C@@]23C[C@@H]1N1CCCC[C@@H]13] | 293.42 | 15 < Dif50 < 20 |
| Sec-23 | 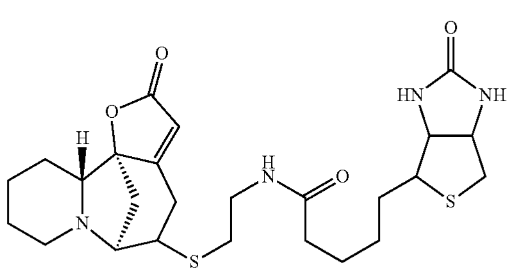 [SMILES: O=C(CCCCC1SCC2NC(=O)NC21)NCCSC1CC2=CC(=O)O[C@@]23C[C@@H]1N1CCCC[C@@H]13] | 520.71 | NT |

TABLE 1-continued

| Sample code | Structure | M. Wt | HL-60, Dif50/IC50 |
|---|---|---|---|
| INVS-MG-46B | 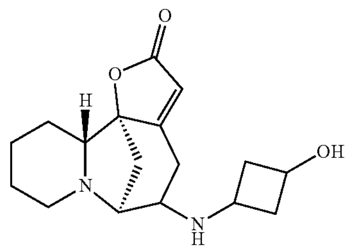 [SMILES: O=C1C=C2CC(NC3CC(O)C3)[C@@H]3C[C@@]2(O1)[C@H]1CCCCN31] | 304.38 | 10 < Dif50 < 15 |
| INVG-27-2 = INVS-MG-52B | | 403.21 | 100% Death < 2.5 |
| INVG-Z-27-4 = INVS-MG-52D | 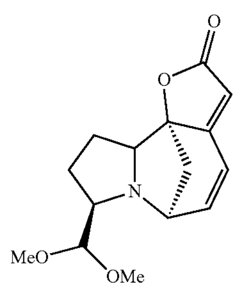 [SMILES: COC(OC)[C@H]1CCC2N1[C@@H]1C=CC3=CC(=O)O[C@@]32C1] | 403.21 | 3.25 < Dif50 < 5 |
| INVG-28-1 = INVS-MG-56B | 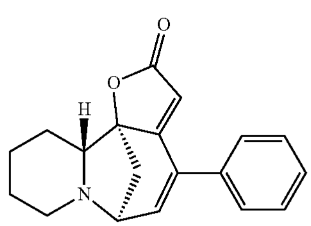 [SMILES: O=C1C=C2C(c3ccccc3)=C[C@@H]3C[C@@]2(O1)[C@H]1CCCCN31] | 293.36 | 30 < Dif50 |
| INVS-MG-54B | 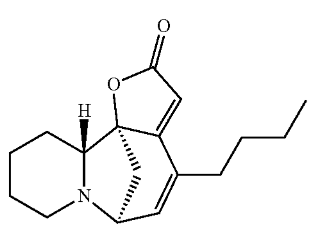 [SMILES: CCCCC1=C[C@@H]2C[C@@]3(OC(=O)C=C13)[C@H]1CCCCN21] | 273.37 | 3 < IC50 < 4 |

TABLE 1-continued

| Sample code | Structure | M. Wt | HL-60, Dif50/IC50 |
|---|---|---|---|
| | | | |
| INVS-MG-57A | | 307.45 | 20 < Dif50 < 30 |
| INVS-MG-55B & 57B = 37B | | 307.45 | 15 < Dif50 < 20 |
| INVS-MG-58C = 34B | 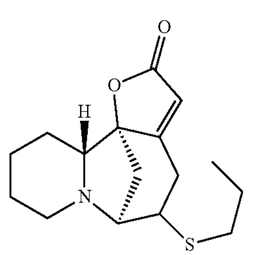 [SMILES: CCCSC1CC2=CC(=O)O[C@@]23C[C@@H]1N1CCCC[C@@H]13] | 293.42 | 15 < Dif50 < 20 |

TABLE 1-continued
| Sample code | Structure | M. Wt | HL-60, Dif50/IC50 |
|---|---|---|---|
| | 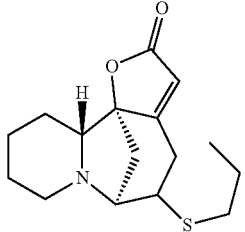 [SMILES: CCCSC1CC2=CC(=O)O[C@@]23C[C@@H]1N1CCCC[C@@H]13] | | |
| INVS-MG-63B | 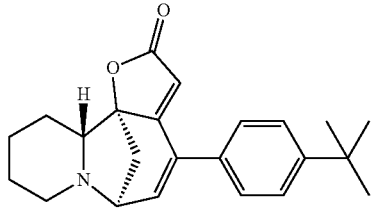 [SMILES: CC(C)(C)c1ccc(C2=C[C@@H]3C[C@@]4(OC(=O)C=C24)[C@H]2CCCCN32)cc1] | 349.47 | 20 < IC50 < 30 |
| INVS-MG-64A | 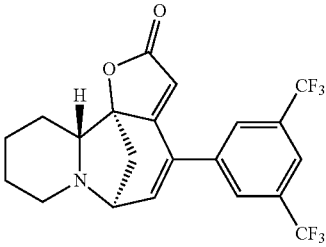 | 429.36 | 15 < IC50 < 20 |
| INVS-MG-65B | 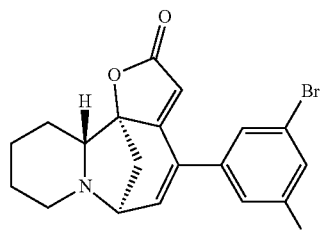 | 451.15 | 15 < IC50 < 20 |
| INVS-MG-70 | 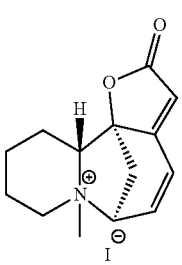 [SMILES: C[N+]12CCCC[C@@H]1[C@]13C[C@H]2C=CC1=CC(=O)O3 ; [I-]] | 359.2 | 30 < Dif50 |
| INVS-MG-71 | 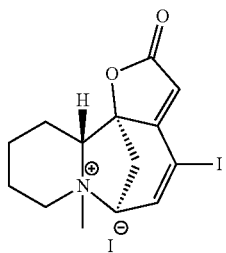 [SMILES: C[N+]12CCCC[C@@H]1[C@]13C[C@H]2C=C(I)C1=CC(=O)O3 ; [I-]] | 485.1 | 5 < IC50 < 7.5 |

TABLE 1-continued

| Sample code | Structure | M. Wt | HL-60, Dif50/IC50 |
| --- | --- | --- | --- |
| INVS-MG-72 = 12A HCl salt | 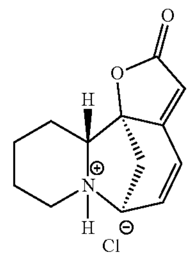 [SMILES: O=C1C=C2C=C[C@@H]3C[C@@]2(O1)[C@H]1CCCC[NH+]31 ; [Cl-]] | 253.72 | 15 < Dif50 < 20 |
| INVS-MG-73 | 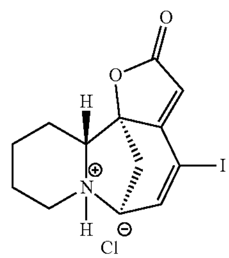 [SMILES: O=C1C=C2C(I)=C[C@@H]3C[C@@]2(O1)[C@H]1CCCC[NH+]31 ; [Cl-]] | 379.62 | 0.25 < IC50 < 0.375 |
| INVS-MG-44 | 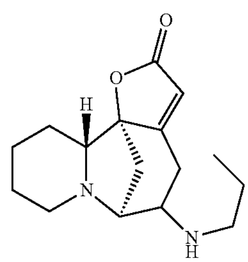 [SMILES: CCCNC1CC2=CC(=O)O[C@@]23C[C@@H]1N1CCCC[C@@H]13] | 276.37 | 15 < Dif50 < 20 |
| INVS-MG-59 | 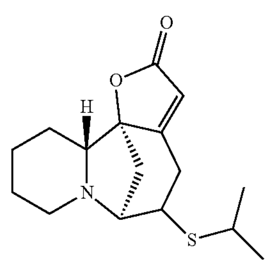 [SMILES: CC(C)SC1CC2=CC(=O)O[C@@]23C[C@@H]1N1CCCC[C@@H]13] | 293.42 | 15 < Dif50 < 20 |
| INVS-MG-60 | 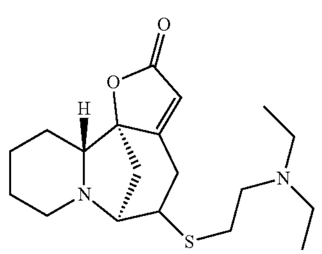 [SMILES: CCN(CC)CCSC1CC2=CC(=O)O[C@@]23C[C@@H]1N1CCCC[C@@H]13] | 350.52 | 15 < Dif50 < 20 |
| INVS-MG-66B | 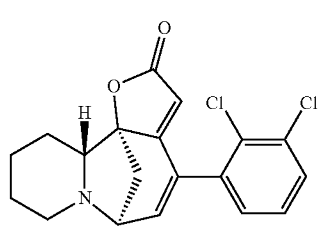 [SMILES: O=C1C=C2C(c3cccc(Cl)c3Cl)=C[C@@H]3C[C@@]2(O1)[C@H]1CCCCN31] | 362.25 | 10 < IC50 < 7.5 |

TABLE 1-continued

| Sample code | Structure | M. Wt | HL-60, Dif50/IC50 |
| --- | --- | --- | --- |
| INVS-MG-74A | 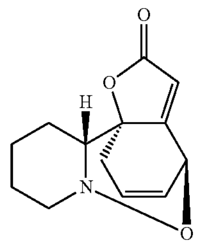 [SMILES: O=C1C=C2[C@@H]3C=CC[C@@]2(O1)[C@H]1CCCCN1O3] | 233.26 | 30 < Dif50 |
| INVS-MG-76-aq | 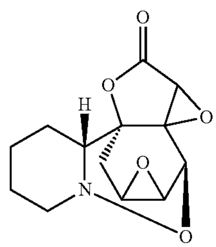 [SMILES: O=C1O[C@]23CC4OC4[C@H](ON4CCCC[C@@H]42)C32OC12] | 265.26 | 30 < Dif50 |
| INVS-MG-82 = 12A HCl salt | 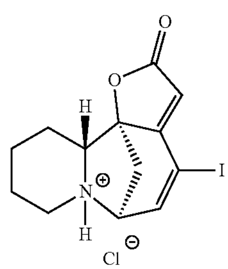 [SMILES: O=C1C=C2C(I)=C[C@@H]3C[C@@]2(O1)[C@H]1CCCC[NH+]31 ; [Cl-]] | 379.62 | 2.5 < IC50 |
| INVS-MG-83 | [CH(OH)COOH]$_2$ | 367.35 | 10 < Dif50 < 15 |
| INVS-MG-84 | [CH(OH)COOH]$_2$ | 493.25 | 2.5 < IC50 |
| INVS-MG-85-IIIB | 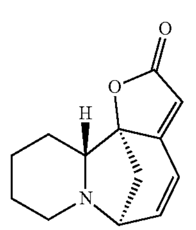 [SMILES: O=C1C=C2C=C[C@@H]3C[C@@]2(O1)[C@H]1CCCCN31] | 216.28 | 15 < Dif50 < 20 |

TABLE 1-continued
| Sample code | Structure | M. Wt | HL-60, Dif50/IC50 |
|---|---|---|---|
| INVS-MG-105C | 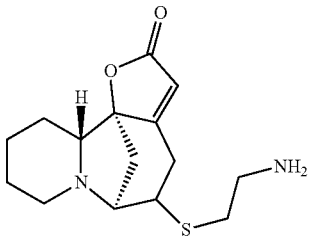 [SMILES: NCCSC1CC2=CC(=O)O[C@@]23C[C@@H]1N1CCCC[C@@H]13] | 294.41 | 10 < Dif50 < 15 |
| INVS-MG-76-II-org | 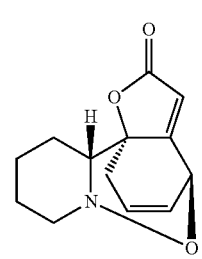 [SMILES: O=C1C=C2[C@@H]3C=CC[C@@]2(O1)[C@H]1CCCCN1O3] | 233.26 | 30 < Dif50 < 20 |
| INVS-MG-77-aq | 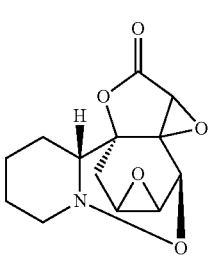 | 265.26 | 30 < Dif50 |
| INVS-MG-86B | 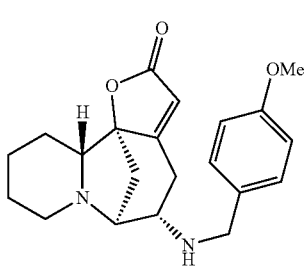 [SMILES: COc1ccc(CN[C@H]2CC3=CC(=O)O[C@@]34C[C@@H]2N2CCCC[C@@H]24)cc1] | 354.44 | 15 < Dif50 < 20 |
| INVS-MG-86C | 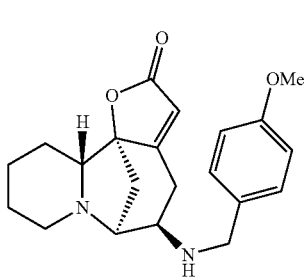 [SMILES: COc1ccc(CN[C@@H]2CC3=CC(=O)O[C@@]34C[C@@H]2N2CCCC[C@@H]24)cc1] | 354.44 | 30 < Dif50 |
| INVS-MG-94-aq | ·HCOOH | 263.29 | 30 < Dif50 |

TABLE 1-continued

| Sample code | Structure | M. Wt | HL-60, Dif50/IC50 |
|---|---|---|---|
| INVS-MG-97-IIB | 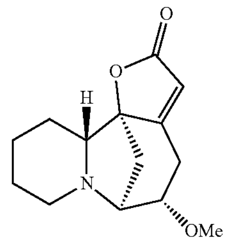 [SMILES: CO[C@H]1CC2=CC(=O)O[C@@]23C[C@@H]1N1CCCC[C@@H]13] | 249.31 | 30 < Dif50 |
| INVS-MG-97-IIE | 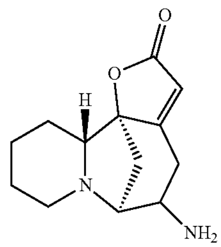 [SMILES: NC1CC2=CC(=O)O[C@@]23C[C@@H]1N1CCCC[C@@H]13] | 234.29 | 20 < Dif50 < 30 |
| INVS-MG-98B | 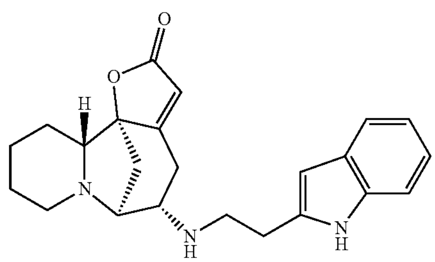 [SMILES: O=C1C=C2C[C@H](NCCc3cc4ccccc4[nH]3)[C@@H]3C[C@@]2(O1)[C@H]1CCCCN31] | 377.48 | 10 < Dif50 < 15 |
| INVS-MG-106B = Sec biotin | 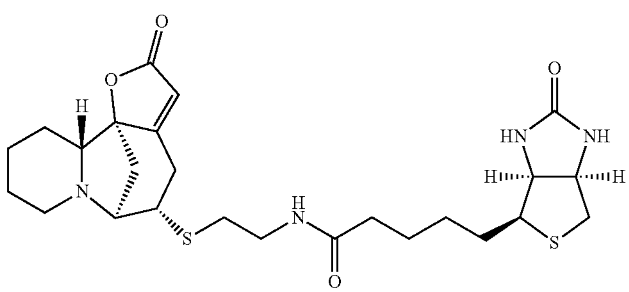 [SMILES: O=C(CCCC[C@@H]1SC[C@@H]2NC(=O)N[C@@H]21)NCCS[C@H]1CC2=CC(=O)O[C@@]23C[C@@H]1N1CCCC[C@@H]13] | 520.71 | 10 < Dif50 < 15 |
| INVS-MG-82-II | 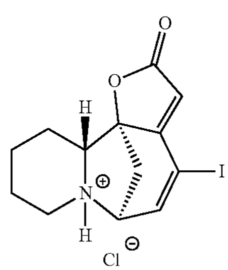 [SMILES: O=C1C=C2C(I)=C[C@@H]3C[C@@]2(O1)[C@H]1CCCC[NH+]31 ; [Cl-]] | 379.62 | 0.156 < IC50 < 0.31 |
| INVS-MG-99B = 52B | 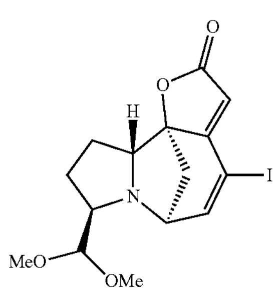 [SMILES: COC(OC)[C@H]1CC[C@H]2N1[C@@H]1C=C(I)C3=CC(=O)O[C@@]32C1] | 403.21 | 0.156 < IC50 < 0.31 |

TABLE 1-continued

| Sample code | Structure | M. Wt | HL-60, Dif50/IC50 |
|---|---|---|---|
| | (structure with iodine substituent) | | |
| INVS-MG-99D = 52D | (structure with MeO, OMe groups) | 277.32 | 0.31 < IC50 < 0.625 |
| INVS-MG-108-IIB | (structure with phenyl alkyne) | 331.41 | 0.31 < IC50 < 0.625 |
| INVS-MG-109-IIA | (structure with isobutyl alkyne) | 297.39 | 1.25 < IC50 < 2.5 |
| INVS-MG-110B | (structure with phenylethynyl) | 317.38 | 0.07 < IC50 < 0.156 |
| INVS-MG-111B | (structure with dimethylaminopropynyl) | 298.38 | 0.07 < IC50 < 0.156 |

TABLE 1-continued

| Sample code | Structure | M. Wt | HL-60, Dif50/IC50 |
|---|---|---|---|
| INVS-MG-113A | 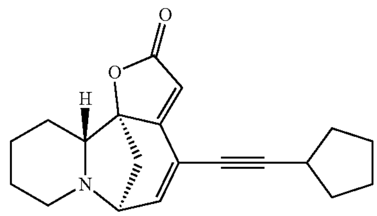 [SMILES: O=C1C=C2C(C#CC3CCCC3)=C[C@@H]3C[C@@]2(O1)[C@H]1CCCCN31] | 309.4 | 0.31 < IC50 < 0.625 |
| INVS-MG-111-III = 111B HCl salt | 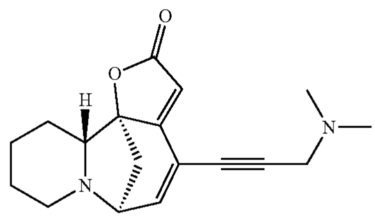 [SMILES: CN(C)CC#CC1=C[C@@H]2C[C@@]3(OC(=O)C=C13)[C@H]1CCCCN21] | 371.3 | 0.07 < IC50 < 0.156 |
| INVS-MG-117B | 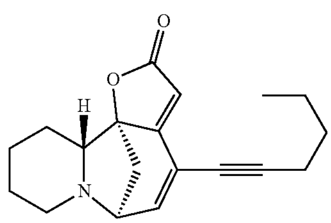 [SMILES: CCCCC#CC1=C[C@@H]2C[C@@]3(OC(=O)C=C13)[C@H]1CCCCN21] | 297.39 | IC50 = 2.5 |
| INVS-MG-120A | 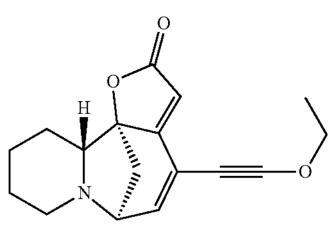 [SMILES: CCOC#CC1=C[C@@H]2C[C@@]3(OC(=O)C=C13)[C@H]1CCCCN21] | 285.34 | 0.31 < IC50 < 0.625 |
| INVS-MG-121A | 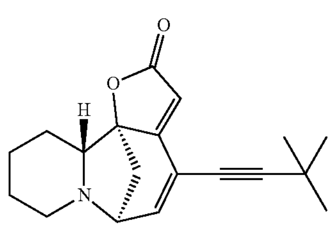 [SMILES: CC(C)(C)C#CC1=C[C@@H]2C[C@@]3(OC(=O)C=C13)[C@H]1CCCCN21] | 297.39 | 125 < IC50 < 25 |
| INVS-MG-123B | 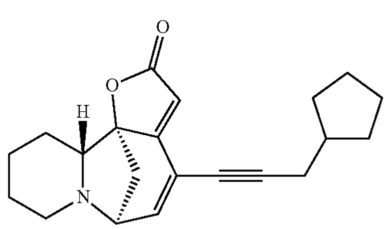 [SMILES: O=C1C=C2C(C#CCC3CCCC3)=C[C@@H]3C[C@@]2(O1)[C@H]1CCCCN31] | 323.43 | 1.25 < IC50 < 2.5 |

TABLE 1-continued

| Sample code | Structure | M. Wt | HL-60, Dif50/IC50 |
| --- | --- | --- | --- |
| INVS-MG-124A | 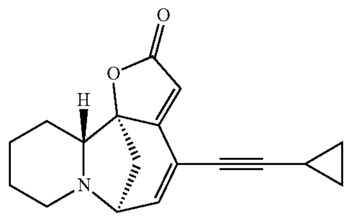 [SMILES: O=C1C=C2C(C#CC3CC3)=C[C@@H]3C[C@@]2(O1)[C@H]1CCCCN31] | 281.35 | 1.25 < IC50 < 2.5 |
| INVS-MG-125A | 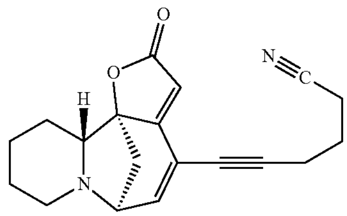 [SMILES: N#CCCCC#CC1=C[C@@H]2C[C@@]3(OC(=O)C=C13)[C@H]1CCCCN21] | 308.37 | 0.31 < IC50 < 0.625 |
| INVS-MG-111-IVB = 111B | 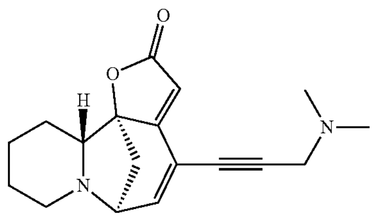 [SMILES: CN(C)CC#CC1=C[C@@H]2C[C@@]3(OC(=O)C=C13)[C@H]1CCCCN21] | 298.38 | 0.07 < IC50 < 0.156 |
| INVS-MG-111-V = 111B HCl salt | 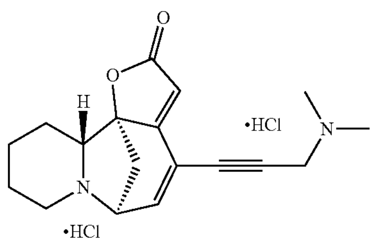 [SMILES: CN(C)CC#CC1=C[C@@H]2C[C@@]3(OC(=O)C=C13)[C@H]1CCCCN21 ; Cl ; Cl] | 371.3 | 0.07 < IC50 < 0.156 |
| INVS-MG-125-IIA = 125A | 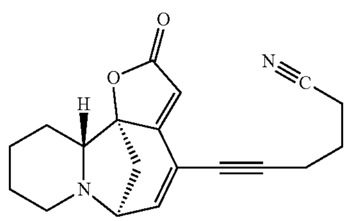 [SMILES: N#CCCCC#CC1=C[C@@H]2C[C@@]3(OC(=O)C=C13)[C@H]1CCCCN21] | 308.37 | 1.25 < IC50 < 2.5 |
| INVS-MG-125-III = 125A HCl salt | 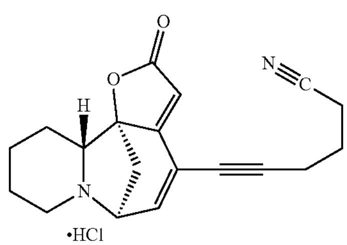 [SMILES: N#CCCCC#CC1=C[C@@H]2C[C@@]3(OC(=O)C=C13)[C@H]1CCCCN21 ; Cl] | 344.85 | 0.625 < IC50 < 1.25 |
| INVS-MG-118-IIB | 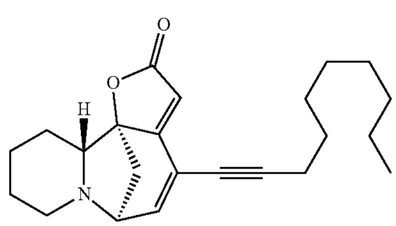 [SMILES: CCCCCCCCC#CC1=C[C@@H]2C[C@@]3(OC(=O)C=C13)[C@H]1CCCCN21] | 353.5 | 2.5 < IC50 < 5 |

TABLE 1-continued

| Sample code | Structure | M. Wt | HL-60, Dif50/IC50 |
|---|---|---|---|
| INVS-MG-131A | 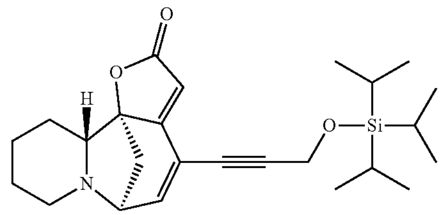 [SMILES: CC(C)[Si](OCC#CC1=C[C@@H]2C[C@@]3(OC(=O)C=C13)[C@H]1CCCCN21)(C(C)C)C(C)C] | 427.65 | 0.625 < IC50 < 1.25 |
| INVS-MG-132A | 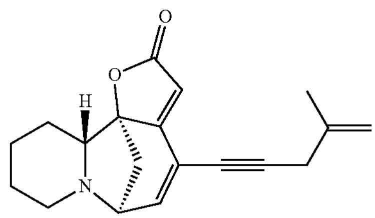 | 295.38 | 0.156 < IC50 < 0.31 |
| INVS-MG-134C | 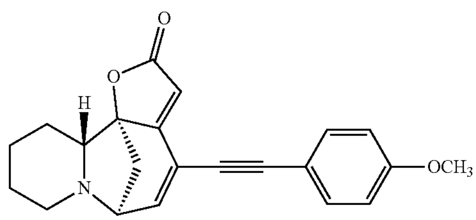 [SMILES: COc1ccc(C#CC2=C[C@@H]3C[C@@]4(OC(=O)C=C24)[C@H]2CCCCN32)cc1] | 347.41 | 0.039 < IC50 < 0.078 |
| INVS-MG-135B | 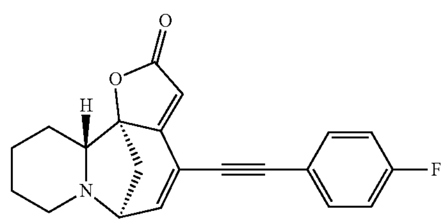 [SMILES: O=C1C=C2C(C#Cc3ccc(F)cc3)=C[C@@H]3C[C@@]2(O1)[C@H]1CCCCN31] | 335.37 | 0.31 < IC50 < 0.625 |
| INVS-MG-136B | 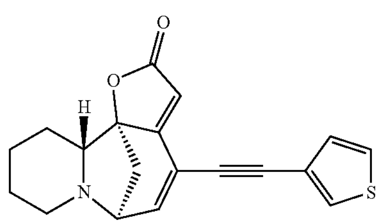 [SMILES: O=C1C=C2C(C#Cc3ccsc3)=C[C@@H]3C[C@@]2(O1)[C@H]1CCCCN31] | 323.41 | 0.156 < IC50 < 0.31 |
| INVS-MG-133B | 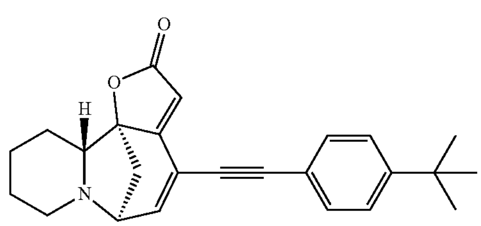 [SMILES: CC(C)(C)c1ccc(C#CC2=C[C@@H]3C[C@@]4(OC(=O)C=C24)[C@H]2CCCCN32)cc1] | 373.49 | IC50 = 1.25 |
| INVS-MG-133-II | 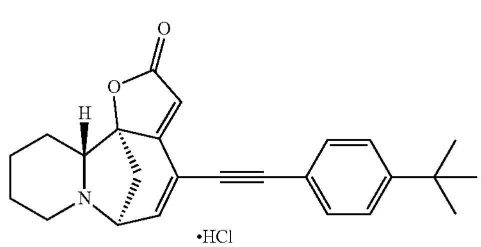 [SMILES: CC(C)(C)c1ccc(C#CC2=C[C@@H]3C[C@@]4(OC(=O)C=C24)[C@H]2CCCCN32)cc1 ; Cl] | 409.95 | 1.25 < IC50 < 2.5 |

TABLE 1-continued
| Sample code | Structure | M. Wt | HL-60, Dif50/IC50 |
|---|---|---|---|
| INVS-MG-137-II | 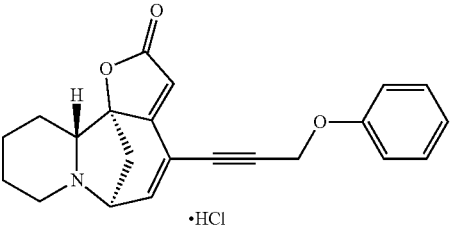 [SMILES: O=C1C=C2C(C#CCOc3ccccc3)=C[C@@H]3C[C@@]2(O1)[C@H]1CCCCN31 ; Cl] | 383.87 | 0.625 < IC50 < 1.25 |
| INVS-MG-138B | 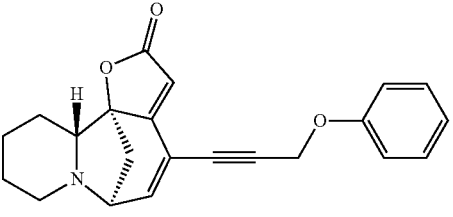 | 361.43 | 1.25 < IC50 < 2.5 |
| INVS-MG-145A | 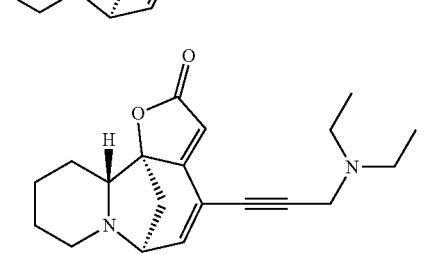 | 326.43 | 0.07 < IC50 < 0.156 |
| INVS-MG-145-II | 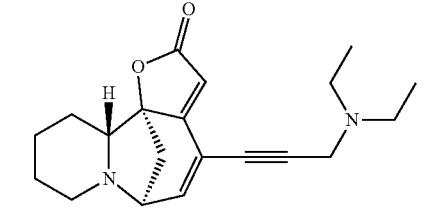 [SMILES: CCN(CC)CC#CC1=C[C@@H]2C[C@@]3(OC(=O)C=C13)[C@H]1CCCCN21] | 399.35 | 0.625 < IC50 < 1.25 |
| INVS-MG-146B | 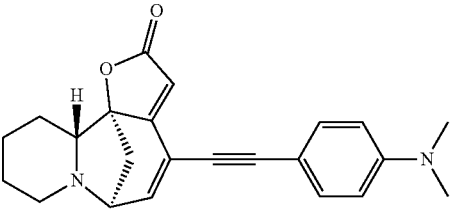 | 360.45 | 0.156 < IC50 < 0.31 |
| INVS-MG-146-II | 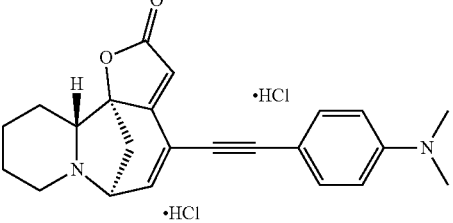 | 433.37 | 0.31 < IC50 < 0.625 |

TABLE 1-continued

| Sample code | Structure | M. Wt | HL-60, Dif50/IC50 |
| --- | --- | --- | --- |
| INVS-MG-150B | 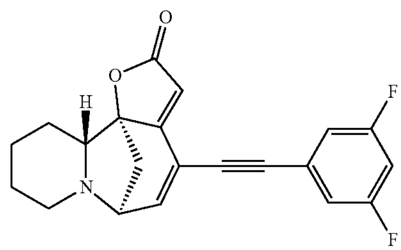 [SMILES: O=C1C=C2C(C#Cc3cc(F)cc(F)c3)=C[C@@H]3C[C@@]2(O1)[C@H]1CCCCN31] | 353.36 | 5 < IC50 < 10 |
| INVS-MG-151B | 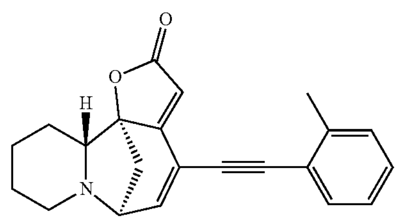 [SMILES: Cc1ccccc1C#CC1=C[C@@H]2C[C@@]3(OC(=O)C=C13)[C@H]1CCCCN21] | 331.41 | 1.25 < IC50 < 2.5 |
| INVS-MG-152A | 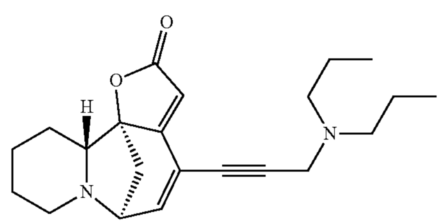 [SMILES: CCCN(CC#CC1=C[C@@H]2C[C@@]3(OC(=O)C=C13)[C@H]1CCCCN21)CCC] | 354.49 | 0.07 < IC50 < 0.156 |
| INVS-MG-119A | 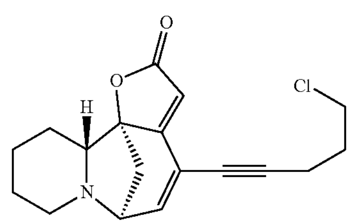 [SMILES: O=C1C=C2C(C#CCCCCl)=C[C@@H]3C[C@@]2(O1)[C@H]1CCCCN31] | 317.81 | 0.625 < IC50 < 1.25 |
| INVS-MG-119B | 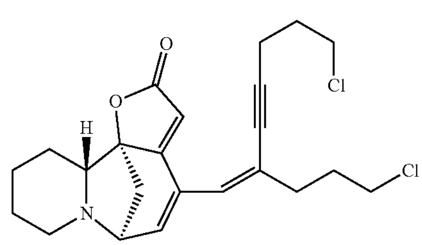 [SMILES: O=C1C=C2C(/C=C(\C#CCCCCl)CCCCl)=C[C@@H]3C[C@@]2(O1)[C@H]1CCCCN31] | 420.37 | 1.25 < IC50 < 2.5 |
| INVS-MG-125-IIB | 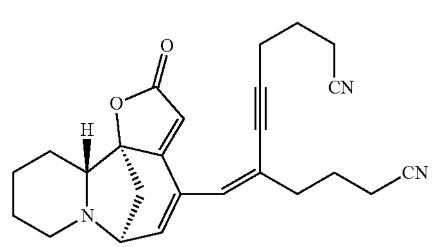 [SMILES: N#CCCCC#C/C(=C\C1=C[C@@H]2C[C@@]3(OC(=O)C=C13)[C@H]1CCCCN21)CCCC#N] | 401.5 | 40/35 at 10 uM |

TABLE 1-continued

| Sample code | Structure | M. Wt | HL-60, Dif50/IC50 |
|---|---|---|---|
| INVS-MG-144B | 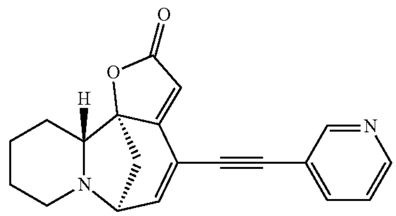 | 318.37 | 0.31 < IC50 < 0.625 |
| INVS-MG-147B | 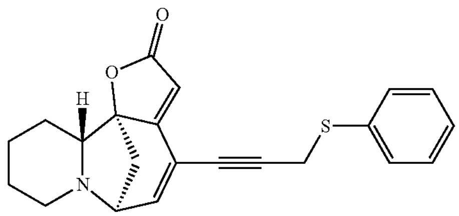 [SMILES: O=C1C=C2C(C#CCSc3ccccc3)=C[C@@H]3C[C@@]2(O1)[C@H]1CCCCN31] | 363.47 | 0.625 < IC50 < 1.25 |
| INVS-MG-149B | 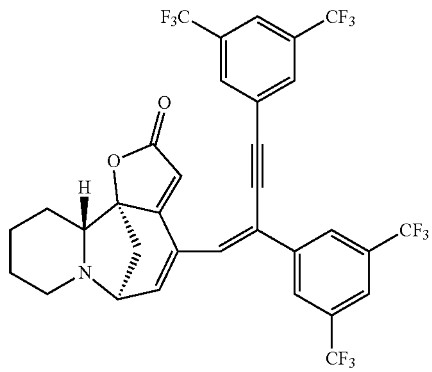 [SMILES: O=C1C=C2C(/C=C(\C#Cc3cc(C(F)(F)F)cc(C(F)(F)F)c3)c3cc(C(F)(F)F)cc(C(F)(F)F)c3)=C[C@@H]3C[C@@]2(O1)[C@H]1CCCCN31] | 691.51 | 1.25 < IC50 < 2.5 |
| INVS-MG-149B' | 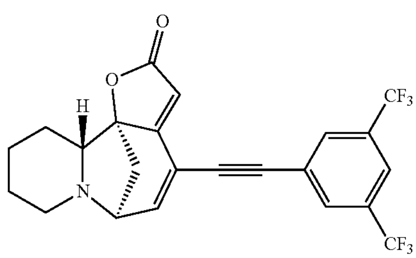 [SMILES: O=C1C=C2C(C#Cc3cc(C(F)(F)F)cc(C(F)(F)F)c3)=C[C@@H]3C[C@@]2(O1)[C@H]1CCCCN31] | 453.38 | 1.25 < IC50 < 2.5 |
| INVS-MG-157B | 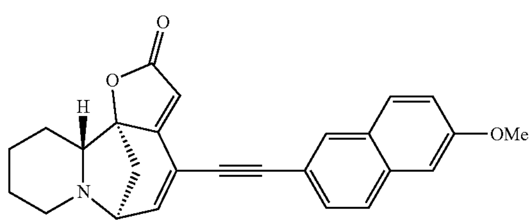 [SMILES: COc1ccc2cc(C#CC3=C[C@@H]4C[C@@]5(OC(=O)C=C35)[C@H]3CCCCN43)ccc2c1] | 397.47 | 0.07 < IC50 < 0.156 |
| INVS-MG-158B | 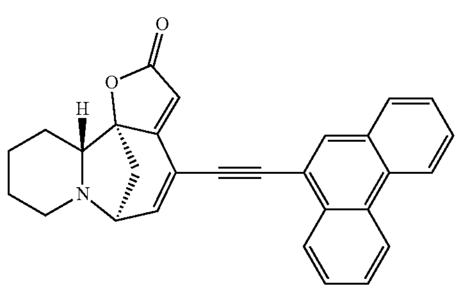 [SMILES: O=C1C=C2C(C#Cc3cc4ccccc4c4ccccc34)=C[C@@H]3C[C@@]2(O1)[C@H]1CCCCN31] | 417.5 | 0.07 < IC50 < 0.156 |

TABLE 1-continued
| Sample code | Structure | M. Wt | HL-60, Dif50/IC50 |
|---|---|---|---|
| INVS-MG-159A | 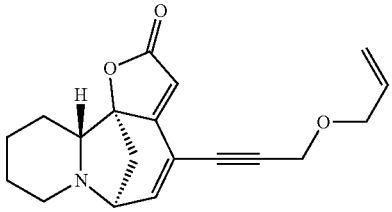 [SMILES: C=CCOCC#CC1=C[C@@H]2C[C@@]3(OC(=O)C=C13)[C@H]1CCCCN21] | 311.37 | 20/20 at 10 uM |
| INVS-MG-160B | 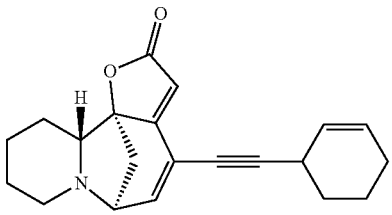 | 321.41 | 50/40 at 1.25 uM |
| INVS-MG-161B | 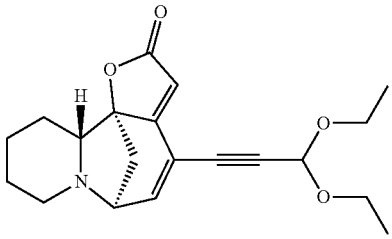 [SMILES: CCOC(C#CC1=C[C@@H]2C[C@@]3(OC(=O)C=C13)[C@H]1CCCCN21)OCC] | 343.42 | 2.5 < IC50 < 5 |
| INVS-MG-162B | 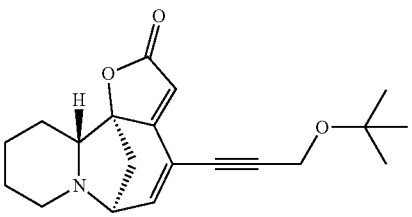 [SMILES: CC(C)(C)OCC#CC1=C[C@@H]2C[C@@]3(OC(=O)C=C13)[C@H]1CCCCN21] | 327.42 | 1.25 < IC50 < 2.5 |
| INVS-MG-163-IIB | 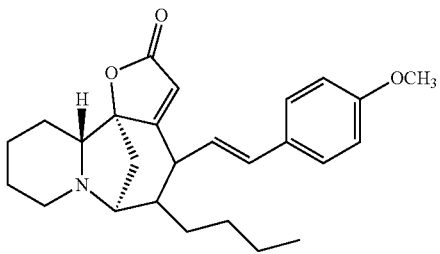 [SMILES: CCCCC1C(/C=C/c2ccc(OC)cc2)C2=CC(=O)O[C@@]23C[C@@H]1N1CCCC[C@@H]13] | 407.55 | IC50 < 10 |
| INVS-MG-164B | 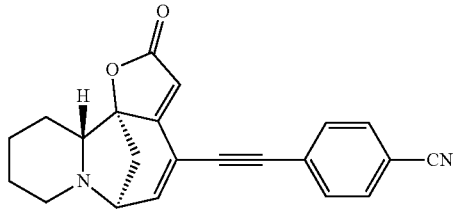 [SMILES: N#Cc1ccc(C#CC2=C[C@@H]3C[C@@]4(OC(=O)C=C24)[C@H]2CCCCN32)cc1] | 342.39 | 0.31 < IC50 < 0.625 |

TABLE 1-continued

| Sample code | Structure | M. Wt | HL-60, Dif50/IC50 |
| --- | --- | --- | --- |
| INVS-MG-165B | 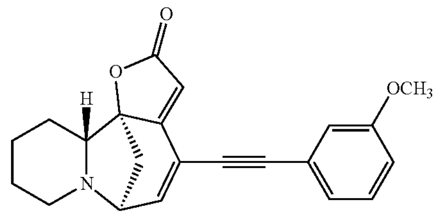 [SMILES: COc1cccc(C#CC2=C[C@@H]3C[C@@]4(OC(=O)C=C24)[C@H]2CCCCN32)c1] | 347.41 | 0.31 < IC50 < 0.625 |
| INVS-MG-166B | 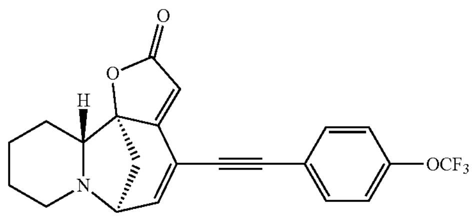 [SMILES: O=C1C=C2C(C#Cc3ccc(OC(F)(F)F)cc3)=C[C@@H]3C[C@@]2(O1)[C@H]1CCCCN31] | 401.38 | 0.31 < IC50 < 0.625 |
| INVS-MG-136-IIB | 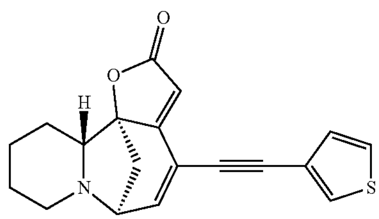 [SMILES: O=C1C=C2C(C#Cc3ccsc3)=C[C@@H]3C[C@@]2(O1)[C@H]1CCCCN31] | 323.41 | 0.156 < IC50 < 0.31 |
| INVS-MG-136-III | ·HCl | 359.87 | NT < IC50 < 0.07 |
| INVS-MG-167B | 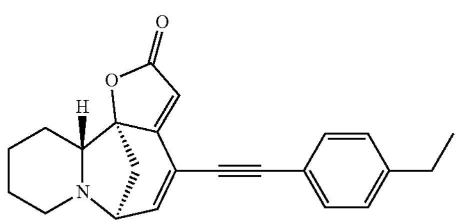 | 345.43 | 0.31 < IC50 < 0.625 |
| INVS-MG-168B | 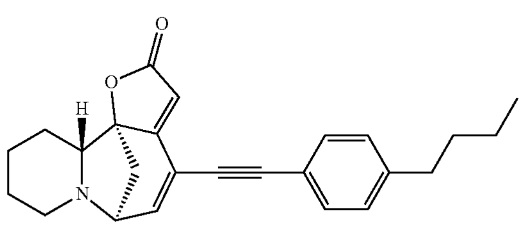 [SMILES: CCCCc1ccc(C#CC2=C[C@@H]3C[C@@]4(OC(=O)C=C24)[C@H]2CCCCN32)cc1] | 373.49 | 0.625 < IC50 < 1.25 |
| INVS-MG-169B | 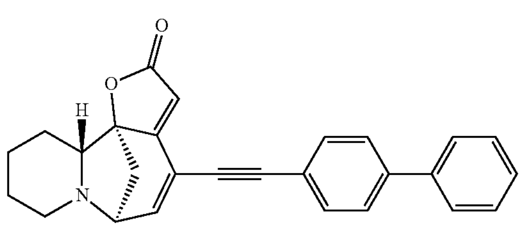 [SMILES: O=C1C=C2C(C#Cc3ccc(-c4ccccc4)cc3)=C[C@@H]3C[C@@]2(O1)[C@H]1CCCCN31] | 393.48 | IC50 < 0.07 |

TABLE 1-continued

| Sample code | Structure | M. Wt | HL-60, Dif50/IC50 |
|---|---|---|---|
| INVS-MG-170B | 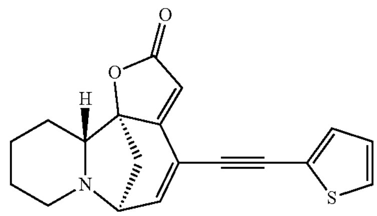 [SMILES: O=C1C=C2C(C#Cc3cccs3)=C[C@@H]3C[C@@]2(O1)[C@H]1CCCCN31] | 323.41 | 0.07 < IC50 < 0.156 |
| INVS-MG-175A | 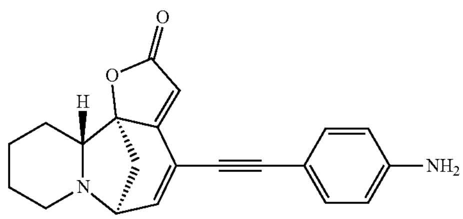 | 332.4 | 0.156 < Dif50 < 0.31 |
| INVS-MG-172C | 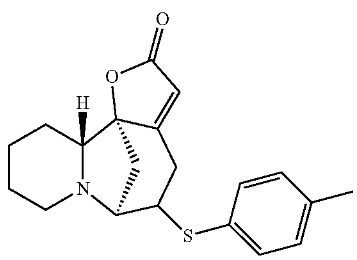 [SMILES: Cc1ccc(SC2CC3=CC(=O)O[C@@]34C[C@@H]2N2CCCC[C@@H]24)cc1] | 341.47 | 15 < Dif50 < 10 |
| INVS-MG-184B | 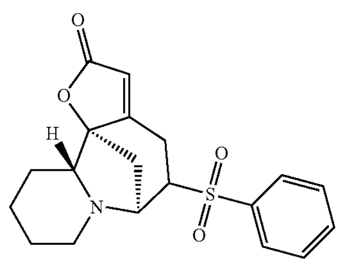 [SMILES: O=C1C=C2CC(S(=O)(=O)c3ccccc3)[C@@H]3C[C@@]2(O1)[C@H]1CCCCN31] | 359.44 | 5 < Dif50 < 7.5 |
| INVS-MG-146-IIIB | 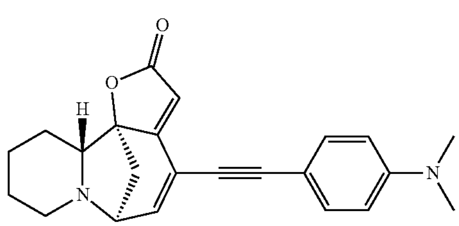 [SMILES: CN(C)c1ccc(C#CC2=C[C@@H]3C[C@@]4(OC(=O)C=C24)[C@H]2CCCCN32)cc1] | 360.45 | 0.07 < IC50 < 0.156 |
| INVS-MG-146-IV | 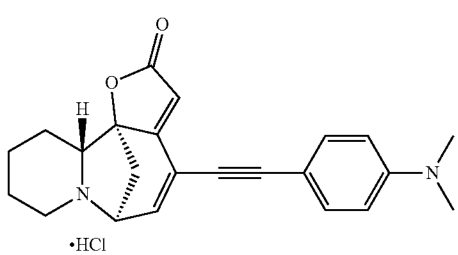 [SMILES: CN(C)c1ccc(C#CC2=C[C@@H]3C[C@@]4(OC(=O)C=C24)[C@H]2CCCCN32)cc1 ; Cl] | 396.91 | 0.07 < IC50 < 0.156 |

TABLE 1-continued
| Sample code | Structure | M. Wt | HL-60, Dif50/IC50 |
|---|---|---|---|
| INVS-MG-152-IIB | 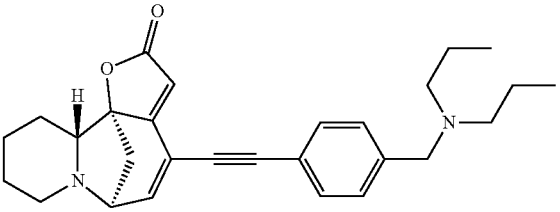 [SMILES: CCCN(CCC)Cc1ccc(C#CC2=C[C@@H]3C[C@@]4(OC(=O)C=C24)[C@H]2CCCCN32)cc1] | 354.49 | IC50 < 0.03 |
| INVS-MG-152-III | 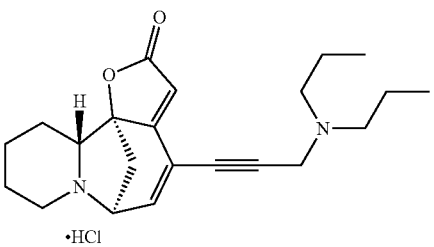 [SMILES: CCCN(CC#CC1=C[C@@H]2C[C@@]3(OC(=O)C=C13)[C@H]1CCCCN21)CCC ; Cl] ·HCl | 390.95 | IC50 < 0.03 |
| INVS-MG-157-IIB | 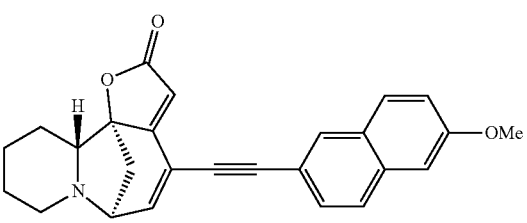 [SMILES: COc1ccc2cc(C#CC3=C[C@@H]4C[C@@]5(OC(=O)C=C35)[C@H]3CCCCN43)ccc2c1] | 397.47 | 0.07 < IC50 < 0.156 |
| INVS-MG-157-III | 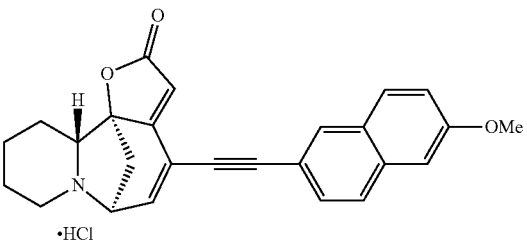 [SMILES: COc1ccc2cc(C#CC3=C[C@@H]4C[C@@]5(OC(=O)C=C35)[C@H]3CCCCN43)ccc2c1 ; Cl] ·HCl | 433.93 | 0.07 < IC50 < 0.156 |
| INVS-MG-158-IIB | 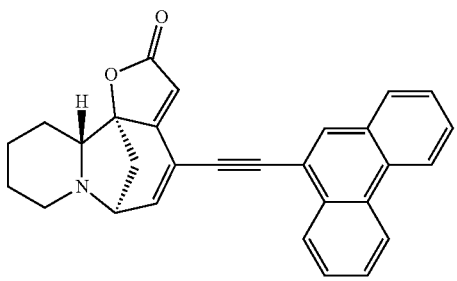 [SMILES: O=C1C=C2C(C#Cc3cc4ccccc4c4ccccc34)=C[C@@H]3C[C@@]2(O1)[C@H]1CCCCN31] | 417.5 | 0.03 < IC50 < 0.07 |
| INVS-MG-158-III | 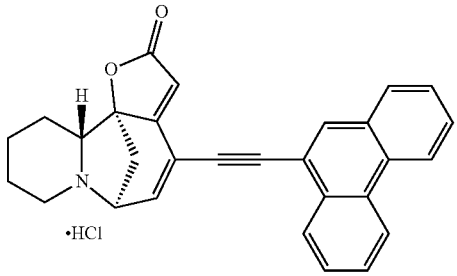 ·HCl | 453.96 | 0.07 < IC50 < 0.156 |

TABLE 1-continued

| Sample code | Structure | M. Wt | HL-60, Dif50/IC50 |
| --- | --- | --- | --- |
| INVS-MG-169-IIB | 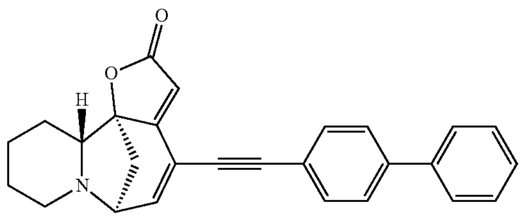 [SMILES: O=C1C=C2C(C#Cc3ccc(-c4ccccc4)cc3)=C[C@@H]3C[C@@]2(O1)[C@H]1CCCCN31] | 393.48 | 0.156 < IC50 < 0.31 |
| INVS-MG-169-III | •HCl | 429.94 | 0.07 < IC50 < 0.156 |
| INVS-MG-170-IIB | 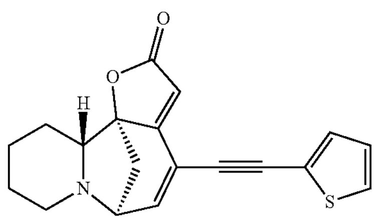 [SMILES: O=C1C=C2C(C#Cc3cccs3)=C[C@@H]3C[C@@]2(O1)[C@H]1CCCCN31] | 323.41 | 0.03 < IC50 < 0.07 |
| INVS-MG-170-III | •HCl | 359.87 | 0.07 < IC50 < 0.156 |
| INVS-MG-175-V | •HCl   •HCl | 405.32 | IC50 = 0.156 |
| INVS-MG-193B | 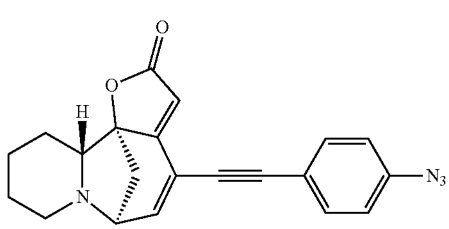 [SMILES: [N-]=[N+]=Nc1ccc(C#CC2=C[C@@H]3C[C@@]4(OC(=O)C=C24)[C@H]2CCCCN32)cc1] | 358.39 | IC50 = 0.31 |

TABLE 1-continued
| Sample code | Structure | M. Wt | HL-60, Dif50/IC50 |
| --- | --- | --- | --- |
| INVS-MG-193-III | 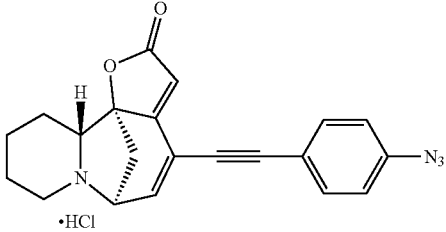 [SMILES: [N-]=[N+]=Nc1ccc(C#CC2=C[C@@H]3C[C@@]4(OC(=O)C=C24)[C@H]2CCCCN32)cc1 ; Cl] ·HCl | 394.85 | 0.156 < IC50 < 0.31 |
| INVS-MG-176B | 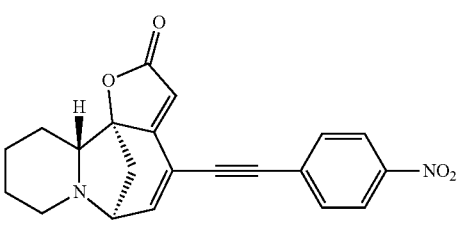 | 362.38 | 0.31 < IC50 < 0.625 |
| INVS-MG-176-II | 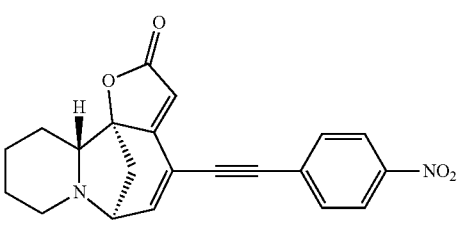 [SMILES: O=C1C=C2C(C#Cc3ccc([N+](=O)[O-])cc3)=C[C@@H]3C[C@@]2(O1)[C@H]1CCCCN31] ·HCl | 398.84 | 0.156 < IC50 < 0.31 |
| INVS-MG-179B | 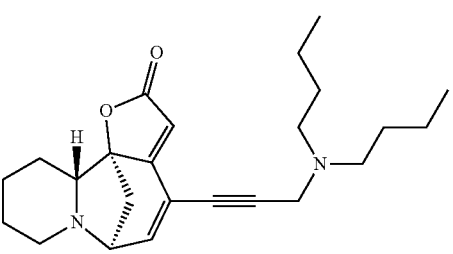 | 382.54 | 0.156 < IC50 < 0.31 |
| INVS-MG-179-II | 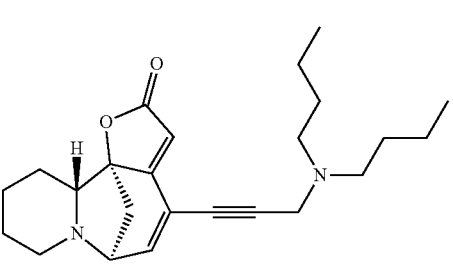 [SMILES: CCCCN(CC#CC1=C[C@@H]2C[C@@]3(OC(=O)C=C13)[C@H]1CCCCN21)CCCC] ·2HCl | 426.29 | 0.156 < IC50 < 0.31 |
| INVS-MG-207A | 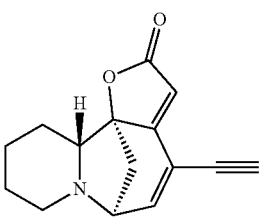 [SMILES: C#CC1=C[C@@H]2C[C@@]3(OC(=O)C=C13)[C@H]1CCCCN21] | 241.29 | 0.07 < IC50 < 0.156 |

TABLE 1-continued

| Sample code | Structure | M. Wt | HL-60, Dif50/IC50 |
|---|---|---|---|
| INVS-MG-207-II | 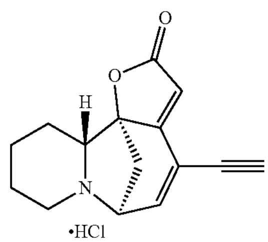 [SMILES: C#CC1=C[C@@H]2C[C@@]3(OC(=O)C=C13)[C@H]1CCCCN21 ; Cl] | 277.75 | 0.07 < Dif50 |
| INVS-MG-207-IIIA | 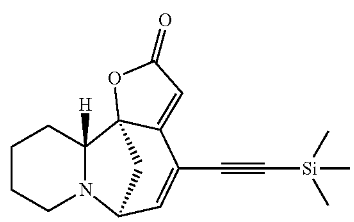 [SMILES: C[Si](C)(C)C#CC1=C[C@@H]2C[C@@]3(OC(=O)C=C13)[C@H]1CCCCN21] | 313.47 | 1.25 < IC50 < 2.5 |
| INVS-MG-209A | 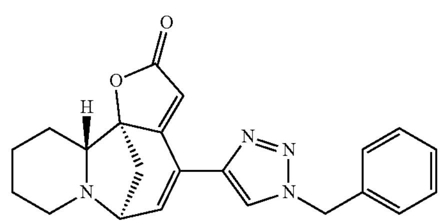 [SMILES: O=C1C=C2C(c3cn(Cc4ccccc4)nn3)=C[C@@H]3C[C@@]2(O1)[C@H]1CCCCN31] | 374.44 | Dif50/IC50 < 10 uM |
| INVS-MG-145-IIIA | 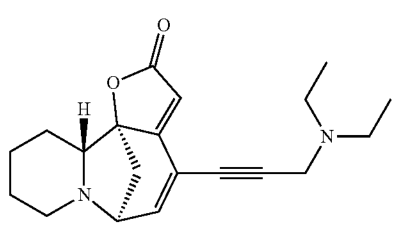 [SMILES: CCN(CC)CC#CC1=C[C@@H]2C[C@@]3(OC(=O)C=C13)[C@H]1CCCCN21] | 326.43 | 0.156 < IC50 < 0.31 |
| INVS-MG-145-V | 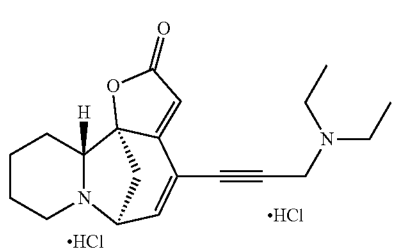 [SMILES: CCN(CC)CC#CC1=C[C@@H]2C[C@@]3(OC(=O)C=C13)[C@H]1CCCCN21 ; Cl ; Cl] | 399.35 | 0.07 < IC50 < 0.156 |
| INVS-MG-158-IVC | 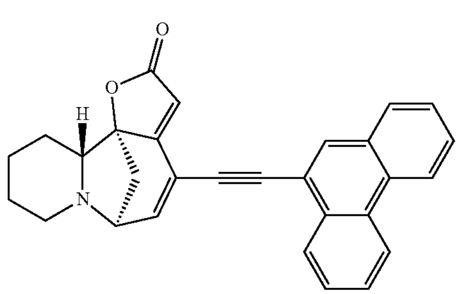 [SMILES: O=C1C=C2C(C#Cc3cc4ccccc4c4ccccc34)=C[C@@H]3C[C@@]2(O1)[C@H]1CCCCN31] | 417.5 | 0.156 < IC50 < 0.31 |

TABLE 1-continued
| Sample code | Structure | M. Wt | HL-60, Dif50/IC50 |
|---|---|---|---|
| INVS-MG-158-V | 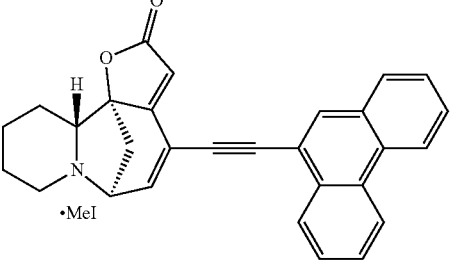 | 559.44 | IC50 < 5 |
| INVS-MG-158-VI | 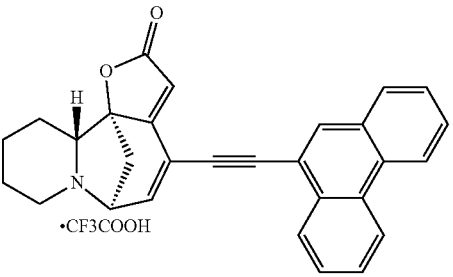 [SMILES: O=C1C=C2C(C#Cc3cc4ccccc4c4ccccc34)=C[C@@H]3C[C@@]2(O1)[C@H]1CCCCN31 ; "·CF3COOH"] | 531.52 | 0.156 < IC50 < 0.31 |
| INVS-MG-165-IIB | 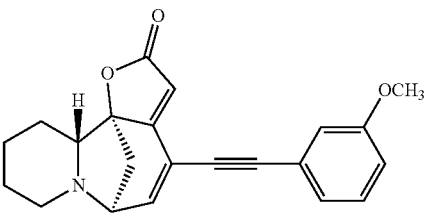 [SMILES: COc1cccc(C#CC2=C[C@@H]3C[C@@]4(OC(=O)C=C24)[C@H]2CCCCN32)c1] | 347.41 | 0.31 < IC50 < 0.625 |
| INVS-MG-165-III | 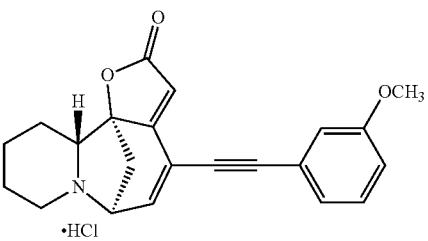 [SMILES: COc1cccc(C#CC2=C[C@@H]3C[C@@]4(OC(=O)C=C24)[C@H]2CCCCN32)c1 ; Cl] | 383.87 | 0.31 < IC50 < 0.625 |
| INVS-MG-99-IVB | 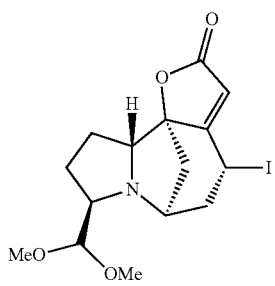 [SMILES: COC(OC)[C@H]1CC[C@H]2N1[C@@H]1C[C@@H](I)C3=CC(=O)O[C@@]32C1] | 403.21 | 0.31 < IC50 < 0.625 |
| INVS-MG-99-IVB-I | 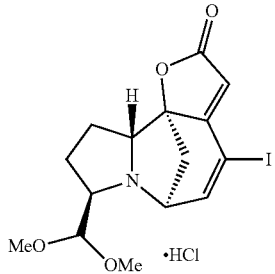 [SMILES: COC(OC)[C@H]1CC[C@H]2N1[C@@H]1C=C(I)C3=CC(=O)O[C@@]32C1 ; Cl] | 439.67 | 0.31 < IC50 < 0.625 |

TABLE 1-continued

| Sample code | Structure | M. Wt | HL-60, Dif50/IC50 |
| --- | --- | --- | --- |
| INVS-MG-99-IVD | 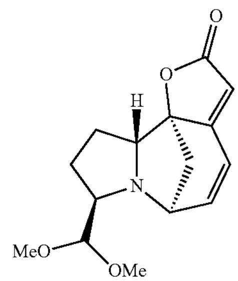 [SMILES: COC(OC)[C@H]1CC[C@H]2N1[C@@H]1C=CC3=CC(=O)O[C@@]32C1] | 277.32 | IC50 < 5 uM |
| INVS-MG-99-IVD-I | 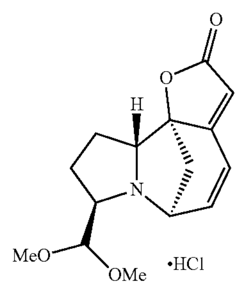 [SMILES: COC(OC)[C@H]1CC[C@H]2N1[C@@H]1C=CC3=CC(=O)O[C@@]32C1 ; Cl] | 313.78 | 5 uM < IC50 |
| INVS-MG-219A | 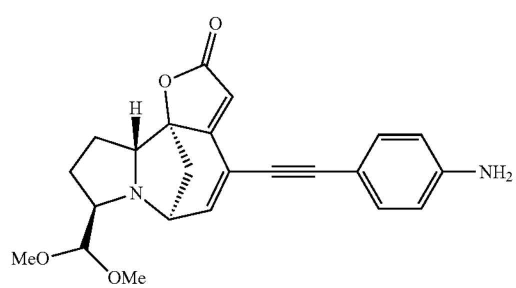 [SMILES: COC(OC)[C@H]1CC[C@H]2N1[C@@H]1C=C(C#Cc3ccc(N)cc3)C3=CC(=O)O[C@@]32C1] | 392.45 | 0.625 < IC50 < 1.25 |
| INVS-MG-220B | 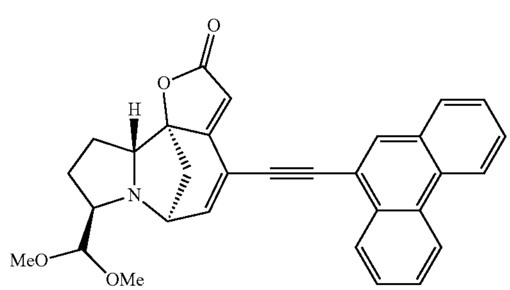 [SMILES: COC(OC)[C@H]1CC[C@H]2N1[C@@H]1C=C(C#Cc3cc4ccccc4c4ccccc34)C3=CC(=O)O[C@@]32C1] | 477.55 | IC50 = 0.156 |
| INVS-MG-220C | | 477.55 | 5 uM < IC50 | str?? aromatic disturbed

TABLE 1-continued

| Sample code | Structure | M. Wt | HL-60, Dif50/IC50 |
| --- | --- | --- | --- |
| INVS-MG-221B | 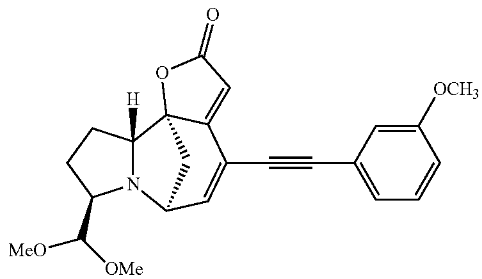 [SMILES: COc1cccc(C#CC2=C[C@@H]3C[C@@]4(OC(=O)C=C24)[C@H]2CC[C@H](C(OC)OC)N32)c1] | 407.46 | 0.625 < IC50 < 1.25 |
| INVS-MG-222B | 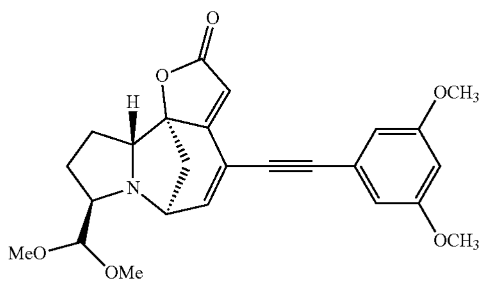 [SMILES: COc1cc(C#CC2=C[C@@H]3C[C@@]4(OC(=O)C=C24)[C@H]2CC[C@H](C(OC)OC)N32)cc(OC)c1] | 437.48 | IC50 < 0.03 |
| INVS-MG-223B | 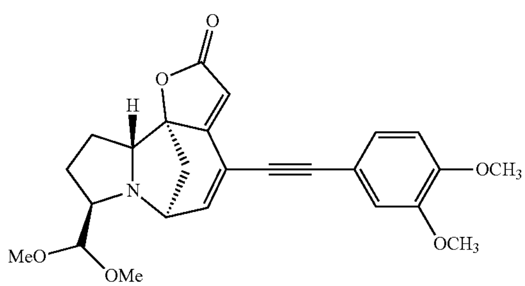 [SMILES: COc1ccc(C#CC2=C[C@@H]3C[C@@]4(OC(=O)C=C24)[C@H]2CC[C@H](C(OC)OC)N32)cc1OC] | 437.48 | 0.156 < IC50 < 0.31 |
| INVS-MG-224A | 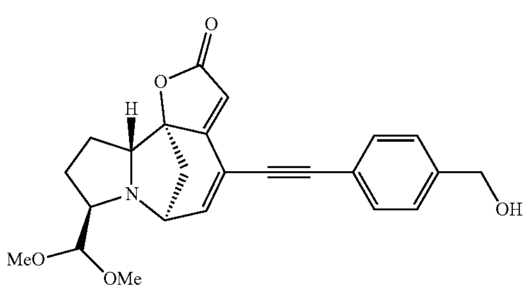 [SMILES: COC(OC)[C@H]1CC[C@H]2N1[C@@H]1C=C(C#Cc3ccc(CO)cc3)C3=CC(=O)O[C@@]32C1] | 407.46 | 0.156 < IC50 < 0.31 |
| INVS-MG-222-III | 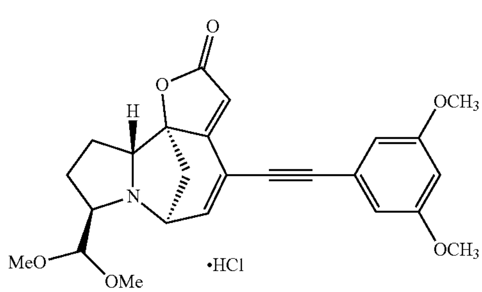 [SMILES: COc1cc(C#CC2=C[C@@H]3C[C@@]4(OC(=O)C=C24)[C@H]2CC[C@H](C(OC)OC)N32)cc(OC)c1 ; Cl] | 473.95 | |

TABLE 1-continued

| Sample code | Structure | M. Wt | HL-60, Dif50/IC50 |
|---|---|---|---|
| INVS-MG-184-IIB | 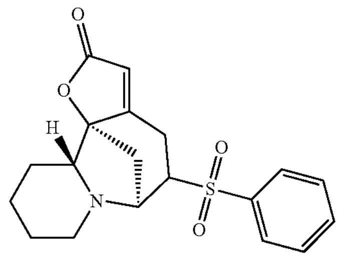 [SMILES: O=C1C=C2CC(S(=O)(=O)c3ccccc3)[C@@H]3C[C@@]2(O1)[C@H]1CCCCN31] | 359.44 | |
| INVS-MG-184-III | ·HCl | 395.9 | |
| INV-SZ-113-2 | 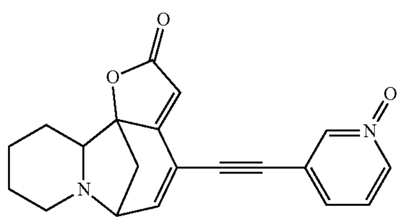 [SMILES: O=C1C=C2C(C#Cc3ccc[n+]([O-])c3)=CC3CC2(O1)C1CCCCN31] | 334 | 0.15 < IC50 < 0.31 |
| INV-SZ-114-1 | 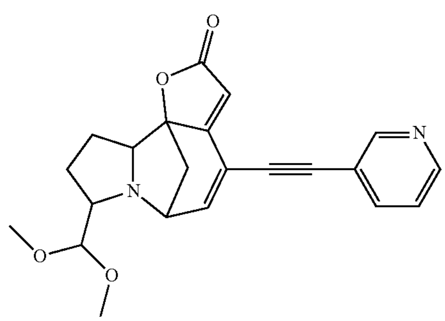 [SMILES: COC(OC)C1CCC2N1C1C=C(C#Cc3cccnc3)C3=CC(=O)OC32C1] | 378 | 0.07 < IC50 < 0.15 |
| INV-SZ-115-1 | 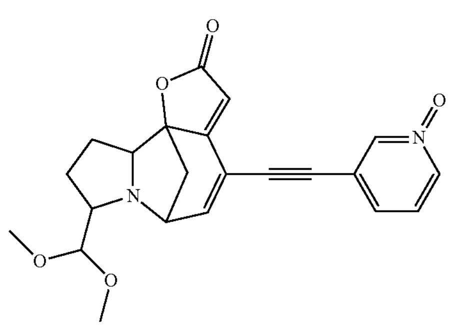 [SMILES: COC(OC)C1CCC2N1C1C=C(C#Cc3ccc[n+]([O-])c3)C3=CC(=O)OC32C1] | 394 | 0.15 < IC50 < 0.31 |

TABLE 1-continued

| Sample code | Structure | M. Wt | HL-60, Dif50/IC50 |
| --- | --- | --- | --- |
| INV-SZ-116-1 | 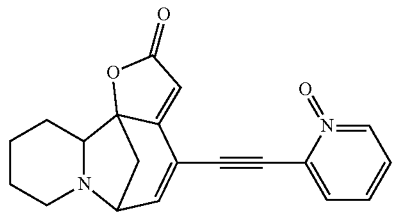 [SMILES: O=C1C=C2C(C#Cc3cccc[n+]3[O-])=CC3CC2(O1)C1CCCCN31] | 334 | 2.5 < IC50 < 5.0 |
| INV-SZ-117-3 | 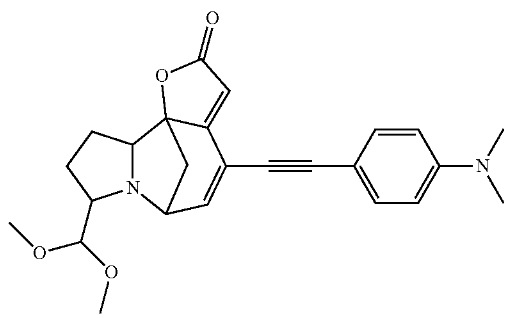 | 420 | 0.03 < IC50 < 0.07 |
| INV-117-4 | 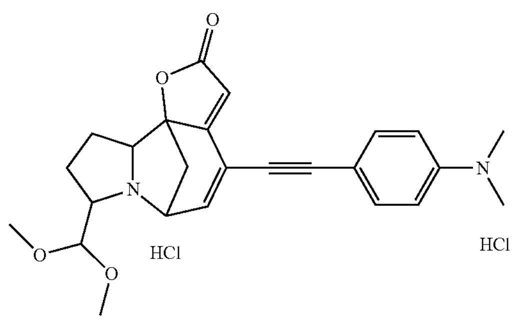 | 492 | 0.03 < IC50 < 0.07 |
| INV-SZ-118-2 | 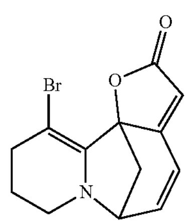 [SMILES: O=C1C=C2C=CC3CC2(O1)C1=C(Br)CCCN13] | 293 | 0.31 < IC50 < 0.62 |
| INV-SZ-120-1 | 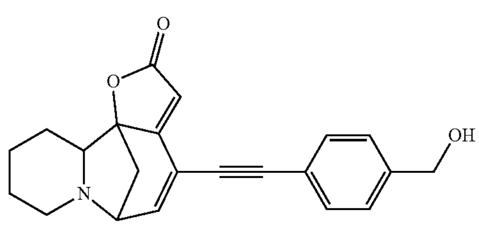 [SMILES: O=C1C=C2C(C#Cc3ccc(CO)cc3)=CC3CC2(O1)C1CCCCN31] | 347 | 0.07 < IC50 < 0.15 |
| INV-SZ-121-1 | 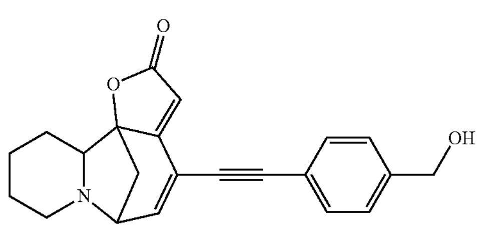 [SMILES: O=C1C=C2C(C#Cc3ccc(CO)cc3)=CC3CC2(O1)C1CCCCN31] | 349 | 0.37 < IC50 < 0.75 |

TABLE 1-continued

| Sample code | Structure | M. Wt | HL-60, Dif50/IC50 |
| --- | --- | --- | --- |
| INV-SZ-122-1 | 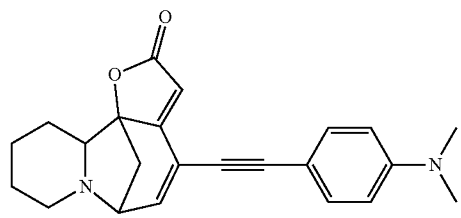 [SMILES: CN(C)c1ccc(C#CC2=CC3CC4(OC(=O)C=C24)C2CCCCN32)cc1] | 362 | 0.37 < IC50 < 0.75 |
| INV-SZ-123-2 | 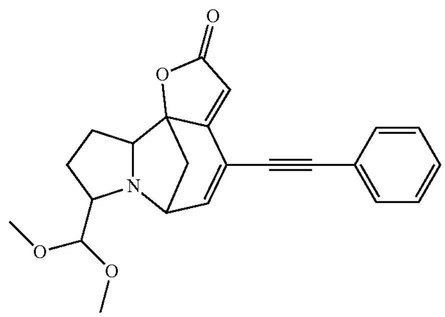 [SMILES: COC(OC)C1CCC2N1C1C=C(C#Cc3ccccc3)C3=CC(=O)OC32C1] | 377 | 0.37 < IC50 < 0.75 |
| INV-SZ-123-3 | 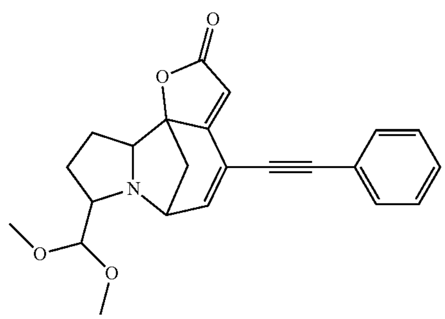 [SMILES: COC(OC)C1CCC2N1C1C=C(C#Cc3ccccc3)C3=CC(=O)OC32C1] | 123-3MW379 | IC50 < 5 |
| INV-SZ-125-1 | 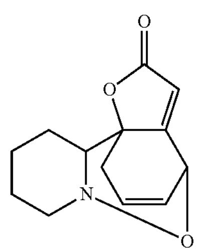 [SMILES: O=C1C=C2C3C=CCC2(O1)C1CCCCN1O3] | 233 | IC50 < 5 |
| INV-SZ-125-2 | 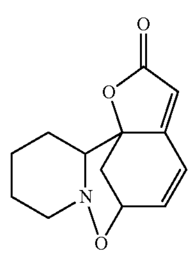 [SMILES: O=C1C=C2C=CC3CC2(O1)C1CCCCN1O3] | 233 | IC50 < 5 |
| INV-SZ-125-3 | 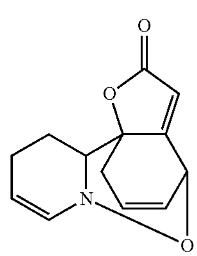 [SMILES: O=C1C=C2C3C=CCC2(O1)C1CCC=CN1O3] | 231 | IC50 < 5 |

TABLE 1-continued

| Sample code | Structure | M. Wt | HL-60, Dif50/IC50 |
| --- | --- | --- | --- |
| INV-SZ-127-1 | 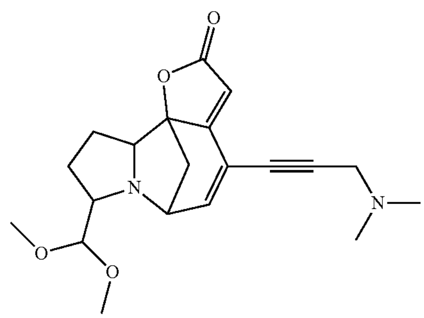 | 358 | 0.18 < IC50 < 0.37 |
| INV-SZ-129-1 | 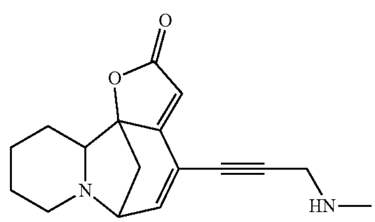 [SMILES: CNCC#CC1=CC2CC3(OC(=O)C=C13)C1CCCCN21] | 284 | 2.5 < IC50 < 5.0 |
| INV-SZ-134-1 | 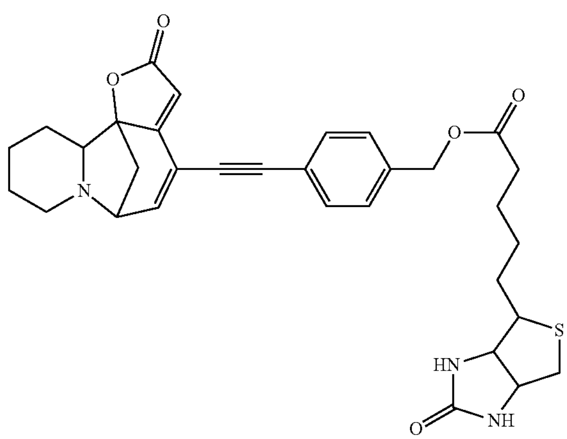 [SMILES: O=C1NC2CSC(CCCCC(=O)OCc3ccc(C#CC4=CC5CC6(OC(=O)C=C46)C4CCCCN54)cc3)C2N1] | 573 | |
| INV-SZ-132-1 | 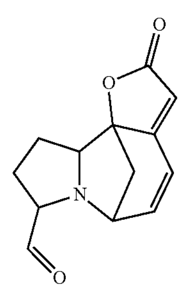 [SMILES: O=CC1CCC2N1C1C=CC3=CC(=O)OC32C1] | 231 | 1.25 < IC50 < 2.5 |
| INV-SZ-132-2 | 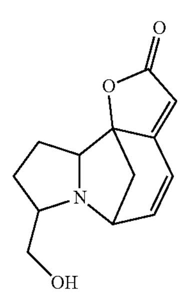 [SMILES: O=C1C=C2C=CC3CC2(O1)C1CCC(CO)N31] | 233 | 0.3 < IC50 < 0.6 |

TABLE 1-continued

| Sample code | Structure | M. Wt | HL-60, Dif50/IC50 |
|---|---|---|---|
| INV-SZ-133-1 | 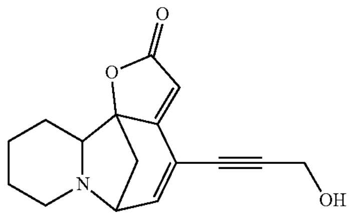 [SMILES: O=C1C=C2C(C#CCO)=CC3CC2(O1)C1CCCCN31] | 271 | 1.25 < IC50 < 2.5 |
| INV-SZ-136-1 | 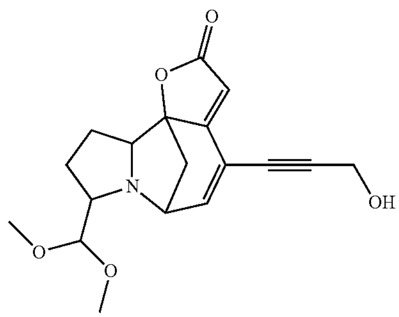 [SMILES: COC(OC)C1CCC2N1C1C=C(C#CCO)C3=CC(=O)OC32C1] | 331 | 0.15 < IC50 < 0.31 |
| INV-SZ-137-1 | 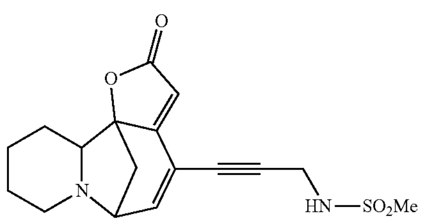 [SMILES: CS(=O)(=O)NCC#CC1=CC2CC3(OC(=O)C=C13)C1CCCCN21] | 348 | 0.07 < IC50 < 0.15 |
| INV-SZ-138-2 | 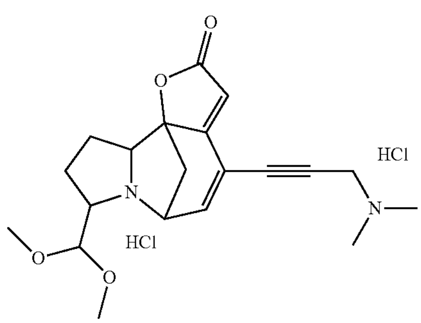 | 430 | 1.25 < IC50 < 2.5 |
| INV-SZ-140-1 | 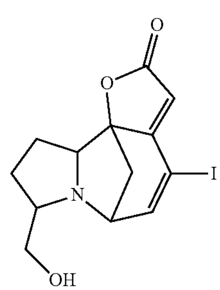 [SMILES: O=C1C=C2C(I)=CC3CC2(O1)C1CCC(CO)N31] | 359 | 0.07 < IC50 < 0.15 |

TABLE 1-continued

| Sample code | Structure | M. Wt | HL-60, Dif50/IC50 |
|---|---|---|---|
| INV-SZ-141-1 | 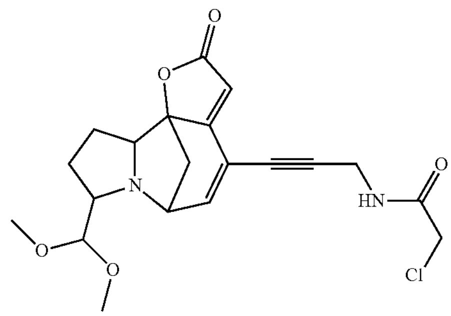 [SMILES: COC(OC)C1CCC2N1C1C=C(C#CCNC(=O)CCl)C3=CC(=O)OC32C1] | 406 | 1.25 < IC50 < 2.5 |

The analogs were then further tested for inhibiting growth against various cancer cell lines: AML (Mol3, OCI), Colon cancer (HCT116) and Ovary cancer (SKOV3). $IC_{50}$ are documented in Table 2.

TABLE 2

| Compounds | MOL3 (nM) | OCI (nM) | HCT116 P53+/+ (μM) | HCT116 P53−/− (μM) | SKOV3 P53+/+ (μM) | SKOV3 P53−/− (μM) |
|---|---|---|---|---|---|---|
| INVS-MG-82-II | 90 | 100 | 1.4 | 1.1 | 1.6 | 3.1 |
| INVS-MG-99B | 80 | 110 | 1.8 | 2.5 | 1.1 | 3 |
| INVS-MG-99D | 150 | 168 | 2.6 | 3.6 | 2.7 | 3.9 |
| INVS-MG-110B | 70 | 80 | 1.9 | 2.3 | 2.1 | 3 |
| INVS-MG-111B | 70 | 90 | 1.1 | 1.5 | 1.8 | 2.8 |
| INVS-MG-120A | 196 | 220 | 1.6 | 2.1 | 1.9 | 2.6 |
| INVS-MG-125A | 160 | 195 | 1.3 | 2 | 1.3 | 2.4 |
| INVS-MG-132A | 165 | 200 | 2.4 | 2.2 | 2.4 | 3.8 |
| INVS-MG-134C | 60 | 80 | 1 | 1.1 | 1.2 | 2.8 |
| INVS-MG-136B | 60 | 75 | 2.2 | 2.1 | 2.8 | 2.9 |
| INVS-MG-145A | 130 | 110 | 1.1 | 2.1 | 0.8 | 1.2 |
| INVS-MG-146B | 115 | 105 | 0.8 | 1.8 | 0.7 | 0.8 |
| INVS-MG-152A | 80 | 70 | 0.9 | 1.9 | <0.6 | 0.7 |
| INVS-MG-157B | 90 | 105 | 0.7 | 0.9 | <0.6 | 0.7 |
| INVS-MG-158B | 150 | 180 | 1.2 | 2.3 | 1.2 | 3.1 |
| INVS-MG-164B | 145 | 205 | 5.2 | 6.4 | 6.8 | 4.2 |
| INVS-MG-165B | 150 | 215 | 3.2 | 4.2 | 3.6 | 3.5 |
| INVS-MG-166B | >300 | >300 | 2.4 | 3.8 | 3.5 | 3.2 |
| INVS-MG-136-III | 100 | 115 | 1.8 | 2.2 | 0.7 | 1.1 |

All publications, patents and patent applications references herein are to be each individually considered to be incorporated by reference in their entirety.

The invention claimed is:

1. A securinine or norsecurinine analog of the structure:

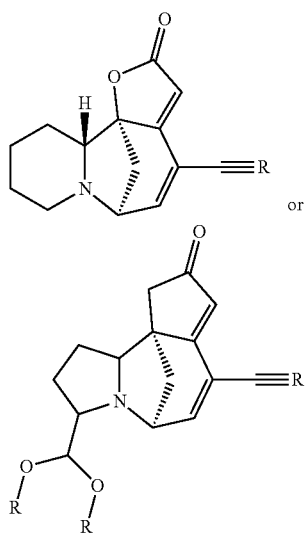

wherein R is a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), isopropyl, butyl, t-butyl, octyl, cyclopropyl, cyclopentyl, cyclo cyclopropyl, cyclopentyl; isopropenyl, cyclopentenyl; benzyl, phenyl, aminophenyl, dimethylaminophenyl, azidophenyl, methylphenyl, ethylphenyl, butylphenyl, t-butylphenyl, methoxyphenyl, trifluoromethoxyphenyl, fluorophenyl, cyanophenyl, pyridyl, N-oxide pyridyl, ethoxy, N-dimethylaminomethyl, N-diethylaminomethyl, N-dipropylaminomethyl, (triisopropylsilyl)oxymethyl, cyclopentylmethyl, phenoxymethyl, benzoxymethyl, t-butoxymethyl, propenyloxymethyl, thienyl, methoxynaphthalenyl, phenanthrenyl, phenyl, phenylmethyl, phenylmethylpropyl, pyran, phenol, cyclohexyl, hexyl, pentyl, propyl, ethyl, methyl, heptyl, octyl, nitro, nitroso, fluoromethylphenyl, trifluoromethylphenyl, bistrifluoromethylphenyl, bromophenyl, dibromophenyl, oxyethyl, hydroxylethyl, O-methylphenyl, fluorophenyl, cyclopropyl, methylcyclopentyl, heteroarene, azido, imino, O-methylnapthyl, napthyl, anthracyl, phenanthracyl, pyrimidyl, furyl, diethylmethyl ether, thiophyl, thioaryl, thioalkyl, phenylnitryl, sulfhydryl, sulfyl, sulfonato, carboxy, aniline, anisole, phenylmethanol, biphenyl, phenylamyl, nitrile, O tri fluoro methyl, di fluoro phenyl, siyl, silyl ether, O-(triisopropyl)silyl, methyl-O-(triisopropyl)silyl, methyl-O-methyl, phenylmethylnitryl, butylnitryl, carboxyato, methyl-O t-butyl, phenyl-O-(trifluoro)methyl, propylphenyl, dimethylamine, methylamine, phospho, trimethylamine, dimethylaminophenyl, dipropylmethylamine, toluene, xylene, aniline, or combinations thereof.

2. A pharmaceutical composition comprising the securinine or norsecurinine analog of claim 1 and a pharmaceutically acceptable carrier.

3. The pharmaceutical composition according to claim 2, further comprising a vaccinating antigen.

4. A method of inhibiting the proliferation human leukemia cells in a subject, wherein the method comprises administering a therapeutically effective amount of the securinine or norsecurinine analog of claim 1 to the subject.

5. A securinine or norsecurnine analog of the structure selected from the group consisting of:

INVS-MG-56A

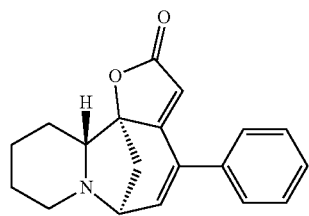

INVS-MG-54B

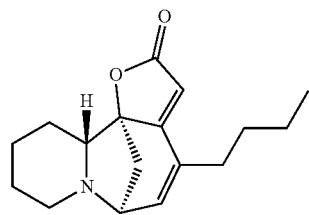

INVS-MG-63B

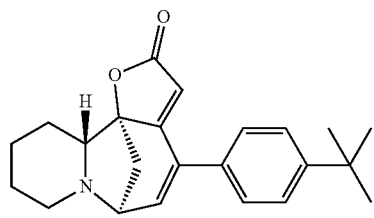

INVS-MG-64A

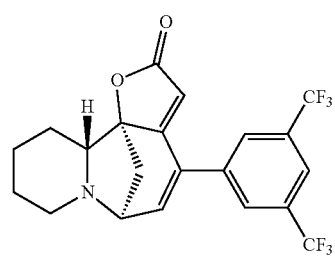

-continued

INVS-MG-65B

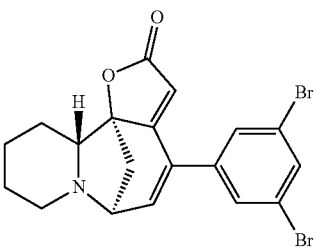

INVS-MG-108B

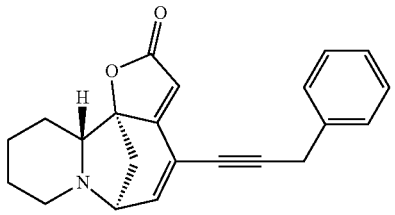

INVS-MG-109-IIA

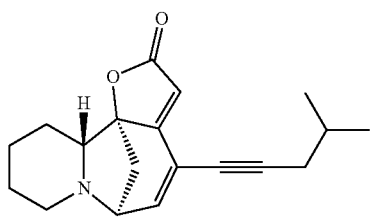

INVS-MG-110B

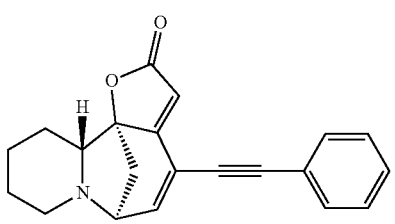

INVS-MG-111B

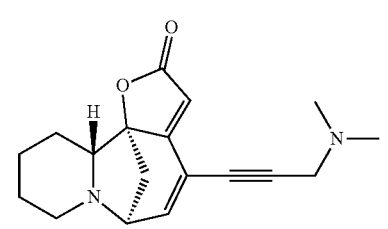

INVS-MG-113A

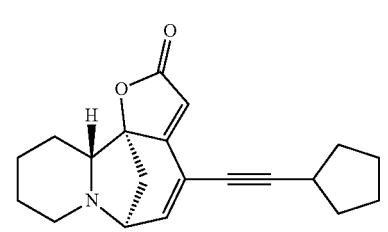

INVS-MG-117B

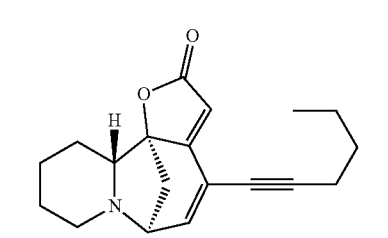

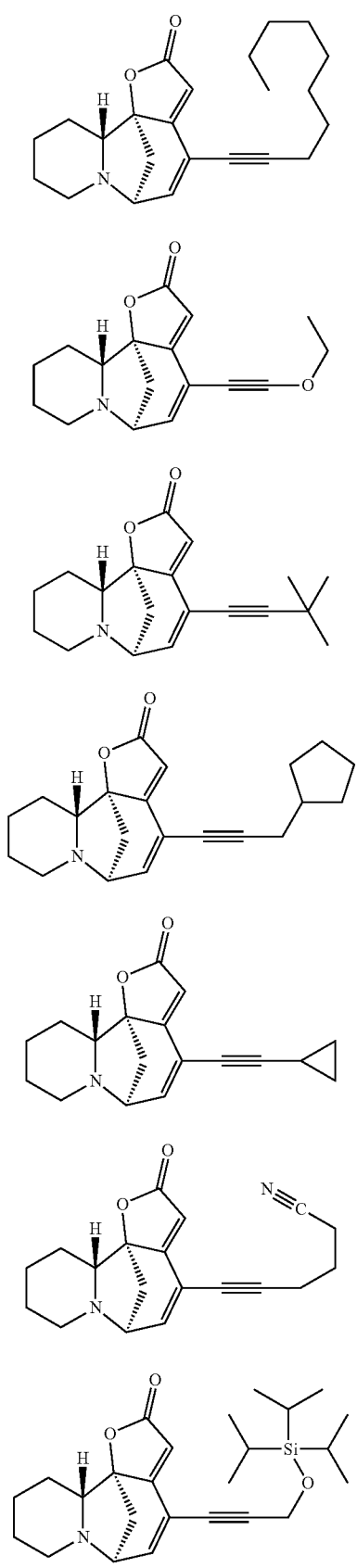
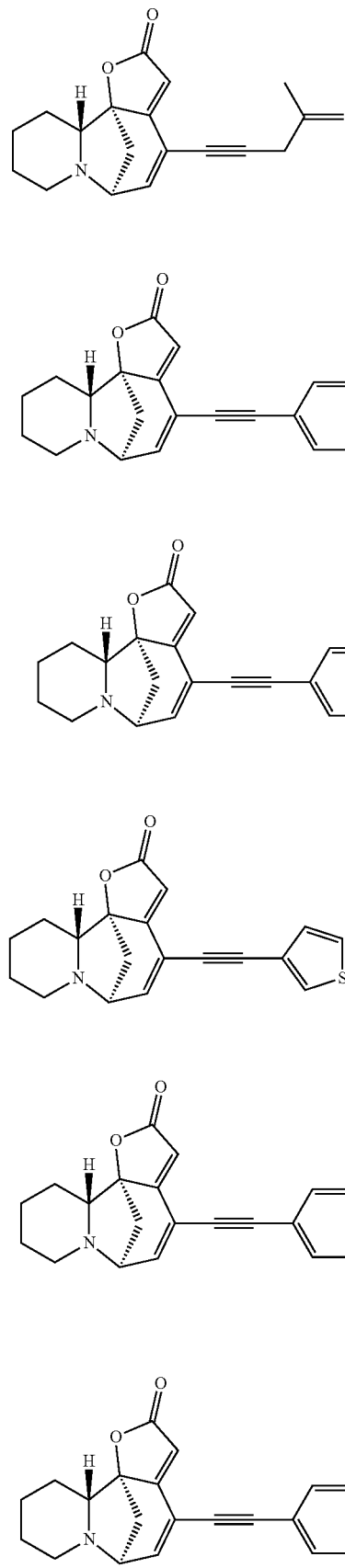

INVS-MG-137B
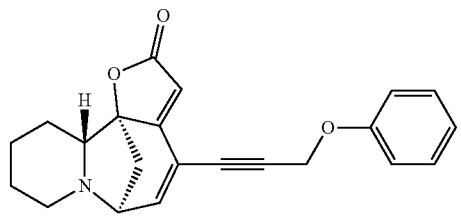
INVS-MG-152A
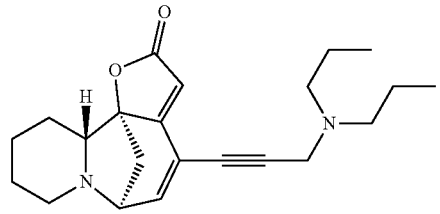
INVS-MG-138B
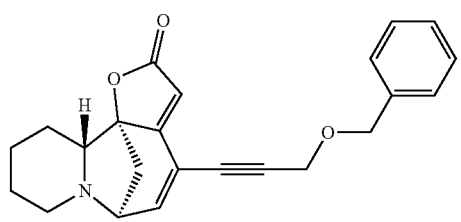
INVS-MG-157B
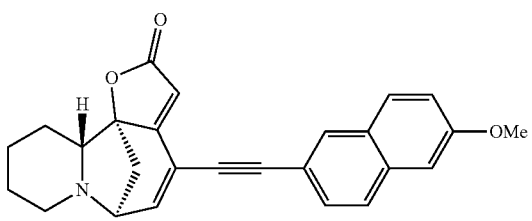
INVS-MG-145A
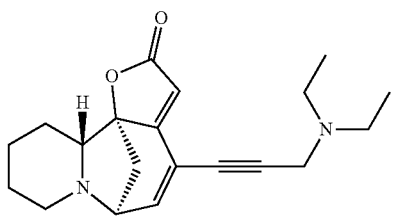
INVS-MG-158B
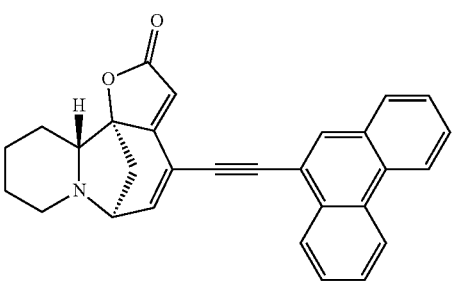
INVS-MG-146B
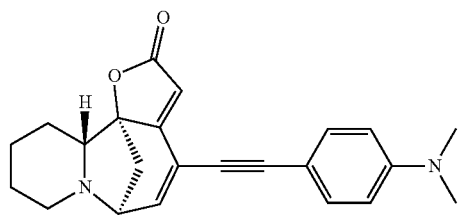
INVS-MG-159A
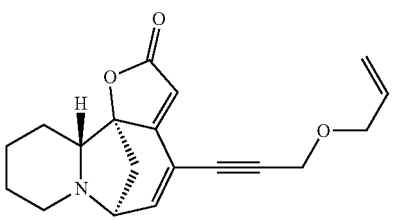
INVS-MG-150B
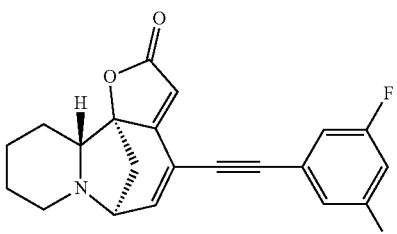
INVS-MG-160B
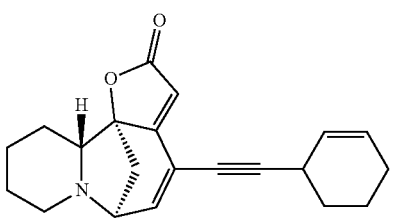
INVS-MG-151B
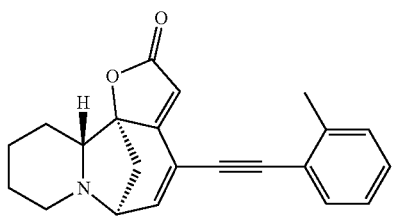
INVS-MG-161B
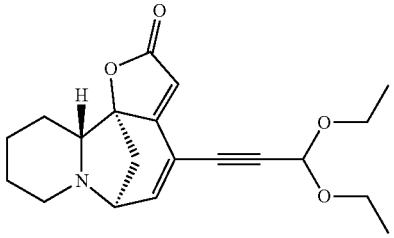

-continued
INVS-MG-162B
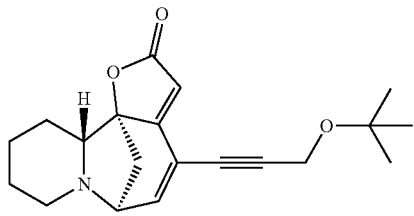
INVS-MG-164B
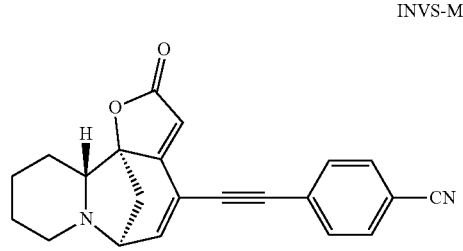
INVS-MG-165B
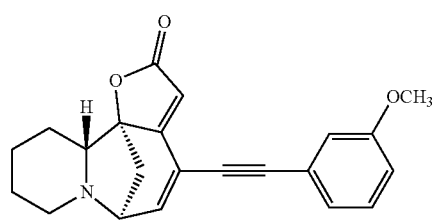
INVS-MG-166B
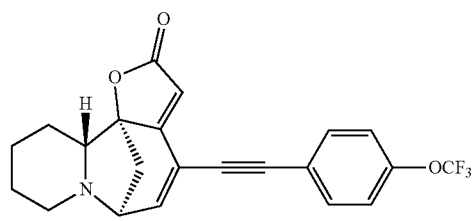
INVS-MG-167B
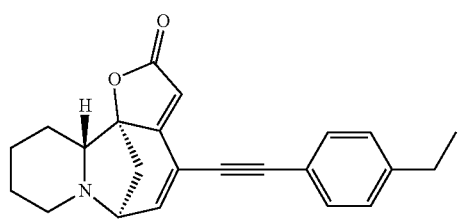
INVS-MG-168B
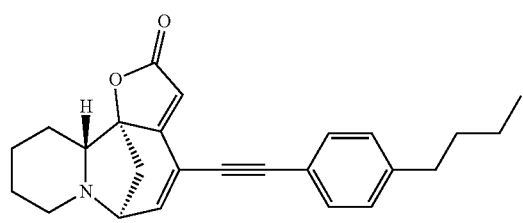
-continued
INVS-MG-169B
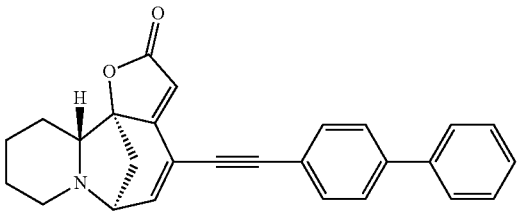
INVS-MG-170B
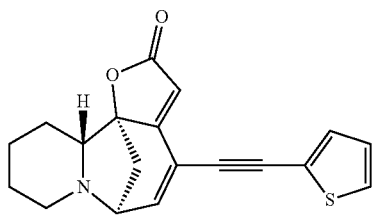
INVS-MG-175A
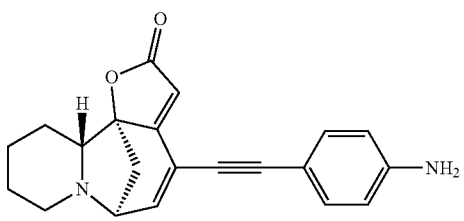
INVS-MG-193B
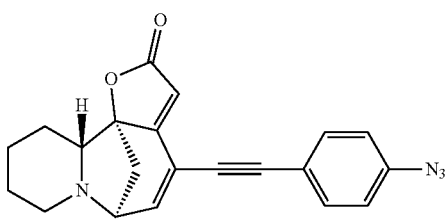
INVS-MG-70
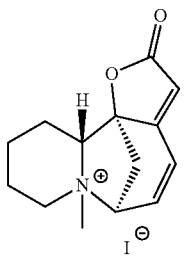
INVS-MG-72
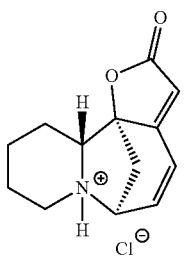

| 203 -continued | 204 -continued |
|---|---|
| INVS-MG-83 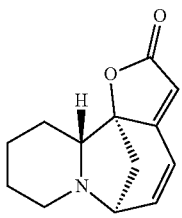 ·[CH(OH)COOH]₂ | INVS-MG-157-III 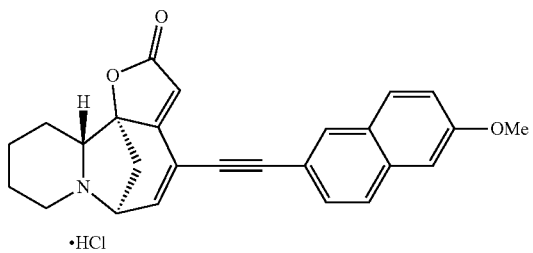 ·HCl |
| INVS-MG-71 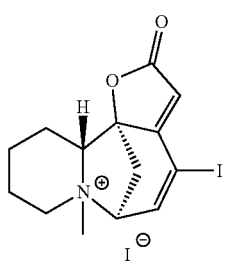 | INVS-MG-158-III 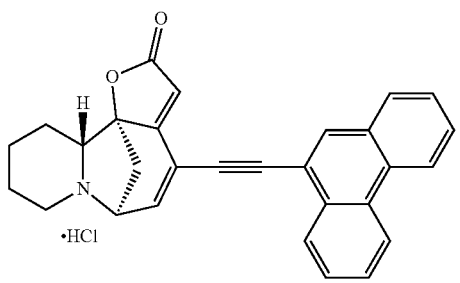 ·HCl |
| INVS-MG-73 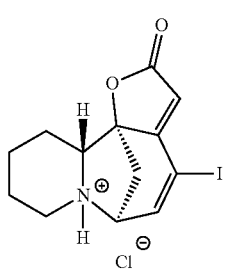 | INVS-MG-169-III 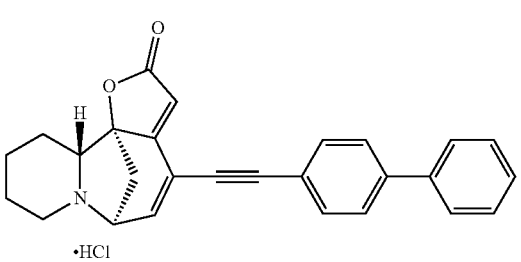 ·HCl |
| INVS-MG-84 <br> ·[CH(OH)COOH]₂ | INVS-MG-170-III 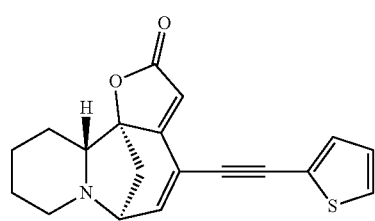 ·HCl |
| INVS-MG-111-IV 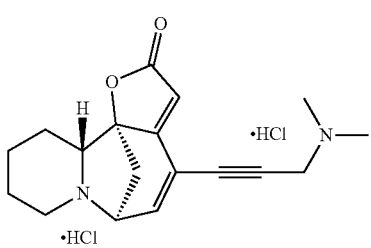 ·HCl | INVS-MG-146-III 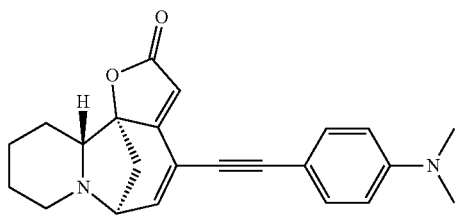 ·2HCl |
| INVS-MG-125-III 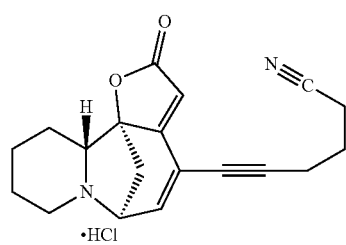 ·HCl | INVS-MG-152-III 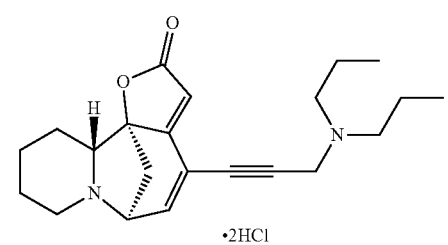 ·2HCl |

INVS-MG-175-V
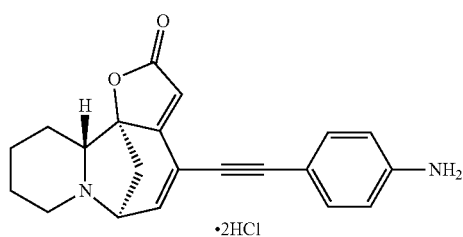
•2HCl
INV-SZ-116-1
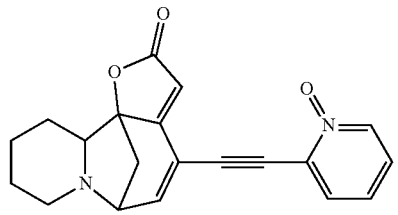
INVS-MG-193-III
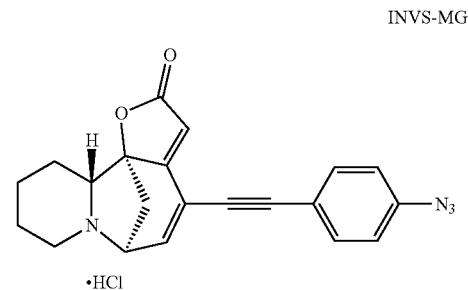
•HCl
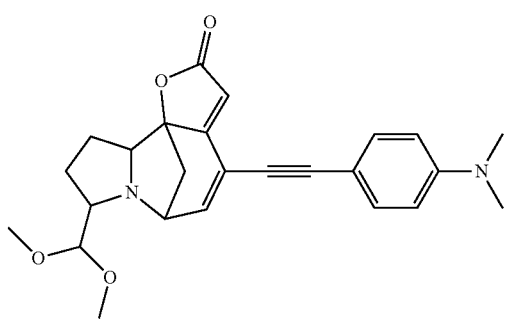
INV-SZ-113-2
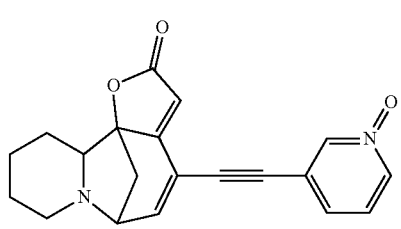
INV-SZ-118-2
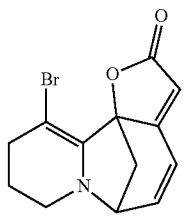
INV-SZ-114-1
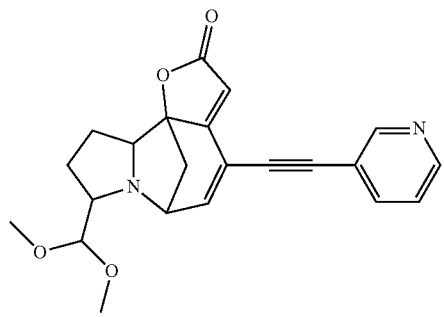
INV-SZ-120-1
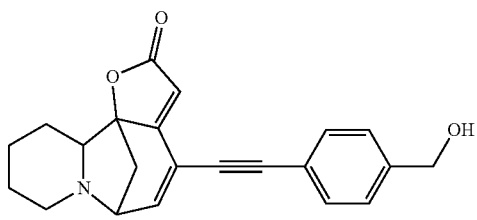
INV-SZ-115-1
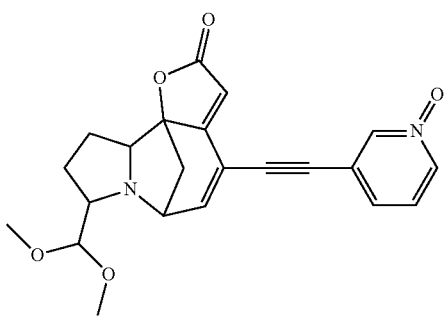
INV-SZ-121-1
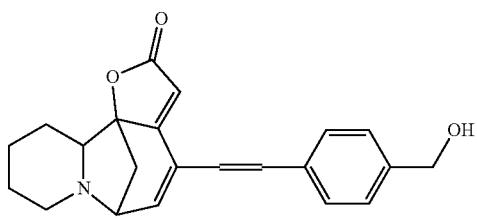

-continued
INV-SZ-122-1
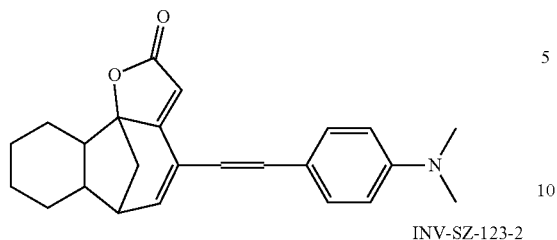
INV-SZ-123-2
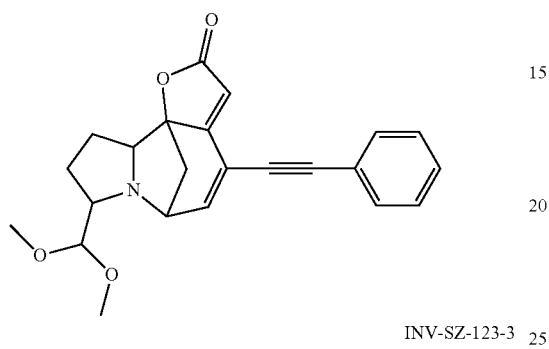
INV-SZ-123-3
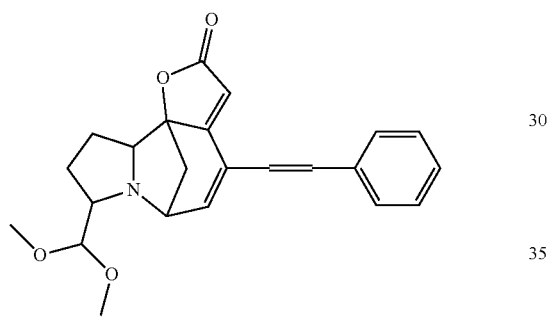
INV-SZ-125-1
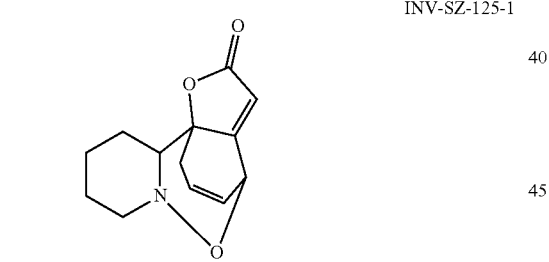
-continued
INV-SZ-125-2
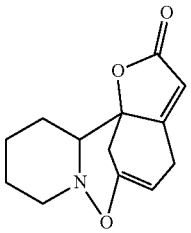
INV-SZ-125-3
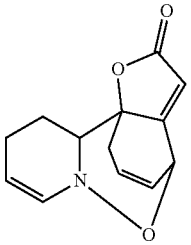
INV-SZ-127-1
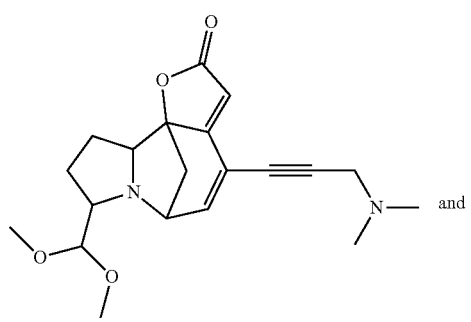 and
INV-SZ-129-1
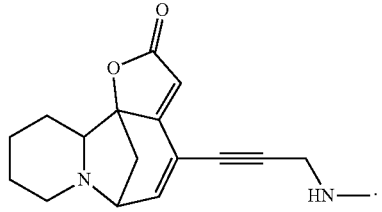
* * * * *

UNITED STATES PATENT AND TRADEMARK OFFICE
CERTIFICATE OF CORRECTION

PATENT NO. : 9,827,229 B2
APPLICATION NO. : 15/026749
DATED : November 28, 2017
INVENTOR(S) : Mahesh K. Gundluru et al.

Page 1 of 2

It is certified that error appears in the above-identified patent and that said Letters Patent is hereby corrected as shown below:

In the Specification

Column 3, Line 1, please replace

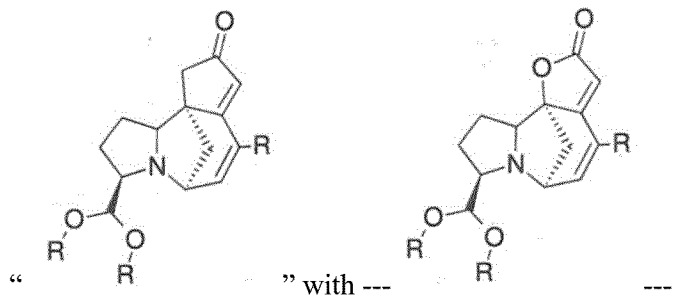

" with ---  ---

Column 5, Line 13, please replace

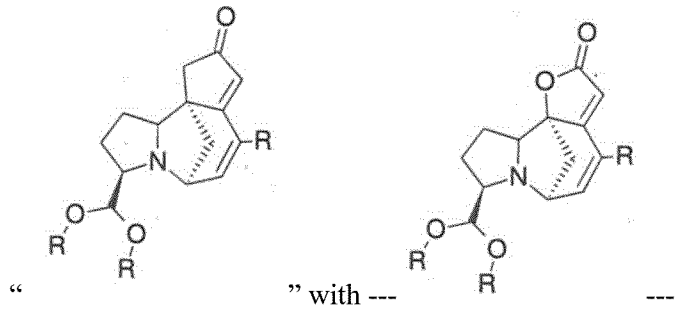

" with ---  ---

Signed and Sealed this
Twenty-sixth Day of March, 2019

Andrei Iancu
*Director of the United States Patent and Trademark Office*

CERTIFICATE OF CORRECTION (continued)

Column 6, Line 25, please replace

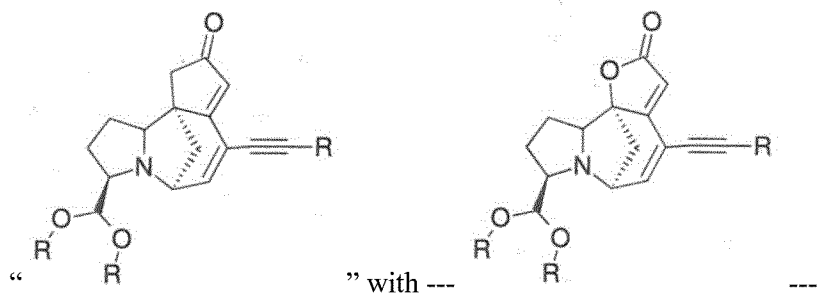

" with ---   ---

Column 114, Line 1, please replace

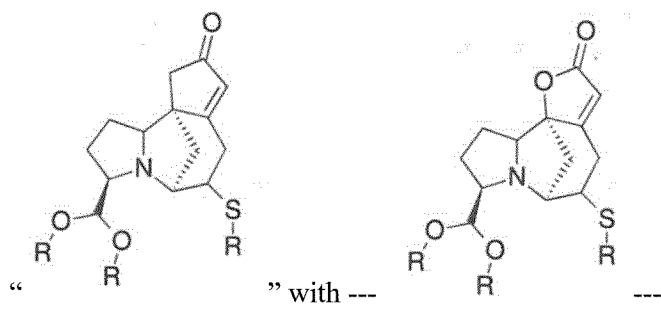

" with ---   ---

Column 114, Line 13, please replace

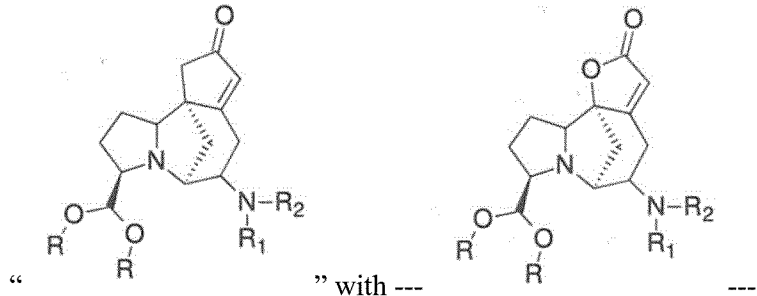

" with ---   ---

In the Claims

Claim 1, Column 194, Line 30, please replace

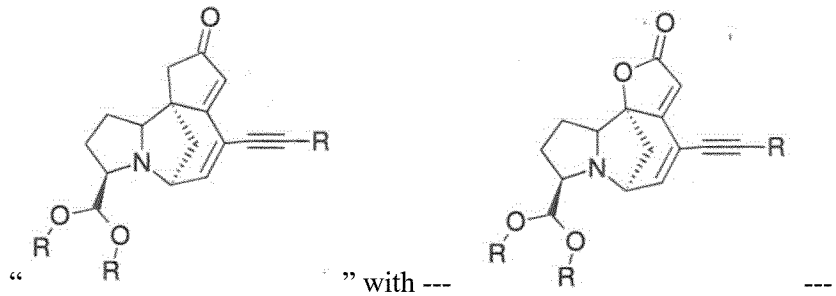

" with ---   ---